(12) United States Patent
Turkel et al.

(10) Patent No.: US 11,819,541 B2
(45) Date of Patent: Nov. 21, 2023

(54) INJECTION PARADIGM FOR ADMINISTRATION OF BOTULINUM TOXINS

(71) Applicant: Allergan, Inc., North Chicago, IL (US)

(72) Inventors: Catherine C. Turkel, Newport Coast, CA (US); Sheena K. Aurora, Seattle, WA (US); Mitchell F. Brin, Newport Beach, CA (US); David W. Dodick, Scottsdale, AZ (US)

(73) Assignee: Allergan, Inc., North Chicago, IL (US)

( * ) Notice: Subject to any disclaimer, the term of this patent is extended or adjusted under 35 U.S.C. 154(b) by 0 days.

(21) Appl. No.: 17/347,317

(22) Filed: Jun. 14, 2021

(65) Prior Publication Data

US 2021/0299232 A1   Sep. 30, 2021

Related U.S. Application Data

(60) Division of application No. 16/564,294, filed on Sep. 9, 2019, now Pat. No. 11,033,610, which is a division of application No. 15/707,452, filed on Sep. 18, 2017, now Pat. No. 10,406,213, which is a division of application No. 15/057,866, filed on Mar. 1, 2016, now Pat. No. 9,764,011, which is a continuation of application No. 13/863,522, filed on Apr. 16, 2013, now Pat. No. 9,279,001, which is a continuation-in-part of application No. 13/075,485, filed on Mar. 30, 2011, now Pat. No. 8,501,195.

(60) Provisional application No. 61/320,667, filed on Apr. 2, 2010, provisional application No. 61/319,230, filed on Mar. 30, 2010.

(51) Int. Cl.
| | | |
|---|---|---|
| A61K 39/08 | (2006.01) | |
| C07K 14/33 | (2006.01) | |
| A61K 38/48 | (2006.01) | |
| A61K 9/00 | (2006.01) | |
| A61K 35/74 | (2015.01) | |

(52) U.S. Cl.
CPC ........ *A61K 38/4893* (2013.01); *A61K 9/0019* (2013.01); *A61K 35/74* (2013.01); *C07K 14/33* (2013.01); *C12Y 304/24069* (2013.01)

(58) Field of Classification Search
None
See application file for complete search history.

(56) References Cited

U.S. PATENT DOCUMENTS

| | | |
|---|---|---|
| 5,437,291 A | 8/1995 | Pasricha et al. |
| 5,512,547 A | 4/1996 | Johnson et al. |
| 5,670,484 A | 9/1997 | Binder |
| 5,714,468 A | 2/1998 | Binder |
| 5,766,605 A | 6/1998 | Sanders et al. |
| 5,989,545 A | 11/1999 | Foster et al. |
| 6,063,768 A | 5/2000 | First |
| 6,139,845 A | 10/2000 | Donovan |
| 6,299,893 B1 | 10/2001 | Schwartz et al. |
| 6,306,423 B1 | 10/2001 | Donovan et al. |
| 6,312,708 B1 | 11/2001 | Donovan |
| 6,358,917 B1 | 3/2002 | Carruthers et al. |
| 6,423,319 B1 | 7/2002 | Brooks et al. |
| 6,447,787 B1 | 9/2002 | Gassner et al. |
| 6,458,365 B1 | 10/2002 | Aoki et al. |
| 6,464,986 B1 | 10/2002 | Aoki et al. |
| 6,585,993 B2 | 7/2003 | Donovan et al. |
| 6,623,742 B2 | 9/2003 | Voet |
| 6,787,517 B1 | 9/2004 | Gil et al. |
| 6,838,434 B2 | 1/2005 | Voet |
| 6,896,886 B2 | 5/2005 | Aoki et al. |
| 7,172,763 B2 | 2/2007 | Aoki et al. |
| 7,270,287 B2 | 9/2007 | First |
| 7,393,537 B2 | 7/2008 | Ackerman |
| 7,655,244 B2 | 2/2010 | Blumenfeld |
| 7,704,511 B2 | 4/2010 | Turkel et al. |
| 7,758,872 B1 | 7/2010 | Finzi |
| 7,811,587 B2 | 10/2010 | Donovan |
| 7,824,694 B2 | 11/2010 | First et al. |
| 7,897,147 B2 | 3/2011 | Dadas |
| 7,977,335 B2 | 7/2011 | Gil et al. |
| 7,981,433 B2 | 7/2011 | Blumenfeld |
| 8,048,423 B2 | 11/2011 | First |
| 8,241,641 B2 | 8/2012 | Blumenfeld |
| 8,258,096 B2 | 9/2012 | Yeomans et al. |
| 8,414,902 B2 | 4/2013 | Finzi |
| 8,420,106 B1 | 4/2013 | Binder |

(Continued)

FOREIGN PATENT DOCUMENTS

| | | |
|---|---|---|
| DE | 10150415 A1 | 5/2003 |
| WO | WO-1995/030431 A1 | 11/1995 |

(Continued)

OTHER PUBLICATIONS

Aoki K., et al., Mechanisms of the antinociceptive effect of subcutaneous Botox: Inhibition of peripheral and central nociceptive processing, Cephalalgia Sep. 2003;23(7):649.

(Continued)

*Primary Examiner* — Christine J Saoud
*Assistant Examiner* — Jon M Lockard
(74) *Attorney, Agent, or Firm* — Foley Hoag LLP; Hathaway P. Russell; Thi K. Dio

(57) ABSTRACT

Disorders such as headaches can be treated by administration of a botulinum toxin to a patient suffering therefrom, such as a migraine headache. A combined a fixed site/fixed dose and an optional follow the pain variable dosage and injection site paradigm is disclosed for optimizing clinical effectiveness of botulinum toxin administration for patients suffering headache, particularly chronic migraine.

19 Claims, 17 Drawing Sheets

(56) References Cited

U.S. PATENT DOCUMENTS

| | | |
|---|---|---|
| 8,470,337 B2 | 6/2013 | Manack et al. |
| 8,501,195 B2 | 8/2013 | Turkel et al. |
| 8,512,984 B2 | 8/2013 | Foster et al. |
| 8,530,425 B2 | 9/2013 | Blumenfeld |
| 8,603,779 B2 | 12/2013 | Foster et al. |
| 8,603,983 B2 | 12/2013 | Blumenfeld |
| 8,609,112 B2 | 12/2013 | Blumenfeld et al. |
| 8,609,113 B2 | 12/2013 | Blumenfeld et al. |
| 8,617,569 B2 | 12/2013 | Binder |
| 8,617,571 B2 | 12/2013 | Blumenfeld |
| 8,691,769 B2 | 4/2014 | Borodic et al. |
| 8,734,810 B2 | 5/2014 | Blumenfeld |
| 8,846,622 B2 | 9/2014 | Blumenfeld |
| 8,865,186 B2 | 10/2014 | Ichtchenko et al. |
| 8,889,151 B2 | 11/2014 | Turkel et al. |
| 8,926,991 B2 | 1/2015 | Borodic |
| 8,936,790 B2 | 1/2015 | Turkel et al. |
| 8,940,308 B2 | 1/2015 | Turkel et al. |
| 8,968,747 B2 | 3/2015 | Turkel et al. |
| 9,061,025 B2 | 6/2015 | Burstein et al. |
| 9,067,025 B2 | 6/2015 | Fini |
| 9,078,892 B2 | 7/2015 | Turkel et al. |
| 9,078,893 B2 | 7/2015 | Turkel et al. |
| 9,279,001 B2 | 3/2016 | Turkel et al. |
| 9,555,085 B2 | 1/2017 | Turkel et al. |
| 9,764,011 B2 | 9/2017 | Turkel et al. |
| 9,827,297 B2 | 11/2017 | Blumenfeld |
| 9,943,576 B2 | 4/2018 | Forssen et al. |
| 10,034,923 B2 | 7/2018 | Brin |
| 10,092,631 B2 | 10/2018 | Turkel et al. |
| 10,111,938 B2 | 10/2018 | Blumenfeld et al. |
| 10,119,638 B2 | 11/2018 | Pa et al. |
| 10,201,487 B2 | 2/2019 | Behler et al. |
| 10,220,079 B2 | 3/2019 | Blumenfeld |
| 10,259,877 B2 | 4/2019 | Sun et al. |
| 10,406,213 B2 | 9/2019 | Turkel et al. |
| 10,519,224 B2 | 12/2019 | Bigal et al. |
| 10,603,366 B2 | 3/2020 | Turkel et al. |
| 10,729,751 B2 | 8/2020 | Blumenfeld et al. |
| 10,874,722 B2 | 12/2020 | Blumenfeld |
| 11,033,610 B2 | 6/2021 | Turkel et al. |
| 2003/0224019 A1 | 12/2003 | O'Brien |
| 2004/0009180 A1 | 1/2004 | Donovan |
| 2004/0028706 A1 | 2/2004 | Aoki et al. |
| 2004/0115139 A1 | 6/2004 | Katz et al. |
| 2004/0213811 A1 | 10/2004 | Ackerman |
| 2004/0219172 A1 | 11/2004 | Voet |
| 2005/0123567 A1 | 6/2005 | First |
| 2005/0147625 A1 | 7/2005 | First |
| 2005/0191320 A1 | 9/2005 | Turkel et al. |
| 2005/0191321 A1 | 9/2005 | Turkel et al. |
| 2005/0238664 A1 | 10/2005 | Hunt |
| 2005/0238667 A1 | 10/2005 | Hunt |
| 2006/0018844 A1 | 1/2006 | Katz et al. |
| 2006/0104995 A1 | 5/2006 | Turkel et al. |
| 2006/0121057 A1 | 6/2006 | Turkel et al. |
| 2006/0171963 A1 | 8/2006 | Blumenfeld |
| 2007/0009555 A1 | 1/2007 | Borodic |
| 2007/0202129 A1 | 8/2007 | Aoki et al. |
| 2008/0021437 A1 | 1/2008 | Boyd |
| 2008/0033318 A1 | 2/2008 | Mace et al. |
| 2008/0213315 A1 | 9/2008 | Hunt |
| 2009/0232850 A1 | 9/2009 | Manack et al. |
| 2009/0304748 A1 | 12/2009 | Hunt |
| 2010/0189655 A1 | 7/2010 | Turkel et al. |
| 2010/0266638 A1 | 10/2010 | Turkel et al. |
| 2010/0272754 A1 | 10/2010 | Walker |
| 2011/0200639 A1 | 8/2011 | Blumenfeld |
| 2012/0053126 A1 | 3/2012 | Turkel et al. |
| 2012/0189610 A1 | 7/2012 | Foster et al. |
| 2012/0237548 A1 | 9/2012 | Hunt |
| 2013/0150307 A1 | 6/2013 | Turkel et al. |
| 2013/0189354 A1 | 7/2013 | Singh |
| 2013/0224180 A1 | 8/2013 | Turkel et al. |
| 2013/0236446 A1 | 9/2013 | Binder |
| 2013/0251830 A1 | 9/2013 | Manack et al. |
| 2013/0296259 A1 | 11/2013 | Hunt |
| 2013/0315890 A1 | 11/2013 | Binder |
| 2013/0330321 A1 | 12/2013 | Turkel et al. |
| 2014/0030248 A1 | 1/2014 | Turkel et al. |
| 2014/0044695 A1 | 2/2014 | Hunt |
| 2014/0079687 A1 | 3/2014 | Blumenfeld |
| 2014/0099294 A1 | 4/2014 | Dolly et al. |
| 2014/0105882 A1 | 4/2014 | Taylor |
| 2014/0199288 A1 | 7/2014 | Hunt |
| 2014/0205590 A1 | 7/2014 | Blumenfeld |
| 2014/0212456 A1 | 7/2014 | Vazquez-Cintron et al. |
| 2014/0294803 A1 | 10/2014 | Turkel et al. |
| 2014/0303124 A1 | 10/2014 | Burstein et al. |
| 2014/0330248 A1 | 11/2014 | Thompson-Nauman et al. |
| 2014/0343041 A1 | 11/2014 | Chapin et al. |
| 2015/0174217 A1 | 6/2015 | Dolly et al. |
| 2015/0258183 A1 | 9/2015 | Borodic |
| 2016/0074485 A1 | 3/2016 | Turkel et al. |
| 2016/0175409 A1 | 6/2016 | Turkel et al. |
| 2016/0263202 A1 | 9/2016 | Blumenfeld et al. |
| 2017/0128552 A1 | 5/2017 | Turkel et al. |
| 2017/0224786 A1 | 8/2017 | Hunt |
| 2018/0028624 A1 | 2/2018 | Turkel et al. |
| 2018/0078622 A1 | 3/2018 | Blumenfeld |
| 2019/0038726 A1 | 2/2019 | Turkel et al. |
| 2019/0060423 A1 | 2/2019 | Blumenfeld et al. |
| 2019/0183785 A1 | 6/2019 | Edelson et al. |
| 2019/0240299 A1 | 8/2019 | Blumenfeld |
| 2019/0256607 A1 | 8/2019 | Sun et al. |
| 2020/0000892 A1 | 1/2020 | Turkel et al. |
| 2020/0030415 A1 | 1/2020 | Blumenfeld et al. |
| 2020/0230217 A1 | 7/2020 | Turkel et al. |

FOREIGN PATENT DOCUMENTS

| | | |
|---|---|---|
| WO | WO-2003/011333 A1 | 2/2003 |
| WO | WO-2004/035011 A2 | 4/2004 |
| WO | WO-2005/082339 A2 | 9/2005 |
| WO | WO-2006/078588 A2 | 7/2006 |
| WO | WO-2011/030370 A1 | 3/2011 |
| WO | WO-2011/123456 A1 | 10/2011 |
| WO | WO-2014/130581 A | 8/2014 |

OTHER PUBLICATIONS

Aoki KR. Evidence for antinociceptive activity of botulinum toxin type A in pain management. Headache 2003; 43 Suppl 1:S9-15.

Aoki KR. Pharmacology and immunology of botulinum toxin serotypes. J Neurol 2001;248 Suppl 1:1,3-1,10.

Aoki, K., et al., Botulinum toxin type A and other botulinum toxin serotypes: a comparative review of biochemical and pharmacological actions, Eur J. Neurol 2001: (suppl 5); 21-29.

Aoki, K., Physiology and pharmacology of therapeutic botulinum neurotoxins, in Kreyden, O., editor, Hyperhydrosis and botulinum toxin in dermatology, Basel, Karger; 2002; 30: pp. 107-116, at 109-110.

Aurora et al., OnabotulinumtoxinA for Treatment of Chronic Migraine: Results From the Double-Blind, Randomized, Placebo-controlled . . . , Cephalalgia, Jan. 1, 2010, 793-803, 30 (7).

Bakheit, A M O, The Beneficial Antispasticity Effect of Botulinum Toxin Type A is Maintained After Repeated Treatment Cycles, J Neurol Neurosurg Psychiatry, Nov. 2004, 1558-1561, 75(11), US.

Bhattacharya K., et al., Novel uses of botulinum toxin type A: two case reports, Mov Disord 2000; 15(Suppl 2):51-52.

Bigal ME, Sheftell FD, Rapoport AM, et al. Chronic daily headache in a tertiary care population: correlation between International Headache Society diagnostic criteria and proposed revisions of criteria for chronic daily headache. Cephalalgia 2002; 22:432-438.

Bigalke H., et al., Botulinum A Neurotoxin Inhibits Non-Cholinergic Synaptic Transmission in Mouse Spinal Cord Neurons in Culture, Brain Research 360;318-324:1985.

Bigalke H., et al., Tetanus Toxin and Botulinum A Toxin Inhibit Release and Uptake of Various Transmitters, as Studied with Particulate Preparations From Rat Brain and Spinal Cord, Naunyn-Schmiedeberg's Arch Pharmacol 316;244-251:1981.

(56) References Cited

OTHER PUBLICATIONS

Binder WJ, Brin MF, Blitzer A. Botulinum toxin type A (Botox) for treatment of migraine headaches: an open-label study. Otolaryngol Head Neck Surg 2000;123(6):669-676.
Binz T. et al., The Complete Sequence of Botulinum Neurotoxin Type A and Comparison with Other Clostridial Neurotoxins, J Biological Chemistry 265(16);9153-9158:1990.
Blugerman G., et al., Multiple eccrine hidrocystomas: A new therapeutic option with botulinum toxin, Dermatol Surg May 2003;29(5):557-9.
Blumenfeld (Headache, 2002; 42:420, Abstract F20).
Blumenfeld A, "Botulinum toxin type a as an effective prophylactic treatment in primary headache disorders", Headache, Sep. 2003 US, vol. 43, No. 8, ISSN 0017-8748, pp. 853-860, XP002722397.
Blumenfeld AM, Dodick DW, Silberstein SD. Botulinum neurotoxin for the treatment of migraine and other primary headache disorders. Dermatol Clin 2004;22:167-175.
Blumenfeld, et al., Method of Injection of OnabotulinumtoxinA for Chronic Migraine . . . , Headache 2010, Oct. 1, 2010, 1406-1418, 50 (9), Wiley Periodicals Inc.
BPAI Board Decision, Ex parte Catherine C. Turkel and Mitchell F. Brin, Appeal 2010-011228, U.S. Appl. No. 11/039,506, Technology Center 1600.
Brandes JL, Saper JR, Diamond M, et al. Topiramate for migraine prevention: a randomized controlled trial. JAMA;2004;291 :965-973.
Brashear, Allison, et al., An Open-Label Trial Of Botulinum Toxin Type B In Upper Limb Spasticity, Archives Of Physical Medicine And Rehabilitation, Sep. 2001, 2 Pages, 82 (9), US.
Brem, H., et al., Placebo-Controlled Trial of Safety and Efficacy of Intraoperative Controlled Delivery by Biodegradable Polymers of Chemotherapy for Recurrent Gliomas, Lancet 345:1008-1012:1995.
Brin et al, Toxicon 54 (2009) 668-674. available online: Feb. 7, 2009.
Brin et al, Toxicon 54 (2009) 676-682. available online: Mar. 31, 2009.
Brin et al., Report of the Therapeutics and Technology Assessment Subcommittee of the American Academy of Neurology, Neurology, 40: 1332-1336, 1990.
Brin MF, Fahn S, Moskowitz C, et al. Localized injections of botulinum toxin for the treatment of focal dystonia and hemifacial spasm. Movement Dis 1987;2:237-254.
Brin MF, Swope DM, O'Brien C, et al. Botox® for migraine: double-blind, placebo-controlled, region-specific evaluation. Cephalalgia 2000;20:421-422.
Brin, M., et al., Botulinum toxin type A: pharmacology, in Mayer N., editor, Spasticity: etiology, evaluation, management and the role of botulinum toxin, 2002; pp. 110-124, at 112-113.
Bushara K., Botulinum toxin and rhinorrhea, Otolaryngol Head Neck Surg 1996;114(3):507.
Cairns et al, "Botulinum neurotoxin A for chronic migraine headaches: does it work and how?" Pain Manag., 2014, 4/6:377-380.
Cao, Y., et al. Functional MRI of chronic daily headache. Cephalalgia 1999;19:462-463.
Carruthers et al., "Improvement of Tension-Type Headache When Treating Wrinkles With Botulinum Toxin A Injections", Headache, 1999, 39:662-665.
Castillo JP, Munoz P, Guitera V, et al. Epidemiology of chronic daily headache in the general population. Headache 1999;39:190-196.
Cattin, The New Zealand Medical Journal, May 16, 2003, 116/1174:3 pages.
Cheshire WP, Abashian SW, Mann JD. Botulinum toxin in the treatment of myofascial pain svndrome. Pain 1994;59:65-69.
Colas R, Munoz P, Temprano R, et al. Chronic daily headache with analgesic overuse: epidemiology and impact on quality of life. Neurology 2004;62:1338-1342.
Conidi, Curr. Pain Headache Rep., 2016, 20:40, 8 pages.
Couch JR. Placebo effect and clinical trials in migraine therapy. Meth Prob Migraine Trials, Neuroepid 1987;6: 178-185.

Cui M, Khanijou S, Rubino J, et al. Subcutaneous administration of botulinum toxin A reduces formalin-induced pain. Pain 2004; 107: 125-133.
Cui M., et al., Mechanisms of the antinociceptive effect of subcutaneous Botox®: inhibition of peripheral and central nociceptive processing, Naunyn Schmiedebergs Arch Pharmacol 2002; 365 (supp 2): R17.
Dabrowski et al.; Botulinum toxin as a novel treatment for self mutilation in Lesch-Nyhan syndrome, Ann Neurol Sep. 2002;52(3 Supp 1):S157.
Delstanche et al Acta Neurol. Belg, 2010, 110:221-229.
Depakote® ER (package insert). Abbott Laboratories; 2003.
Diener et al (Cur Med Res Opin 17(1 s): s17-s21, 2001.
Diener et al, European Journal of Neurology 2014, 21: 851-859.
Diener HC, et al., OnabotulinumtoxinA for Treatment of Chronic Migraine: Results From . . . , Cephalalgia, Jan. 1, 2010, 804-814, 30 (7), Sage.
Dodick, David W. et al., OnabotulinumtoxinA for Treatment of Chronic Migraine: Pooled Results from the Double-Blind, Randomized, Placebo-Controlled Phases of the PREEPT Clinical Program, Headache, 2010, 921-936, vol. 50, No. 6, US.
Dolman, C.E. et al, Human Botulism in Canada, CMA Journal, 1974, 191-200, 110.
Dowson, A.J., et al., Managing Chronic Headaches in the Clinic, Int J. Clin Pract., Dec. 2004,58, 12,DD. 1142-1151.
Duggan et al.; A survey of Botulinum neurotoxin substrate expression in cells; Mov Disord, 10(3):376:1995.
Durham et al, "Insights into the Mechanism of OnabotulinumtoxinA in Chronic Migraine", Headache: The Journal of Head and Face Pain, Nov./Dec. 2011, 51/10:1573-1577.
Durham PL, Cady Ryan, Cady Roger. Regulation of calcitonin gene-related peptide secretion from trigeminal nerve cells by botulinum toxin type A: implications for migraine therapy. Headache 2004;44:35-43.
Edwards, K.R., et al., Botulinum Toxin Type A (Botox) for Chronic Daily Headaches, Headache, May 2002, 429 S136, 42(5).
Emer et al. "Injectable neurotoxins and fillers: There is no free lunch", Clinics in Dermatology 2011, vol. 29, pp. 678-690.
Eross, Daily Headaches Due To Medication Overuse, Neurology, May 2003, 60(10), E8-9.
European Agency for the Evaluation of Medicinal Products. Note for guidance on clinical investigation of medicinal products for the treatment of migraine. Dec. 2003.
Extended European Search Report for EP Application No. 11194257.9, dated Jan. 23, 2012.
Extended European Search Report for EP Application No. 14156327.0, dated Apr. 9, 2014.
Extended European Search Report for EP Application No. 14163033.5, dated May 8, 2014.
Extended European Search Report for EP Application No. 17189376.1, dated Mar. 23, 2018.
Extended European Search Report for EP Application No. 22184142.2, dated Jan. 16, 2023.
Farinelli I et al, "Long-term benefits of botulinum toxin type A (Botox) in chronic daily headache: a five-year long experience", The Journal of Headache and Pain ; Official Journal of the Italian Society for the Study of Headaches, Springer-Verlag, MI, (Dec. 10, 2006), vol. 7, No. 6, doi:10.1007/S10194-006-0344-9, ISSN 1129-2377, pp. 407-412, XP019462906.
Finzi E et al, "Treatment of depression with botulinum toxin A: A case series", Dermatologic Surgery, Wiley-Blackwell Publishing, Inc, New York, US, (Jan. 1, 2006), vol. 32, No. 5, doi:10.1111/J.1524-4725.2006.32136.X, ISSN 1076-0512, pp. 645-649, XP009074681.
Foster L, Clapp L, Erickson M, Jabbari B. Botulinum toxin A and chronic low back pain. A randomized, double-blind study. Neurol 2001;56:1290-1293.
Freund BJ, Schwartz M. Use of botulinum toxin in chronic whiplash-associated disorder. Clin J Pain 2002;18(6 Suool):S163-S168.
Frevert et al, Biologies: Targets & Therapy, 2010:4 325-332.

(56) References Cited

OTHER PUBLICATIONS

Fung L. K. et al., Pharmacokinetics of Interstitial Delivery of Carmustine 4-Hydroperoxycyclophosphamide and Paclitaxel From a Biodegradable Polymer Implant in the Monkey Brain, Cancer Research 58;672-684:1998.
Gady et al. Connecticut Medicine, Mar. 2013, 77/3:165-166.
Gladstone JP., Gawel M. Newer formulations of the triptans: advances in migraine management, Drugs. 2003; 63(21):2285-305.
Gladstone, J., et al., Chronic Daily Headache: A Rational Approach to a Challenging Problem, Seminars in Neurology, 2003, vol. 23, No. 3, pp. 265-275.
Gonelle-Gispert et al.; snap-25a and -25b isoforms are both expressed in insulin-secreting cells and can function in insulin secretion; Biochem J 1;339 (pt 1):159-65:1999.
Guyton A.C. et al., Textbook of Medical Physiology, W.B. Saunders Company 1996, ninth edition; 685-697.
Guyuron et al, Plastic and Reconstructive Surgery, Jun. 2002, 109/7:2183-2189.
Habermann E., et al., Tetanus Toxin and Botulinum A and C Neurotoxins Inhibit Noradrenaline Release From Cultured Mouse Brain, J Neurochem 51(2);522-527:1988.
Habermann E., Inhibition by Tetanus and Botulinum A Toxin of the release of [3H]Noradrenaline and [3HJGABA From Rat Brain Homogenate, Experientia 44;224-226: 1988.
Habermann, I-Labeled Neurotoxin from Clostridium botulinum A: Preparation, Binding to Synaptosomes and Ascent to the Spinal Cord; Nauyn-Schmiedeberg's Arch. Pharmacol. 1974; 281, 47-56.
Harrison's Principles of Internal Medicine (1998), edited by Anthony Fauci et al., 14th edition, published by McGraw Hill.
Headache Classification Committee of the International Headache Society. Classification and diagnostic criteria for headache disorders, cranial neuralgias and facial pain. Cephalalgia 1988;8 Suppl 7: 1-96.
Heckmann et al, "Letter: Botulinum Toxin Overrides Depression: Not Surprising, yet Sensational", Dermatologic Surgery, (Jun. 1, 2007), vol. 33, No. 6, doi:10.1111/j.1524-4725.2007.33160.x, ISSN 1076-0512, pp. 765-765, XP055003857.
Heckmann M., et al., Botulinum toxin type A injection in the treatment of lichen simplex: An open pilot study, J Am Acad Dermatol Apr. 2002;46(4):617-9.
Hering R, Gardiner I, Catarci T, Witmarch T, Steiner T, de Belleroche J. Cellullar adaptation in migraineurs with chronic daily headache. Cephalalgia 1993;13:261-6.
Hexsel, Doris, et al., Fields of Effects of 2 Commercial Preparations of Botulinum Toxin Type A at Equal Labeled Unit Doses, A Double-Blind Randomized Trial, Fields of Effects of 2 Commercial Preparations of Botulinum Toxin Type A at Equal Labeled Unit Doses, A Double-Blind Randomized Trial, Oct. 9, 2013, E1-E6, DOI: 10.1001/jamadermatol.2013.6440, JAMA Dermatology.
International Preliminary Report on Patentability for International Application No. PCT/US05/04778, dated Jan. 20, 2006.
International Preliminary Report on Patentability for International Application No. PCT/US06/01432, dated Jul. 24, 2007.
International Preliminary Report on Patentability for International Application No. PCT/US11/30370, dated Oct. 2, 2012.
International Preliminary Report on Patentability for International Application No. PCT/US16/21998, dated Sep. 19, 2017.
International Search Report and Written Opinion for International Application No. PCT/US05/04778, dated Aug. 26, 2005.
International Search Report and Written Opinion for International Application No. PCT/US06/01432, dated Nov. 24, 2006.
International Search Report and Written Opinion for International Application No. PCT/US11/30370, dated Jul. 12, 2011.
International Search Report and Written Opinion for International Application No. PCT/US16/21998, dated May 23, 2016.
Jabbari, Nature Clinical Practice Neurology, Dec. 2008, 4/12:676-685.
Jacks, L., et al., Idiopathic toe walking: Treatment with botulinum toxin A injection, Dev Med Child Neurol 2002;44(Suppl 91 ):6.
Jackson et al, JAMA. 2012;307(16):1736-1745.
Jahanshahi M., et al., Psychological functioning before and after treatment of torticollis with botulinum toxin, J Neurol Neurosurg Psychiatry 1992; 55(3): 229-231.
Jankovic J. et al., Therapy With Botulinum Toxin, Marcel Dekker, Inc., (1994), pp. 5, 150.
Johnson, Eric, Clostridial Toxins as Therapeutic Agents: Benefits of Nature's Most Toxic Proteins, Annu Rev Microbiol, 1999, 551-575, 53.
Jost W., Ten years' experience with botulinum toxin in anal fissure, Int J Colorectal Dis Sep. 2002;17(5):298-302.
Katsambas A., et al., Cutaneous diseases of the foot: Unapproved treatments, Clin Dermatol Nov.-Dec. 2002;20(6):689-699.
Katsarava et al (Neurology, May 27, 2003, vol. 60, No. 10, pp. 1682-183).
Klapper et al: "A multicenter, double-blind, placebo-controlled trial of two dosages of Botox (Botulinum Toxin, Type A) in the prophylactic treatment of migraine." Headache, May 1999, pp. 361-362, p. 361 col. 2, paragraph 5-8, p. 362, col. 1, paragraph 1-3.
Klapper JA, Mathew NT, Klapper A et al. Botulinum toxin type A (BTX-A) for the prophylaxis of chronic daily headache. Cephalalgia 2000;20:292-293.
Lew, Mark F. et al., The Safety And Efficacy Of Botulinum Toxin Type B In The Treatment Of Patients With Cervical Dystonia: Summary of Three Controlled Clinical Trials, Neurology 2000, 2000, 29-35, 55 (12 Suppl 5), US.
Li Y, et al., Sensory and motor denervation influences epidermal thickness in rat foot glabrous skin, Exp Neurol 1997;147:452-462 (see p. 459).
Linde M, Limmroth V, Dahlof C, on behalf of the Headache Masters Programme. Ethical aspects of placebo in migraine research. Cephalalgia 2003;23:491-495.
Linton-Dahlof, M Linde, Dahlof C. Withdrawal therapy improves chronic daily headache associated with long-term misuse of headache medication: a retrospective study. Cephalalgia 2000;20:658-662.
Lipton et al, Neurology, 2011, 77:1465-1472.
Lipton RB, Bigal ME. Chronic daily headache: is analgesic overuse a cause or a consequence? Neurology 2003;61:154-155.
Lipton RB, Stewart WF. Migraine headaches: epidemiology and comorbidity. Clin Neuroscience 1998;5:2-9.
Liu et al, J Chin Med Assoc., Dec. 2007, 70(12):535-540.
Loder, E., et al., Use of Botulinum Toxins for Chronic Headaches: A Focused Review, The Clinical Journal of Pain, 2002, 18, pp. S169-S176.
Luvisetto et al, Toxins 2015, 7:3818-3844. published:Sep. 23, 2015.
Maizels, M., et al., The Patient with Daily Headaches, American Family Physician, Dec. 2004, vol. 70, No. 12, oo. 2299-2306.
Manzoni GC, Granella F, Sandrini G, et al. Classification of chronic daily headache by International Headache Society criteria: limits and new proposals. Cephalalgia 1995;15:37-43.
Marjama-Lyons, J., et al., Tremor-Predominant Parkinson's Disease, Drugs & Aging 16(4);273-278:2000.
Mathew et al: "A multicenter, double-blind placebo-controlled trial of two dosages of Botox (Botulinum Toxin, Type A) in the prophylactic treatment of migraine." Cephalalgia May 1999, p. 319.
Mathew N, Kaup A, Kailasam J. botulinum toxin type A modifies chronic migraine further long-term (3years) experience with up to ten sets of treatments. Headache 2003;43:576.
Mathew NT, Reuveni U, Perez F. Transformed or evolutive migraine Headache 1987;27:102-106.
Mathew, et al., Botulinum Toxin Type A (Botox) for the Prophylactic, Headache, Apr. 2005, 293-307, 45 (4).
Mathew, N. Kailasam, J., Disease Modification Migraine with Botulinum Toxin Type A: Long Term Experience, 2002, Cephalalgia, 22(7):609, Abstract.
Mathew, N. Kailasam, J., "Disease Modification' Migraine with Botulinum Toxin TypeA : Long Term Experience", Headache 2002, 42(5):454, Abstract S107.
Mathew, N. Kaup, A., The Use of Botulinum Toxin Type A in Headache Treatment, 2002, 365-373.
Mauskop A. Botulinum toxin in the treatment of chronic daily headaches. Cephalalgia 1999; 19:453.

(56) References Cited

OTHER PUBLICATIONS

Miller, T., Retrospective Cohort Analysis of 48 Chronic Headache Patients Treated with Botulinum Toxin Type A (Botox) in a Combination Fixed Injection Site and Follow-the-Pain Protocol, Headache, May 2002, 430-431 S138, 42(5).
Monzon MJ, Lainez MJA. Quality of life in migraine and chronic daily headache patients. Cephalalgia 1998; 18:638-643.
Moyer E et al., Botulinum Toxin Type B: Experimental and Clinical Experience, being chapter 6, pp. 71-85 of "Therapy With Botulinum Toxin", edited by Jankovic, J. et al. (1994), Marcel Dekker, Inc.
Muller, Wissel J., et al., Management of spasticity associated pain with botulinum toxin A. J Pain Symptom Manage 2000;20:44-9.
Murry T., et al., Spasmodic dysphonia; emotional status and botulinum toxin treatment, Arch Otolaryngol Mar. 1994; 120(3): 310-316.
Naumann et al; Botulinum toxin type A in the treatment of focal, axillary and palmar hyperhidrosis and other hyperhidrotic conditions; European J. Neurology 6 (Supp 4): S111-S115:1999.
Naumann, M., et al., Botulinum Toxin for Focal Hyperhidrosis: Technical considerations And Improvements in Application, British Journal of Dermatology, Dec. 1998, 1111-1137, 139 (6), US.
O'Brien PC, Fleming TR. A multiple testing procedure for clinical trials. Biometrics 1979;35:549-556.
O'Day, Current Opinion in Ophthalmology 2001, 12:419-422.
Ondo WG, Vuong KO, Derman HS. Botulinum toxin A for chronic daily headache: a randomized, placebo-controlled, parallel design study. Cephalalgia 2004;24:60-5.
Ondo, W.G. et al., Botulinum Toxin A for Chronic Daily Headache: A 60-Patient, Randomized, Placebo-Controlled, Parallel Design Study, Headache, May 2002, 431 S131, 42(5).
Padberg et al Cephalalgia, 2004, 24:675-680.
Pearce, L.B., Pharmacologic Characterization of Botulinum Toxin for Basic Science and Medicine, Toxicon 35(9);1373-1412 at 1393.
Porta et al, J. Headache Pain, (2005) 6:325-327. published online: Jul. 20, 2005.
Purkiss J, Welch M, Doward S, et al. Capsaicin-stimulated release of substance P from cultured dorsal root ganglion neurons: involvement of two distinct mechanisms. Biochem Pharmacol 2000;59:1403-1406.
Rabasseda et al., Toxicon, 26:329-326, 1988.
Ragona, et al.; Management of Parotid Sialocele With Botulinum Toxin, The Laryngoscope 109:1344-1346:1999.
Rahimtoola H, Buurma H, Tijssen CC, et al. Migraine prophylactic medication usage patterns in The Netherlands. Cephalalgia 2003;23:293-301.
Ranoux et al, The Journal of Headache and Pain (2017) 18:75, 8 pages.
Ravenni, Roberta, et al., Conversion Ratio Between Dysport and Botox in Clinical Practice: An Overview of Available Evidence, Neurol Sci, DOI: 10.1007/s10072-013-1357-1, Springer-Verlag Italia, Apr. 11, 2013.
Relja et al, Journal Neurology, (2004), 251 (Suppl 1 ): 1/12-1/14.
Relja G, Granato A, Maria Antonello R, Zorzon M. Headache induced by chronic substance use: analysis of medication overused and minimum dose required to induce headache, Headache. Feb. 2004;44(2):148-53.
Robertson et al, Neuropsychiatric Disease and Treatment, (2012) vol. 8, pp. 35-48.
Rogers J., et al., Injections of botulinum toxin A in foot dystonia, Neurology Apr. 1993;43(4 Suppl 2).
Ruffion, Alain, et al., What Is The Optimum Dose Of Type A Botulinum Toxin For Treating Neurogenic Bladder Activity, British Journal Of Urology International, 2006, 1030-1034, 97 (5), US.
Sanchez-Prieto, J., et al., Botulinum Toxin A Blocks Glutamate Exocytosis From Guinea Pig Cerebral Cortical Synaptosomes, Eur J. Biochem 165:675-681:1897.
Saper JR, Lake AE III, Cantrell DT, et al. Chronic daily headache prophylaxis with tizanidine: a double-blind, placebo-controlled, multicenter outcome study. Headache 2002;42:470-482.
Schantz, E.J., et al, Properties and use of Botulinum toxin and Other Microbial Neurotoxins in Medicine, Microbial Rev. 56;80-99:1992.
Scher AI, Stewart WF, Liberman J, et al. Prevalence of frequent headache in a population sample. Headache 1998;38:497-506.
Schim et al., Effect Of Preventative Treatment with Botulinum Toxin Type A On Acute Headache Medication Usage In Migraine Patients, Current Medical Research And Opinion, 2004, 49-53, 20 (1), US.
Schnider et al, J Headache Pain, (2002) 3:93-99.
Schulte-Mattler et al, Eur J Neurol. Feb. 2006; Suppl 1:54-4.
Schulte-Mattler et al, Pain 109 (2004) 110-112.
Schwartz BS, Stewart WF, Lipton RB. Loss of workdays and decreased work effectiveness associated with headache in the workplace. J Occup Environ Med 1997;39:320-327.
Sevim, S., et al., Botulinum toxin-A therapy for palmar and plantar hyperhidrosis, Acta Neurol Belg Dec. 2002;102(4):167-70.
Siegel S. Non-parametric statistics for the behavioral sciences. New York: McGraw-Hill Book Company, 1956:96:116-127.
Silberstein et al. "Botulinum toxin type A in the prophylactic treatment of chronic tension-type headache: a multicentre, double-blind, randomized, placebo-controlled, parallel-group study", Cephalalgia, 2006, 26:790-800.
Silberstein et al., "Botulinum toxin type A for the prophylactic treatment of chronic daily headache: a randomized, double-blind, placebo-controlled trial.", Mayo Clinic Proceedings. Mayo Clinic Sep. 2005 LNKD-Pubmed:16178492, vol. 80, No. 9, Sep. 2005 (Sep. 2005), pp. 1126-1137.
Silberstein SD, Lipton RB, Sliwinski M. Classification of daily and near-daily headaches: field trial of revised IHS criteria. Neurology 1996;47:871-875.
Silberstein SD, Lipton RB, Solomon S, Mathew NT. Classification of daily and near-daily headaches: proposed revisions to the IHS criteria. Headache 1994;34:1-7.
Silberstein SD, Lipton RB. Chronic daily headache, including transformed migraine, chronic tension-type headache, and medication overuse. In: Silberstein SD, Lipton RB, Dalessio DJ, eds. Wolff's headache and other head pain, 7th ed. New York, NY: Oxford University Press;2001 :247-282.
Silberstein SD, Lipton RB. Chronic daily headache. Curr Opin Neurol 2000; 13:277-283.
Silberstein SD, Neto W, Schmitt J, et al. Topiramate in migraine prevention. Arch Neurol 2004;61 :490-495.
Silberstein SD, Silberstein MM. New concepts in the pathogenesis of headache. Part III. Pain Man 1990;3:334-342.
Silberstein, et al: "Botulinum Toxin Type A as a Migraine Prevention Treatment" Headache Jun. 2000, pp. 445-450.
Silberstein, Expert Opinion on Pharmacotherapy, 2001, 2: 10, 1649-1654.
Silberstein, S., et al., Drug Overuse and Rebound Headache, Current Pain and Headache Reports, 2002, 240-247, 6.
Silvestrini M, Bartolini M, Coccia M, et al. Topiramate in the treatment of chronic miaraine. Ceohalalaia 2003;23:820-824.
Simeoni, S., et al., Stress Hormones In Chronic Migraine Are Modulated By Botulinum Toxin-Type A, Pharmacoloqyonline, 2006, 720-728, 3, US.
Simpson et al. Pharmacol. Rev. 33:155-188, 1981.
Singh, Critical Aspects of Bacterial Protein Toxins, pp. 63-84 (chapter 4) of Natural Toxins II, edited by B.R. Singh et al., Plenum Press, New York (1996).
Sloop RR, Cole BA, Escutin RO. Reconstituted botulinum toxin type A does not lose potency in humans if it is refrozen or refrigerated for 2 weeks before use. Neurology. Jan. 1997;48(1):249-53.
Smuts JA, Baker MK, Smuts HM, et al. Prophylactic treatment of chronic tension-type headache usina botulinum toxin type A. Eur J Neurol 1999;6(Suool 4):S99-S102.
Solomon GD, Sokbieranda FG, Genzen JR. Quality of life assessment among migraine patients treated with Sumatriptan. Headache 1995;35:449-454.
Spira PJ, Beran RG. Gabapentin in the prophylaxis of chronic daily headache: a randomized, placebo-controlled study. Neuroloav 2003;61: 1753-1759.

(56) References Cited

OTHER PUBLICATIONS

Stewart WF, Lipton RB, Celentano DD, et al. Prevalence of migraine headaches in the United States. Relation to age, income, race and other sociodemographic factors. JAMA 1992;267:64-69.
Suputtitada, A., Local botulinum toxin type A injections in the treatment of spastic toes, Am J Phys Med Rehabil Oct. 2002;81(10):770-5.
Suzuki, Kosuke et al., Botulinum Toxin Type A for Migraine Prophylaxis in the Japanese Population: An open-Label Prospective Trial, Internal Medicine, 2007, vol. 46, No. 13, p. 959-963.
Tepper and Dodick, Debate: Analgesic overuse is a cause, not a consequence, of chronic daily headache, Headache, 2002; 42:543-554.
Tepper et al (Cephalagia, 2003, 23, 581-762).
Tepper et al., "Botulinum Neurotoxin Type A in the Preventative Treatment of Refractory Headache: A Review of 100 Consecutive Cases", Headache 2004, 44, pp. 794-800.
Tepper, S., et al., Botulinum Toxin Type A in the Preventive Treatment of Refractory Headaches—Comparison Between Medication Overusers and Nonmedication Overusers Groups, Cephalalgia, 2003, 23, p. 715, poster P5N86.
Troost BT. Botulinum toxin type A (Botox) in the treatment of migraine and other headaches. Expert Rev Neurotherap 2004;4:27-31.
Vadoud-Seyedi, J., et al., Treatment Of Plantar Hyperhidrosis With Dermojet Injections Of Botulinum Toxin, Dermatology 2000; 201: 178 (1 Page).
Wang SJ, et al. Chronic daily headache in Chinese elderly: prevalence, risk factors and biannual follow-up. Neurology 2000;54:314-319.
Wang SJ, et al. Quality of life differs among headache diagnoses: analysis of SF-36 survey in 901 headache patients. Pain 89 (2001): 285-292.
Weigand et al.; I-Labelled Botulinum A Neurotoxin: Pharmacokinetics in Cats after Intramuscular Injection; Naunyn-Schmiedeberg's Arch. Pharmacol. 1976; 292, 161-165.
Welch KM, Goadsby PJ. Chronic daily headache: nosology and pathophysiology. Curr Opin Neurol 2002; 15:287-295.
Winner, "Botulinum toxins in the treatment of migraine and tension-type headaches", Phys Med Rehabil Clin Am. 2003, 14:885-899.
Wissel J, Muller J, Dressnandt J, Heinen F, Naumann M, Topka H, Poewe W. Management of spasticity associated pain with botulinum toxin A. J Pain Symptom Manage 2000;20:44-9.
Woolf C. et al., Neuropathic Pain: Aetiology, Symptoms, Mechanisms, and Management, Lancet 1999; 353: 1959-64.
Begasse De Dhaem et al: "Modifications to the Preempt Protocol for OnabotulinumtoxinA Injections for Chronic Migraine in Clinical Practice", Headache, vol. 60, No. 7, Apr. 25, 2020 (Apr. 25, 2020), pp. 1365-1375.
Blumenfeld et al., "Procedures for Administering Botulinum Toxin Type A for Migraine and Tension-type Headache", Headache, vol. 43, No. 8, Aug. 27, 2003, pp. 884-891.
Aurora et al., Acta Neural Scand 2014: 129: 61-70 DOI: 10.1111/ane. 12171. (Year: 2014).
Aurora, Expert Opin. Pharmacother. (2006) 7(8):1085-1095 (Year: 2006).
Binder et al., Dis Mon., May 2002, 48:323-335.
BOTOX® (package insert). Irvine, California: Allergan Inc; 2004.
Burstein et al. "Mechanism of Action of OnabotulinumtoxinA in Chronic Migraine: A Narrative Review", Headache: The Journal of Head and Face Pain, 14 pages. publication date: Jun. 2020.
Elashoff JD, nQuery Advisor Version 5.0 User's Guide, Los Angeles, 2002.
Elkind, Arthur H.; O'Carroll, Philip; Blumenfeld, Andrew; DeGryse, Ronald; Dimitrova, Rozalina, Journal of Pain (2006), 7(10), 688-696 (abstract only) (Year: 2006).
Headache Classification Subcommittee of the International Headache Society. The international classification of headache disorders, 2nd ed. Cephalalgia 2004;24 Suppl 1:1-151.
Holroyd KA, Stensland M, Lipchik GL, et al. Psychosocial correlates and impact of chronic tension-type headaches. Headache 2000; 40:3-16.
International Headache Society committee on Clinical Trials in Migraine. Guidelines for controlled trials of drugs in migraine. First edition. Cephalalgia 1991; 11 :1-12.
Katsarava et al., Curr. Pain Headache Rep., 2012, 16:86-92. published online: Nov. 15, 2011 (Year: 2012).
Klapper, Headache Quarterly, 1999, 10/2:141-143.
Tepper, Steward J., Botulinum Neurotoxin Type A in the Preventive Treatment of Refractory Headache, A Review of 100 Consecutive Cases, Headache 2004, vol. 44, No. 8, p. 794-800.
Webster's Il New Riverside University Dictionary, The Riverside Publishing Company, 1984.
Welch KMA, Nagesh V, Rozell K, et al. Functional MRI of chronic daily headache. Cephalalgia 1999; 19:323.
Winner et al., "Long-Term Safety and Tolerability of OnabotulinumtoxinA Treatment in Patients with Chronic Migraine: Results of the Compel Study", Drug Safety (2019) 42: 1013-1024, published online May 17, 2019.

Illustration of the Face and Sites to Inject for Treatments 1, 2, 3 and 4.

INJECTION PARADIGM FOR ADMINISTRATION OF BOTULINUM TOXINS

CROSS REFERENCES OF RELATED APPLICATIONS

This application is a divisional of U.S. patent application Ser. No. 16/564,294, filed Sep. 9, 2019, now U.S. Pat. No. 11,033,610, which is a divisional of U.S. patent application Ser. No. 15/707,452, filed Sep. 18, 2017, now U.S. Pat. No. 10,406,213, which is a divisional of U.S. patent application Ser. No. 15/057,866, filed Mar. 1, 2016, now U.S. Pat. No. 9,764,011, which is a continuation of U.S. patent application Ser. No. 13/863,522, filed Apr. 16, 2013, now U.S. Pat. No. 9,279,001, which is a continuation in part of U.S. patent application Ser. No. 13/075,485, filed Mar. 30, 2011, now U.S. Pat. No. 8,501,195, which claims the benefit of U.S. Provisional Application Ser. No. 61/319,230, filed Mar. 30, 2010, and 61/320,667, filed Apr. 2, 2010, all incorporated entirely by reference.

FIELD

Embodiments of the present invention relate to the treatment of various disorders, specifically to injection administration protocols utilizing botulinum neurotoxin.

BACKGROUND

It is known that botulinum toxins can be utilized to treat a variety of disorders. Examples include U.S. Pat. No. 5,714,468 (migraine) issued Feb. 3, 1998; Published U.S. Patent Application No. 20050191321 (headache), Ser. No. 11/039,506, filed Jan. 18, 2005; Published U.S. Patent Application No. 20050191320 (medication overuse headache), Ser. No. 10/789,180, filed Feb. 26, 2004; and U.S. Pat. No. 7,811,587 (neuropsychiatric disorders), issued Oct. 12, 2010; all incorporated entirely by reference.

An example of a disorder treatable with botulinum toxins is chronic migraine (CM), a disabling headache disorder, affecting 1.3% to 2.4% of the general population and considered the most common type of primary chronic daily headache in the United States. CM is linked with suffering, disability, and medication overuse, and only one third of CM patients use headache prophylactic medication. Few headache preventive treatments have been investigated for patients with CM. Thus, there remains a need for optimized and targeted methodologies to treat this malady in particular, specific and useful injection and dosage paradigms for utilizing botulinum toxins to treating CM.

Another condition amenable to treatment with botulinum toxin is Medication Overuse Headache Disorder (MOU). It has been described as a self-sustaining, rhythmic, headache medication cycle characterized by daily or near daily headache with irresistible and predictable use of immediate relief medications. Evidence supporting the existence of MOH is widely published in the medical literature.

SUMMARY OF THE INVENTION

In one embodiment, the present invention teaches a method for prophylactically treating a headache in a patient suffering from chronic migraine headaches, the method essentially consisting of local administration of a botulinum neurotoxin to the frontalis, corrugator, procerus, occipitalis, temporalis, trapezius and cervical paraspinal muscles of the patient that suffers from the migraine headache, where the botulinum neurotoxin is administered, to the frontalis at about twenty units divided among four sites of injection, to the corrugator at about ten units divided among two sites of injection; to the procerus at about five units to one site of injection; to the occipitalis at about thirty units divided among six sites of injection to about forty units divided among eight sites of injection; to the temporalis at about forty units divided among eight sites of injection up to fifty units divided among ten sites of injection; to the trapezius at about thirty units divided among six sites of injection up to about fifty units divided among ten sites of injection and to the cervical paraspinal muscles at about twenty units divided among four sites of injection, and where the botulinum neurotoxin is injected at 31 to 39 injection sites. In one embodiment, the botulinum neurotoxin is onabotulinumtoxin A. In another embodiment, the botulinum neurotoxin is a pure toxin, devoid of complexing proteins. In a specific embodiment, the botulinum neurotoxin is incobotulinumtoxinA.

In another embodiment, the present invention discloses a method for treating or reducing the occurrence of a headache in a patient with chronic migraine headaches, the method consisting essentially of administration of abobotulinumtoxinA to the frontalis, corrugator, procerus, occipitalis, temporalis, trapezius and cervical paraspinal muscles of the patient that suffers from the migraine headache; wherein the botulinum neurotoxin is administered, to the frontalis at about from forty units to about 100 units divided among four sites of injection; to the corrugator at about from twenty units to about fifty units divided among two sites of injection; to the procerus at about from ten units to about twenty five units to one site of injection; to the occipitalis at about from sixty units to about one hundred fifty units divided among six sites of injection to about from eighty units to about two hundred units divided among eight sites of injection; to the temporalis at about from eighty units to about two hundred units divided among eight sites of injection up to from one hundred units to about two hundred fifty units divided among ten sites of injection; to the trapezius at about from sixty units to about one hundred fifty units divided among six sites of injection up to about from one hundred units to about two hundred fifty units divided among ten sites of injection and to the cervical paraspinal muscles at about from forty units to about one hundred units divided among four sites of injection; and wherein abobotulinumtoxinA is injected at 31 to 39 injection sites.

In another embodiment, the present invention discloses a method for treating or reducing the occurrence of a headache in a patient with chronic migraine headaches, the method consisting essentially of: local administration of a botulinum neurotoxin to the frontalis, corrugator, procerus, occipitalis, temporalis, trapezius and cervical paraspinal muscles of the patient that suffers from the migraine headache; wherein the botulinum neurotoxin is administered, to the frontalis at about eighty units divided among four sites of injection; to the corrugator at about forty units divided among two sites of injection; to the procerus at about twenty units to one site of injection; to the occipitalis at about one hundred twenty units divided among six sites of injection to about one hundred sixty units divided among eight sites of injection; to the temporalis at about one hundred sixty units divided among eight sites of injection up to two hundred units divided among ten sites of injection; to the trapezius at about one hundred twenty units divided among six sites of injection up to about two hundred units divided among ten sites of injection and to the cervical paraspinal muscles at about eighty units divided among four sites of injection; wherein the botulinum neurotoxin is injected at 31 to 39 injection sites. In one specific embodiment, the botulinum neurotoxin is abobotulinumtoxinA.

BRIEF DESCRIPTION OF THE DRAWINGS

The following drawings are presented to illustrate aspects and features of embodiments of the present invention.

FIG. 3 shows a decrease in narcotic use in the BOTOX®-treated patients.

DETAILED DESCRIPTION OF THE PREFERRED EMBODIMENTS

Figure 1:
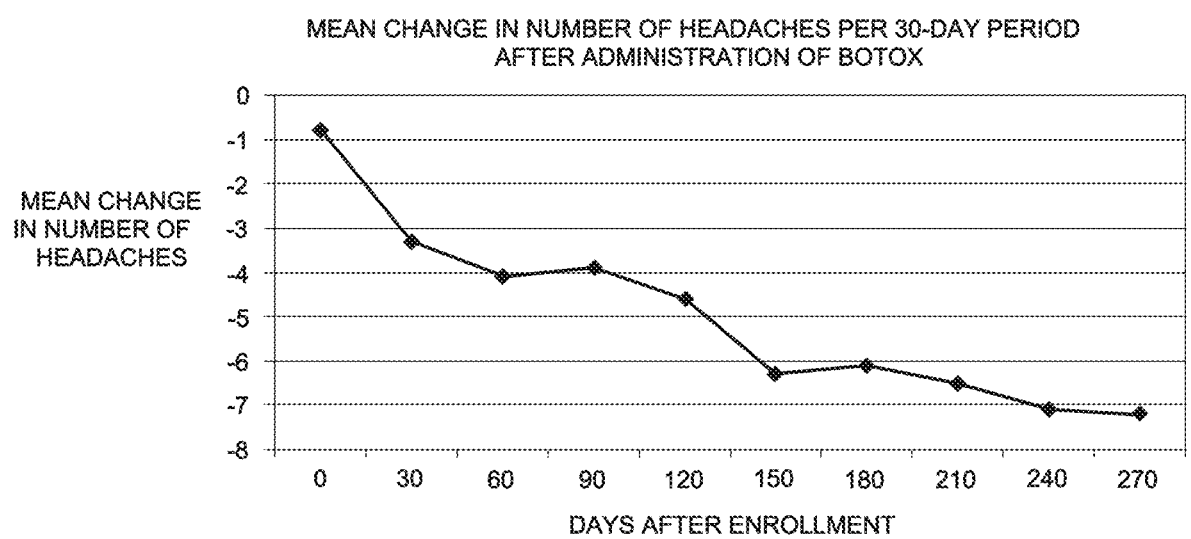
FIG. 1 is a graph showing the results (mean change in the number of headaches per thirty day period) of a clinical study carried out for use of BOTOX® to inter alia treat migraine headache, showing that the patients had fewer headaches after administration of BOTOX®. In the data shown in the Figures, the patients had been administered BOTOX® at days 0, 90 and 180.

In certain embodiments, the dose of a botulinum toxin used according to embodiments of the present invention is less than the amount of botulinum toxin that would be used to paralyze a muscle, because an intent of a method according to embodiments of the present invention is not to paralyze a muscle but to reduce a pain sensory output from sensory neurons located in or on a muscle, or in or under the skin.

The following definitions apply herein:

"About" means approximately or nearly and in the context of a numerical value or range set forth herein means±10% of the numerical value or range recited or claimed.

"Alleviating" means a reduction in the occurrence of a pain, of a headache or of a symptom of a headache. Thus, alleviating includes some reduction, significant reduction, near total reduction, and total reduction. An alleviating effect may not appear clinically for between 1 to 7 days after administration of a Clostridial toxin to a patient or sometime thereafter.

"Botulinum toxin" means a botulinum neurotoxin as either pure toxin or complex, native, recombinant, or modified, and includes botulinum toxin type A, type B, type $C_1$, type D, type E, type F, and type G. As used herein, this term excludes non-neurotoxins, such as the cytotoxic botulinum toxins $C_2$ and $C_3$.

"Local administration" means administration of a pharmaceutical agent to or to the vicinity of a muscle or a subdermal location in a patient by a non-systemic route. Thus, local administration excludes systemic routes of administration, such as intravenous or oral administration.

"Peripheral administration" means administration to a location away from a symptomatic location, as opposed to a local administration.

"MOU" means medication overuse headache or medication overuse headache disorder.

"Treating" or "treatment" means to alleviate (or to eliminate) at least one symptom (such as, for example, headache pain), either temporarily or permanently. This can include prophylactic applications to prevent at least one symptom of headache.

Disclosed herein are embodiments of an administration paradigm for botulinum neurotoxins. In some embodiments, the method can include specific injection locations and dosage amounts of botulinum toxin to treat various disorders, including, for example, CM, MOU, ND's, and the like. In certain embodiments of the invention, the disorder can be treated by intramuscular administration of the toxin in specific amounts or ranges of amounts to specific sites within the upper torso of the patient. In certain embodiments, such sites can include, for example, the head, the neck, one or both shoulders, in both the anterior or posterior positions. The botulinum toxin can be a botulinum toxin type A, type B, type $C_1$, type D, type E, type F, or type G, or any combination thereof. The botulinum neurotoxin can be a recombinantly made botulinum neurotoxins, such as botulinum toxins produced by *E. coli*. The botulinum neurotoxin can be a pure toxin, devoid of complexing proteins, such as Xeomin® (incobotulinumtoxinA). In some embodiments, the amount of incobotulinumtoxin A administered according to a method within the scope of embodiments of the invention is similar to the amount of onabotulinumtoxinA (such as BOTOX®) administered, as comparative studies have suggested that one unit of IncobotulinumtoxinA has a potency approximately equivalent to one unit of onabotulinumtoxinA.

In addition, the botulinum neurotoxin can be a modified neurotoxin, that is a botulinum neurotoxin which has at least one of its amino acids deleted, modified or replaced, as compared to a native toxin, or the modified botulinum neurotoxin can be a recombinant produced botulinum neurotoxin or a derivative or fragment thereof. In certain embodiments, the modified toxin has an altered cell targeting capability for a neuronal or non-neuronal cell of interest. This altered capability is achieved by replacing the naturally-occurring targeting domain of a botulinum toxin with a targeting domain showing a selective binding activity for a non-botulinum toxin receptor present in a non-botulinum toxin target cell. Such modifications to a targeting domain result in a modified toxin that is able to selectively bind to a non-botulinum toxin receptor (target receptor) present on a non-botulinum toxin target cell (re-targeted). A modified botulinum toxin with a targeting activity for a non-botulinum toxin target cell can bind to a receptor present on the non-botulinum toxin target cell, translocate into the cytoplasm, and exert its proteolytic effect on the SNARE complex of the target cell. In essence, a botulinum toxin light chain comprising an enzymatic domain is intracellularly delivered to any desired cell by selecting the appropriate targeting domain.

Botulinum toxins for use according to the present invention can be stored in lyophilized, vacuum dried form in containers under vacuum pressure or as stable liquids. Prior to lyophilization the botulinum toxin can be combined with pharmaceutically acceptable excipients, stabilizers and/or carriers, such as, for example, albumin, or the like. In embodiments containing albumin, the albumin can be, for example, human serum albumin, or the like. The lyophilized material can be reconstituted with a suitable liquid such as, for example, saline, water, or the like to create a solution or composition containing the botulinum toxin to be administered to the patient.

The amount of the botulinum toxin administered according to a method within the scope of embodiments of the invention can vary according to the particular characteristics of the pain being treated, including its severity and other various patient variables including size, weight, age, and responsiveness to therapy. To guide the practitioner, typically, no less than about 1 unit and no more than about 25 units of a botulinum toxin type A (such as BOTOX®) is administered per injection site per patient treatment session. For a botulinum toxin type A such as DYSPORT® (abobotulinumtoxinA), no less than about 2 units and no more than about 125 units of the botulinum toxin type A are administered per injection site, per patient treatment session. In some embodiments, the amount of abobotulinumtoxinA, (such as DYSPORT®), administered in the present method is about four times the amount of onabotulinumtoxinA (such as BOTOX®) administered, as comparative studies have suggested that one unit of onabotulinumtoxinA has a potency that is approximately equal to four units of abobotulinumtoxinA. For a botulinum toxin type B such as MYOBLOC®, no less than about 40 units and no more than about 1500 units of the botulinum toxin type B are administered per injection site, per patient treatment session.

Preferably, for BOTOX® no less than about 2 units and no more about 20 units of a botulinum toxin type A are administered per injection site per patient treatment session; for DYSPORT® (abobotulinumtoxinA), no less than about 4 units and no more than about 100 units are administered per injection site per patient treatment session, and; for MYOBLOC®, no less than about 80 units and no more than about 1000 units are administered per injection site, per patient treatment session.

More preferably, for BOTOX® no less than about 5 units and no more about 15 units of a botulinum toxin type A; for DYSPORT® (abobotulinumtoxinA), no less than about 20 units and no more than about 75 units, and; for MYOBLOC®, no less than about 200 units and no more than about 750 units are, respectively, administered per injection site, per patient treatment session.

Generally, the total amount of BOTOX®, DYSPORT® or MYOBLOC®, suitable for administration to a patient according to the methods of the invention disclosed herein should not exceed about 300 units, about 1,500 units or about 15,000 units respectively, per treatment session.

The treatment effects of the botulinum toxin can persist for between about 1 month and 5 years.

Embodiments of the invention provide a targeted, fixed injection paradigm directed to a specific set of muscles with a specific minimum number and volume of injections, and further provides for the additional/optional administration of additional botulinum toxin to specific site of selected muscles. In one embodiment, the fixed dosage (that is, a minimum dosage amount in accordance with the fixed amounts and locations specified in a package insert or prescribing information) of botulinum toxin is administered to the frontalis, corrugator, procerus, occipitalis, temporalis, trapezius and cervical paraspinal muscles of a patient, and further a variable amount of additional botulinum toxin can be added to four or less of the seven head/neck areas such that the total amount of botulinum toxin administered does not exceed a maximum total dosage as indicated in the package insert or prescribing information accompanying a botulinum toxin-containing medicament. The botulinum toxin can be selected from the group consisting of botulinum toxin types A, B, C, D, E, F and G. Botulinum toxin type A is a preferred botulinum toxin. The botulinum toxin can be administered in an amount of between about 1 unit and about 3,000 units, or between about 2 units and about 2000 units, or between about 5 units and about 1000 units, or between about 10 units and about 500 units, or between about 15 units and about 250 units, or between about 20 units and about 150 units, or between 25 units and about 100 units, or between about 30 units and about 75 units, or between about 35 units and about 50 units, or the like, and the alleviation of the symptoms can persist for between about 1 month and about 5 years.

In one embodiment, a method is disclosed that utilizes a dose and injection paradigm of 155 units of BOTOX® (typically provided as 100 Units of *Clostridium botulinum* type A neurotoxin complex, with 0.5 mg of human serum albumin, and 0.9 mg of sodium chloride in a sterile, vacuum-dried state for reconstitution), administered as 31 fixed-site, fixed-dose (5 units per) injections, and an optional 40 units in up to 8 additional injection sites using a follow-the-pain regimen per treatment cycle (for up to 39 injection sites and up to 195 units total). The total dose is divided across 7 head/neck muscles and is repeated every 12 weeks.

In an embodiment, a method for treating a migraine such as, for example, CM, can encompass administration of a botulinum toxin to 31 fixed injection sites across seven head/neck muscles. Optionally, up to 8 additional injection sites into three specific muscles, where these three muscles are subset of the above seven head/neck muscles, are administered utilizing a follow-the pain regimen to provide flexibility in the dose/muscle for the three muscles, to address individual patient needs. In particular embodiments, a minimum of 155 units of a botulinum toxin type A up to about 195 units of a botulinum toxin type A, are administered in accordance with a particular injection paradigm herein disclosed.

In a specific embodiment, a method for treating CM comprises the step of local administration of a botulinum neurotoxin to the frontalis, corrugator, procerus, occipitalis, temporalis, trapezius and cervical paraspinal muscles of the CM patient such that the botulinum neurotoxin is administered to the frontalis at about twenty units divided among four sites of injection, to the corrugator at about ten units divided among two sites of injection, to the procerus at about five units to one site of injection, to the occipitalis at about thirty units divided among six sites of injection to about forty units divided among eight sites of injection; to the temporalis at about forty units divided among eight sites of injection up to fifty units divided among ten sites of injection, to the trapezius at about thirty units divided among six sites of injection up to about fifty units divided among ten sites of injection and to the cervical paraspinal muscles at about twenty units divided among four sites of injection, such that the total amount of botulinum neurotoxin administered is from about 155 units to about 195 units injected at from 31 to 39 injection sites, respectively.

Figure 2:
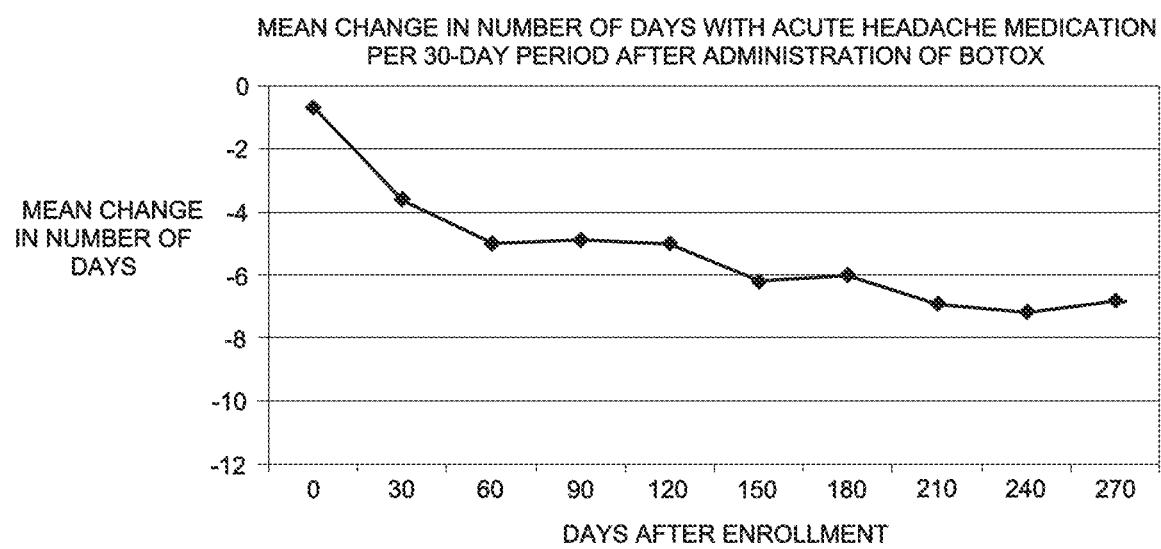
FIG. 2 is a graph showing the results (mean change in the number of days patients were concurrently taking acute headache pain alleviation medication per thirty day period) of a clinical study using BOTOX® to inter alia treat migraine headache, showing that the patients had fewer days when they were taking acute headache pain alleviation medication after administration of BOTOX®.
Figure 3:
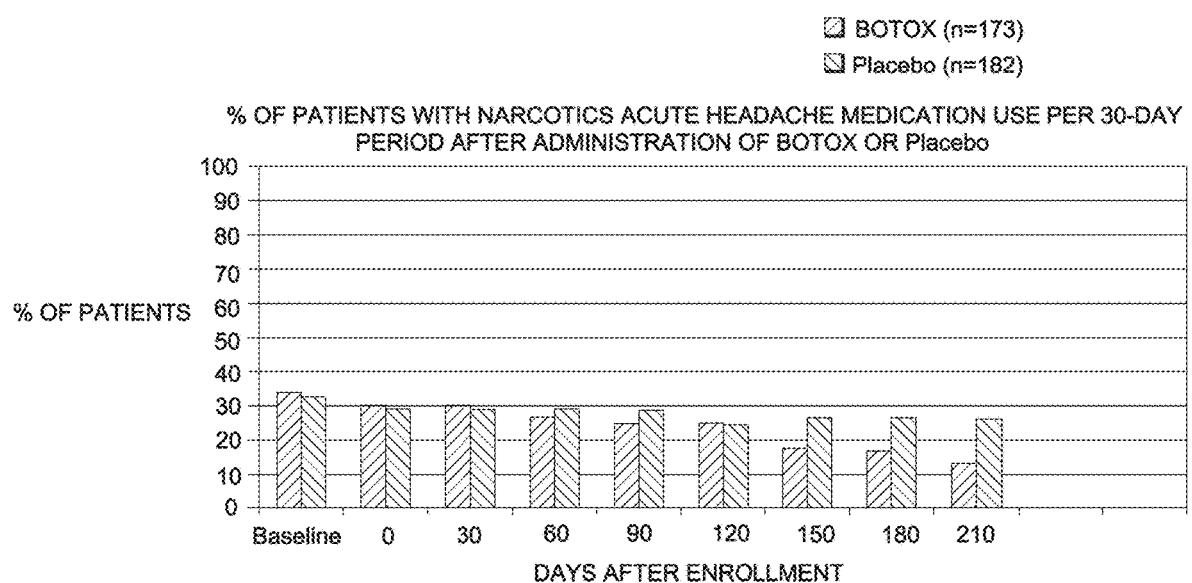
FIG. 3 is a graph showing a comparison of the percent of patients (some who had been administered BOTOX® and some who had been administered a placebo) who were over a thirty day period using narcotics medication to control acute headache pain.

In one aspect, embodiments of the present invention are based on the discovery that a botulinum toxin can be used to treat a patient with MOU to reduce both (a) the number of headaches experienced by the patient (see FIG. 1) and (b) the daily use of acute headache pain medication by the patient (FIG. 2). In particular, we have found (see FIG. 3) that a botulinum toxin can be used to reduce use by patients of narcotic pain medication.

Figure 4:
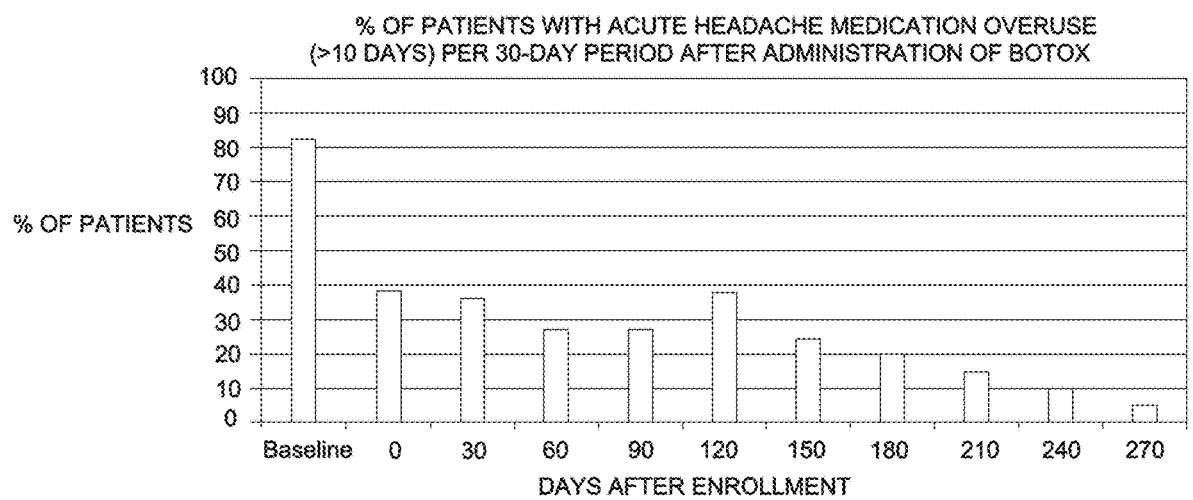
FIG. 4 is a graph showing a decrease in the percentage of patients who had acute headache medication overuse in a thirty day period after administration of BOTOX®.

Additionally, we found that patients who were overusing pain alleviation medication experienced a significant reduction in their use of such medications after treatment with a botulinum toxin (see FIG. 4). We also found that there was a significant reduction in the intake of triptan medications in triptan medication overuse patients (see FIG. 5).

Embodiments of the invention can also be used as part of a detoxification protocol whereby a patient who is being weaned off acute pain medications is facilitated in this goal by concurrent administration of a botulinum toxin. Additional embodiments of the invention can be used to treat other chronic pain conditions, including, for example, back pain, neuropathic pain, allodynia, fibromyalgia, and the like.

In an embodiment, a method for treating an MOU patient can encompass administration of a botulinum toxin to 31 fixed injection sites across seven head/neck muscles. Optionally, up to 8 additional injection sites into three specific muscles, where these three muscles are subset of the above seven head/neck muscles, are administered utilizing a follow-the pain regimen to provide flexibility in the dose/muscle for the three muscles, to address individual patient needs. In particular embodiments, a minimum of 155 units of a botulinum toxin type A up to about 195 units of a botulinum toxin type A, are administered in accordance with a particular injection paradigm herein disclosed.

In a specific embodiment, a method for treating MOU comprises the step of local administration of a botulinum neurotoxin to the frontalis, corrugator, procerus, occipitalis, temporalis, trapezius and cervical paraspinal muscles of the MOU patient such that the botulinum neurotoxin is administered to the frontalis at about twenty units divided among four sites of injection, to the corrugator at about ten units divided among two sites of injection, to the procerus at about five units to one site of injection, to the occipitalis at about thirty units divided among six sites of injection to about forty units divided among eight sites of injection; to the temporalis at about forty units divided among eight sites of injection up to fifty units divided among ten sites of injection, to the trapezius at about thirty units divided among six sites of injection up to about fifty units divided among ten sites of injection and to the cervical paraspinal muscles at about twenty units divided among four sites of injection, such that the total amount of botulinum neurotoxin administered is from about 155 units to about 195 units injected at from 31 to 39 injection sites, respectively.

In an embodiment, a method for treating depression can encompass administration of a botulinum toxin to 31 fixed injection sites across seven head/neck muscles. Optionally, up to 8 additional injection sites into three specific muscles, where these three muscles are subset of the above seven head/neck muscles, are administered utilizing a follow-the pain regimen to provide flexibility in the dose/muscle for the three muscles, to address individual patient needs. In particular embodiments, a minimum of 155 units of a botulinum toxin type A up to about 195 units of a botulinum toxin type A, are administered in accordance with a particular injection paradigm herein disclosed.

In a specific embodiment, a method for treating ND's such as, for example, depression, in a patient in need thereof comprises the step of local administration of a botulinum neurotoxin to the frontalis, corrugator, procerus, occipitalis, temporalis, trapezius and cervical paraspinal muscles of the patient such that the botulinum neurotoxin is administered to the frontalis at about twenty units divided among four sites of injection, to the corrugator at about ten units divided among two sites of injection, to the procerus at about five units to one site of injection, to the occipitalis at about thirty units divided among six sites of injection to about forty units divided among eight sites of injection; to the temporalis at about forty units divided among eight sites of injection up to fifty units divided among ten sites of injection, to the trapezius at about thirty units divided among six sites of injection up to about fifty units divided among ten sites of injection and to the cervical paraspinal muscles at about twenty units divided among four sites of injection, such that the total amount of botulinum neurotoxin administered is from about 155 units to about 195 units injected at from 31 to 39 injection sites, respectively.

Significantly, a method within the scope of the present invention can provide improved patient function. "Improved patient function" can be defined as an improvement measured by factors such as a reduced pain, reduced time spent in bed, increased ambulation, healthier attitude, more varied lifestyle and/or healing permitted by normal muscle tone. Improved patient function is may be measured with an improved quality of life (QOL) or Health-Related Quality of Life (HRQL). QOL can be assessed, for example, using the SF-12 or SF-36 health survey scoring procedures, or the Migraine Specific Quality of Life Questionnaire (MSQ). SF-36 assesses a patient's physical and mental health in the eight domains of physical functioning, role limitations due to physical problems, social functioning, bodily pain, general mental health, role limitations due to emotional problems, vitality and general health perceptions. Scores obtained can be compared to published values available for various general and patient populations. The Migraine-Specific Quality of Life Questionnaire Version 2.1 is one of the most frequently utilized disease-specific tools assessing the impact of migraine on HRQL. The MSQ measures the impact of migraine on the patient's HRQL over the past 4 weeks across three dimensions: Role Function-Restrictive (RR), Role Function-Preventive (RP), and Emotional Function (EF). The MSQ was developed from an expert-based item review of the migraine literature and validated in a clinical sample of 458 new and stable EM patients. In the validation study the MSQ revealed high internal consistency (Cronbach's $\alpha$=0.79 to 0.85), a moderate to strong convergent validity, as well as an adequate discriminant validity. Martin and Colleagues 21 performed a multi-center study that further supported the evidence of a high internal consistency (Cronbach's $\alpha$=0.86 to 0.96), strong reliability and good validity of the 14-item MSQ among 267 participants.

The following non-limiting examples provide those of ordinary skill in the art with specific preferred methods to treat chronic migraine within the scope of the present disclosure, and it is not intended to limit the scope of the invention. In the following examples various modes of non-systemic administration of a Clostridial neurotoxin can be carried out. For example, by intramuscular injection, subcutaneous injection or by implantation of a controlled release implant.

EXAMPLES

The following non-limiting examples provide those of ordinary skill in the art with specific preferred methods to treat conditions within the scope of embodiments of the present invention and are not intended to limit the scope of the invention.

Example 1—Botulinum Toxin Type A Therapy for Headache Pain Associated with Chronic Migraine In similarly designed, multicenter, randomized, placebo-controlled, phase 3 trials, 1384 adults with CM were randomized to onabotulinumtoxinA (botulinum toxin type A) (n=688) or placebo (n=696). Both studies consisted of a 28-day baseline screening period (hereafter referred to as baseline), a 24-week, double-blind (DB) phase (2 injection cycles), and a 32-week, open-label (OL) phase (3 treatment cycles). Study visits occurred every 4 weeks and patients used a daily telephone diary to record their headache symptoms and acute pain medications. Participants were men or women aged 18 to 65 years with a history of migraine meeting the diagnostic criteria listed in ICHD-II (2004) Section 1, Migraine, with the exception of "complicated migraine," and with headache occurring ≥15 days/month with at least 50% of the headache days being migraine or probable migraine days.

Botulinum toxin type A blocks the release of neurotransmitters associated with pain genesis. As confirmed by preclinical and clinical trials, the presumed mechanism for headache prophylaxis is by blocking peripheral signals to the central nervous system, inhibiting central sensitization. The fixed-site approach herein disclosed targets distribution of botulinum toxin type A to muscles and skin in the innervation distribution of V1 and C2 nerves.

Based on analyses of the safety, tolerability, and efficacy of the dosing paradigms explored in previous studies, the instant injection paradigm was developed. In this example, the particular botulinum neurotoxin utilized is onabotulinumtoxinA (BOTOX® Allergan Inc. Irvine Calif.). Injection targets included the following muscles:

Frontalis, Corrugator, and Procerus: In the previous trials, patients most often reported the frontal/glabellar region as the origin and end of their headache; these and other trials showed that all 3 muscles needed injections for maximum efficacy.

Temporalis: In previous trials, the temporalis region was the second most frequent location cited as the start and end of head pain. In accordance with one aspect of the instant disclosure, a minimum dose of 20 units per side and up to an additional 10 units (follow-the-pain strategy) total (administered to 1 or both sides in 5 unit increments) is administered to this muscle.

Cervical Paraspinal Muscles: In previous trials, patients indicated that their headache pain frequently started and/or stopped in the back of the head (in the occipitalis and/or the neck). To maintain efficacy and improve overall tolerability (lower incidence of neck pain, neck rigidity, and neck muscle weakness), in one aspect the instant injection paradigm includes the recommendations of: (a) giving injections to the upper neck (cervical paraspinal muscles) at the base of the skull; (b) do not utilize a follow-the-pain injection regimen in the neck area; (c) keep injections superficial and (d) reduce the total dose injected to the neck region to a fixed-site, fixed-dose of 20 units total for this muscle group (10 units to each side of the head). Accordingly, it was shown that this dose adjustment was successful and safe, as only 1 patient here needed to use a soft collar compared to 10 in previous studies.

Occipitalis: In previous trials, the occipitalis was the third most frequently reported location for pain. In a previous study that explored the follow-the-pain strategy, the occipitalis dose was fixed at 20 units (10 units per side), whereas the highest dose allowed in this muscle in another study was 30 units (15 units per side). The total dose administered to the neck was reduced and thus to ensure that that there would be sufficient "back of the head" dose to ensure efficacy, minimum dose administered to the occipitalis muscle was 30 units (15 units per side); injection sites were standardized and located primarily above the occipital ridge to reduce the risk of neck weakness; optional follow-the-pain dosing with up to an additional 10 units was allowed.

Trapezius: In previous trials, approximately 20% to 30% of patients reported that their headache pain started and/or ended in the trapezius muscles. The follow-the-pain optional injections occurred frequently for this muscle group. Although not a general safety concern, the incidence of arm (shoulder) pain increased with higher doses; therefore, it was determined that a preferred dosage regimen for the trapezius muscle would be standardized to a minimum dose of 30 units (15 units on each side) and allow optional follow-the-pain injections to a maximum dose of 50 units, if clinically needed.

Masseter: The masseter muscle was not included as a target muscle group for injection in the instant paradigm, as surprisingly injections to the masseter did not aid in treating migraine headaches.

In one aspect of previous trials, the highest total dose per injection cycle evaluated was 260 units and the lowest dose was 105 units (trial one), while the second trial dose groups included 225 units, 150 units, and 75 units. In evaluating a dose response in this trial for tolerability, it was determined that the optimal total dose to maximize efficacy and tolerability was within the range of >150 and <200 units.

In the instant example, subjects were randomized in blinded fashion (1:1) to onabotulinumtoxinA (BOTOX®) (155 units) or placebo, administered as 31 fixed-site, fixed-dose, intramuscular (IM) injections across 7 specific head/neck muscle areas (frontalis, corrugator, procerus, temporalis, occipitalis, cervical paraspinal, and trapezius) (FIG. 17): Frontalis† 20 units (2 sites on each side: total 4 sites); Corrugator† 10 units (1 site on each side: total 2 sites) Procerus 5 units (1 site); Occipitalis† 30 units (3 sites on each side: total 6 sites); Temporalis† 40 units (4 sites on each side: total 8 sites); Trapezius† 30 units (3 sites on each side: total 6 sites); Cervical paraspinal muscles† 20 units (2 sites on each side: total 4 sites). Total dose range: 155 units. Each IM injection site=0.1 mL=5 U onabotulinumtoxinA (BOTOX®). (†Dose distributed bilaterally.)

Figure 17:
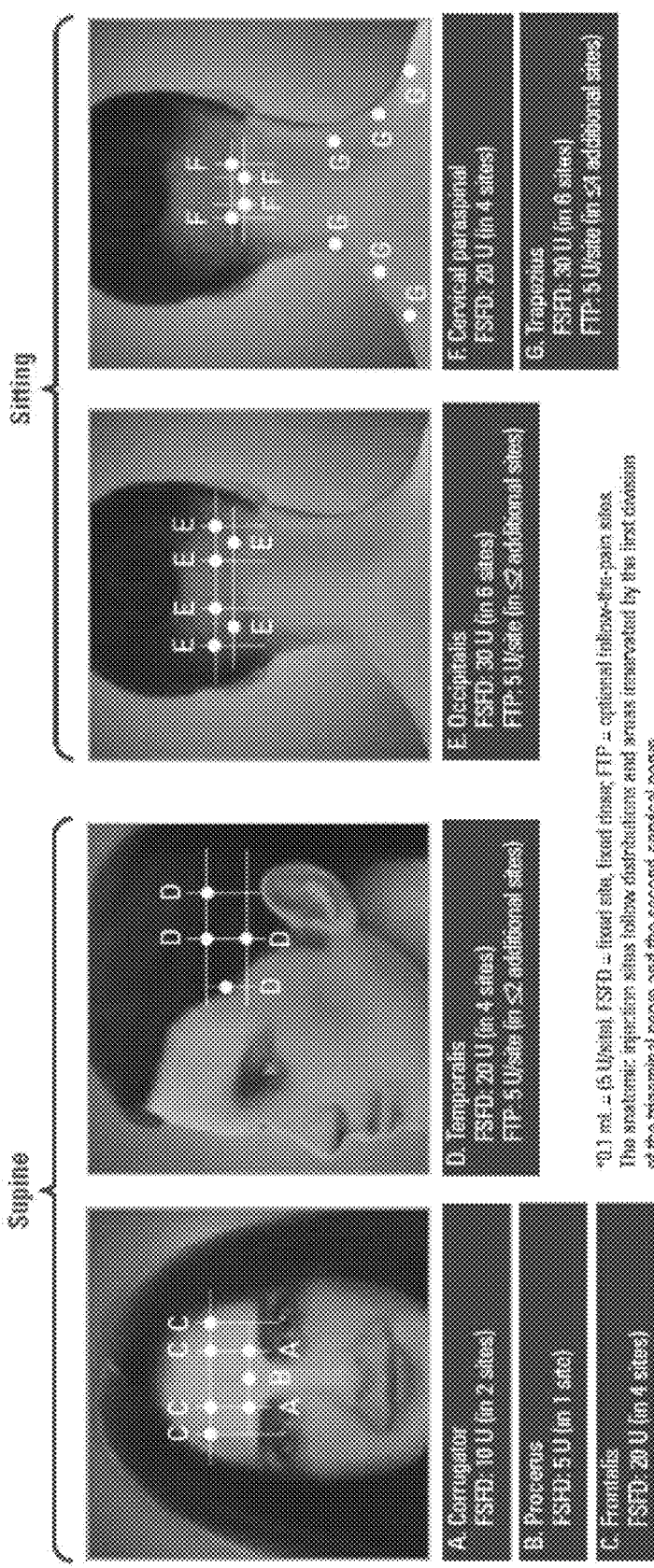
FIG. 17 depicts an example of fixed locations to which doses of botulinum toxin are administered to a patient (here in supine and sitting positions) in accordance with one embodiment of an injection paradigm.

Up to an additional 40 units onabotulinumtoxinA or placebo could be administered among 3 muscle groups (occipitalis, temporalis, or trapezius; total of 8 sites) using a protocol-defined, follow-the-pain paradigm (FIG. 17). The maximum dose was 195 units at 39 sites. The dose range per injection cycle was 155 units up to 195 units every 12 weeks for 5 cycles.

In practicing this example, medical practitioners were instructed in accordance with the following: dosing/administration: each 100 unit vial of onabotulinumtoxinA (BOTOX®) or placebo was diluted with 2 mL preservative-free normal saline, resulting in a concentration of 5 units/0.1 mL. Doses of 155 units to 195 units or placebo were administered intramuscularly using a sterile 30-gauge, 0.5-inch needle (with a Luer Lock) as injections of 0.1 mL (5 units) per site. A 1-inch needle was allowed at the physician's discretion in the neck region for patients with thick neck muscles. Guidelines for administering onabotulinumtoxinA were as follows: gloves should be worn while administering treatment; prior to injection, the skin should be cleansed according to standard practice for intramuscular injection (e.g. with alcohol); the needle should be inserted into the muscle with the bevel up, at approximately a 45-degree angle; once inserted, the needle hub should be held with 1 hand while the plunger is pulled back slightly with the other hand to prevent torque and blood return, respectively. If blood returns, the needle should be reinserted into the muscle; the plunger should be pushed to administer 0.1 mL (5 units) to each site.

The following is one example of a useful order of injection for administration of botulinum toxin in accordance with the instant disclosure. Anatomic injection sites follow distributions and areas innervated by the first division of the trigeminal nerve and the second cervical nerve.

In an exemplary paradigm, a medical practitioner palpated each muscle (bilaterally, if appropriate) prior to injection to verify muscle delineation and determine the presence of muscle tenderness and/or pain requiring additional treatment. Patients were supine for injections into the corrugator (2 injections, 1 per side), procerus (1 injection, midline), frontalis (4 injections, 2 per side), and temporalis (8 injections, 4 per side), in this sequence (FIG. 17). Patients were seated for injections into the occipitalis (6 injections, 3 per side), cervical paraspinal (4 injections, 2 per side), and trapezius (6 injections, 3 per side), in this sequence (FIG. 17). If needed, additional injections into the temporalis, occipitalis, and trapezius muscles were allowed, using the optional follow-the-pain paradigm (FIG. 17).

Post-administration, patients were observed for 10-15 minutes following treatment and were advised not to rub or massage the affected areas for 24 hours and told that any bumps appearing on the forehead should disappear within approximately 2 hours. Patients were advised that they may need and should use their acute pain medications for breakthrough headaches and to return at 4-week intervals and maintain a headache diary.

Pooled analyses demonstrated statistically significant differences favoring the herein disclosed dose of 155 to 195 units over placebo at all time points in the double blind phase across multiple headache symptom measures, including the pooled primary endpoint of change from baseline in frequency of headache days at 24 weeks: −8.4 onabotulinumtoxinA/−6.6 placebo; p<0.001.

Each and every feature described herein, and each and every combination of two or more of such features, is included within the scope of embodiments of the present invention provided that the features included in such a combination are not mutually inconsistent.

Example 2—Botulinum Toxin Type A Therapy for Headache Pain and for a Probable Medication Overuse Headache Disorder A clinical study was carried out with patients who complained of headache pain and who took frequent acute pain medications such as narcotics and triptans to control the pain. A botulinum toxin (BOTOX®) was administered to the patients at day 0, at day 90 and at day 180. The BOTOX® injections were administered intramuscularly in an average of 20 separate injections to each patient at each of the three injection sessions. The BOTOX® was administered to up to seven different muscles.

From 105 to 260 units of BOTOX® was administered to each patient at each of the three treatment sessions. It was found that the patients experienced a reduction in both (a) the number of headaches experienced by such patients (FIG. 1), and; (b) the daily use of acute headache pain medication by these patients (FIG. 2). In particular, it was found (FIG. 3) that a botulinum toxin can reduce use by these patients of narcotic pain medication.

Figure 5:
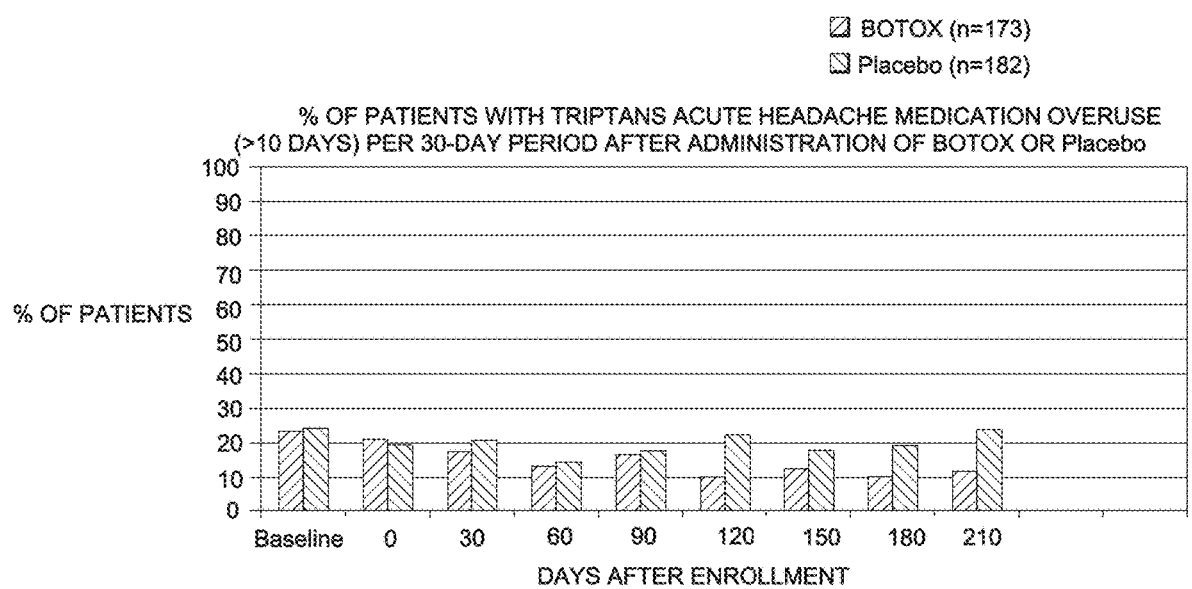
FIG. 5 is a graph showing a decrease in the percentage of patients who had demonstrated overuse of triptans in a thirty day period after administration of BOTOX®.
Figure 6:
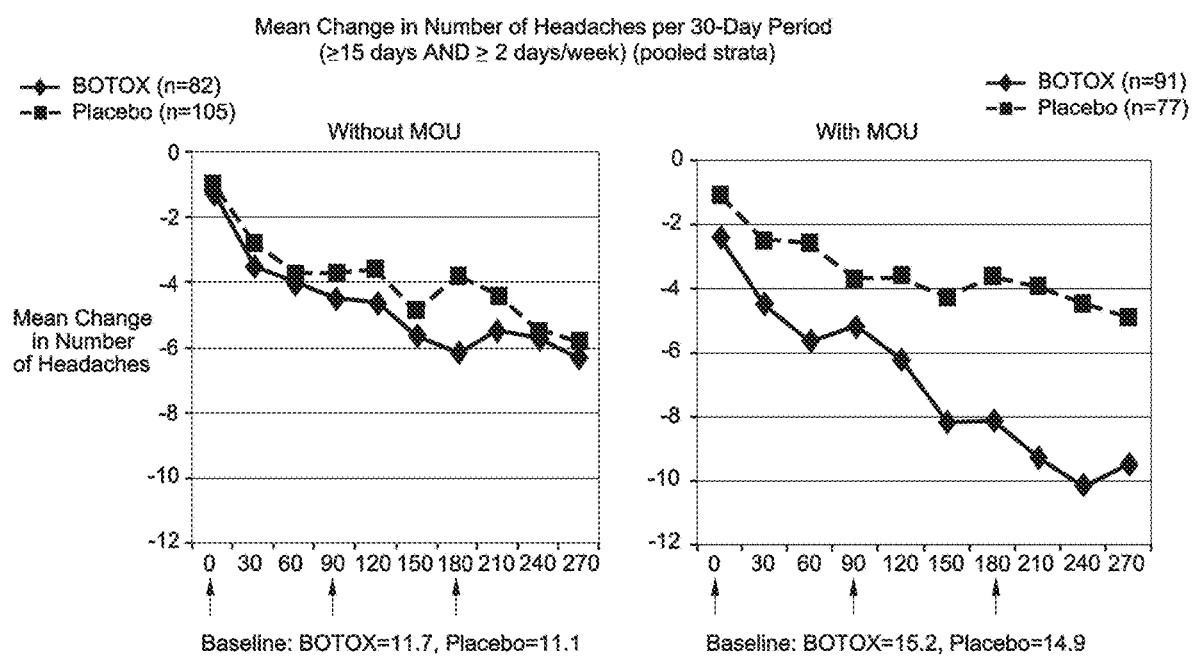
FIG. 6 comprises two graphs showing the mean change in the number of headaches experienced by patients over a thirty day period after administration of BOTOX®, where the patients either did not have MOU ("without MOU"; left side graph) or the patients did have an MOU disorder (right side graph). "≥15 days and ≥2 days/week" are criteria used to determine that a patient had an MOU disorder. MOU and MOD are synonymous terms. By definition, a patient has an MOU disorder if he or she takes an acute medication 15 or more days per month and at least twice a week in the week that they are experiencing the acute pain.

Additionally, it was found that use of a botulinum toxin in patients who were overusing pain alleviation medication resulted in a significant reduction in their use of such medications (see FIG. 4). It was also found that there was a significant reduction in the intake of triptan medications in overuse patients (FIG. 5). Thus, this clinical study surprisingly showed that a botulinum toxin can be used to treat a medication overuse headache disorder (MOU) (see FIG. 6).

Figure 7:
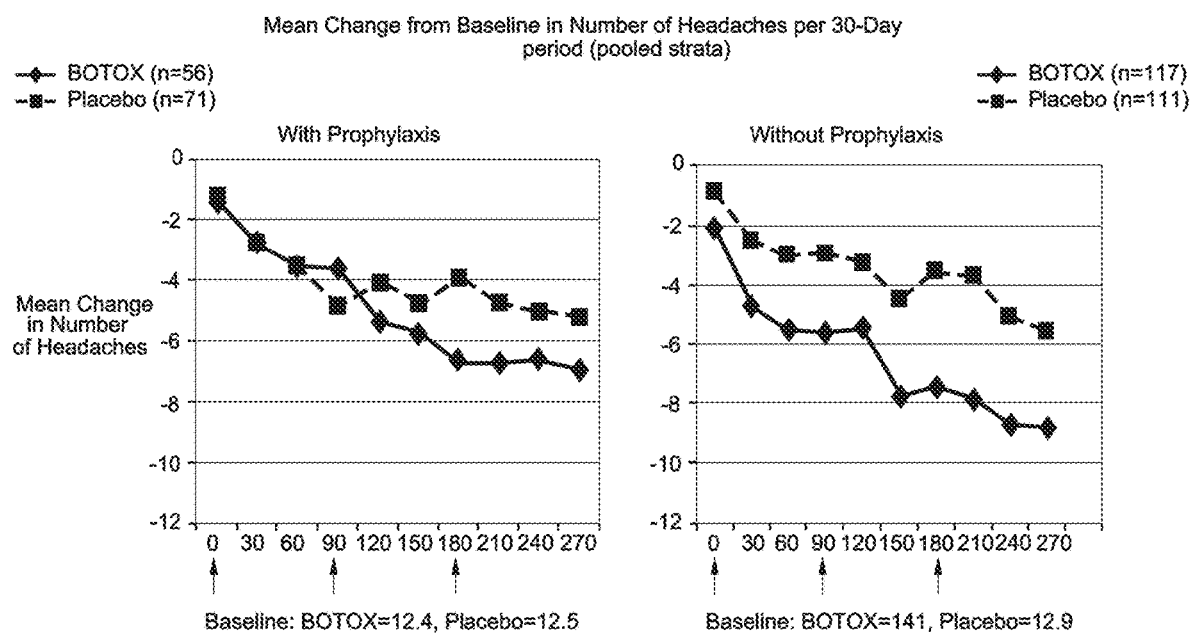
FIG. 7 comprises two graphs which show the mean change from baseline in the frequency of headaches per 30-day period in patients using (graph A) and not using (graph B) prophylactic headache medications at baseline, for a pooled population of patients. The Y-axis represents the mean change in the number of headaches per thirty day period. "n" indicates the number of patients in the sample of patients evaluated.

The study also demonstrated (see FIG. 7) that a botulinum toxin was more effective in patients who were not using a concurrent headache prophylaxis treatment regardless of any medication overuse issue.

Figure 8:
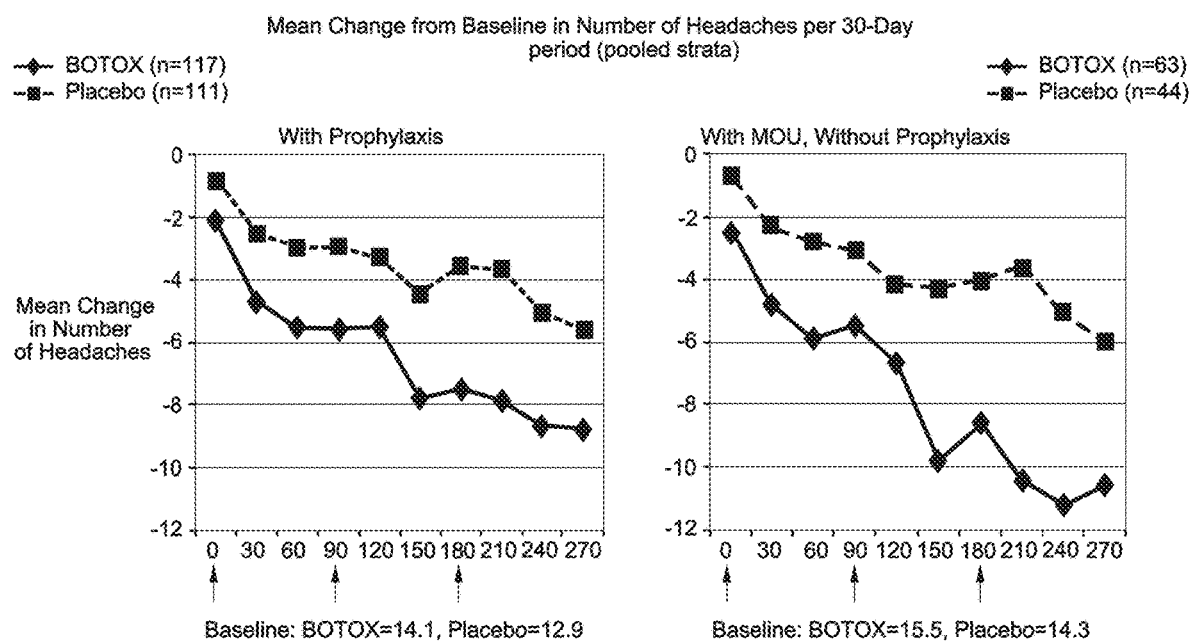
FIG. 8 comprises two graphs which show the mean change in the number of headaches experienced by patients over a thirty day period after administration of BOTOX®, where the patients either were not concurrently using another headache prophylaxis treatment (left side graph) or the patients were not concurrently using another headache prophylaxis treatment and did have an MOU disorder (right side graph).
Figure 9:
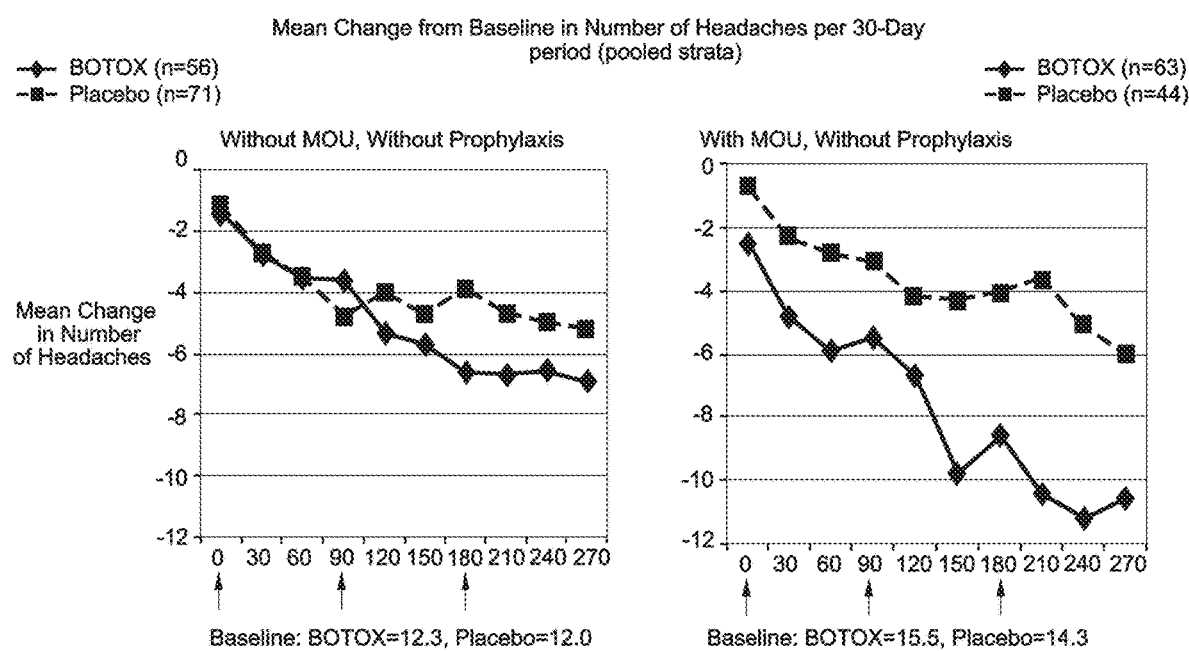
FIG. 9 comprises two graphs showing the mean change in the number of headaches experienced by patients over a thirty day period after administration of BOTOX®, where the patients either were not concurrently using another headache prophylaxis treatment and did not have an MOU disorder (left side graph) or the patients were not concurrently using another headache prophylaxis treatment and did have an MOU disorder (right side graph).

Additionally, the same study showed (see FIGS. 8 and 9) that a botulinum toxin was more effective in the patients who were not using a concurrent headache prophylaxis treatment and were overusing medication. This is a discovery in addition to our discovery that a botulinum toxin can be used to treat headache in a patient overusing acute medication, without regard to the fact that the patient is being treated with a botulinum toxin monotherapy or that he or she is being treated for headache with other headache prophylaxis medications.

Figure 10:
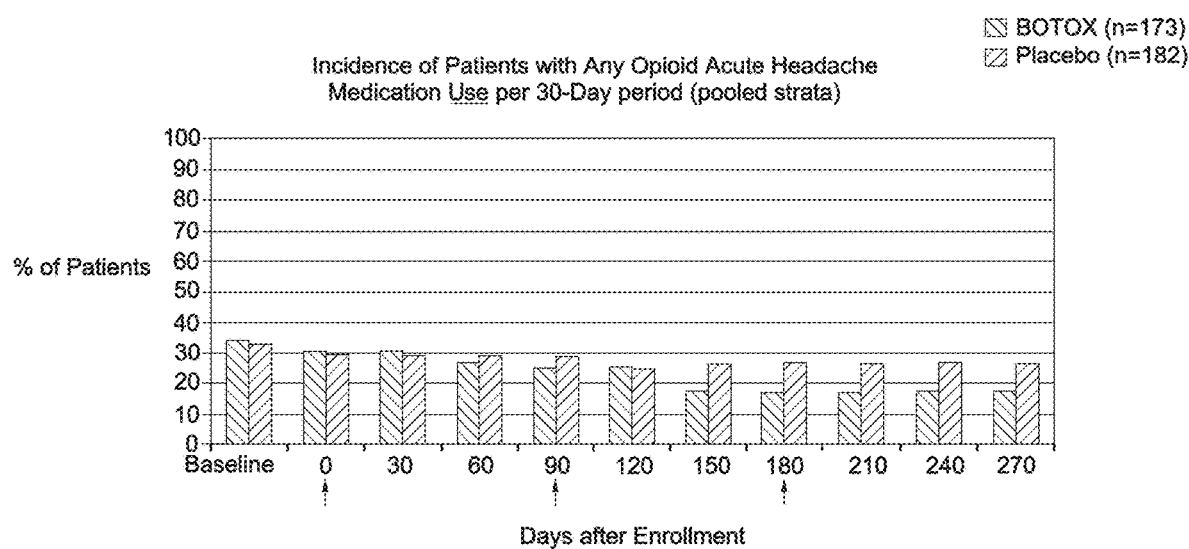
FIG. 10 is a bar chart showing the percentage of patients over a thirty day period after administration of BOTOX® who were also using an opioid acute headache medication.

Furthermore, with regard to acute medication use in patients (not overuse, but any use) the study showed that treatment of headache with a botulinum toxin resulted in a significant decrease in use of narcotics by these patients (see e.g. day 210 in FIG. 10).

Figure 11:
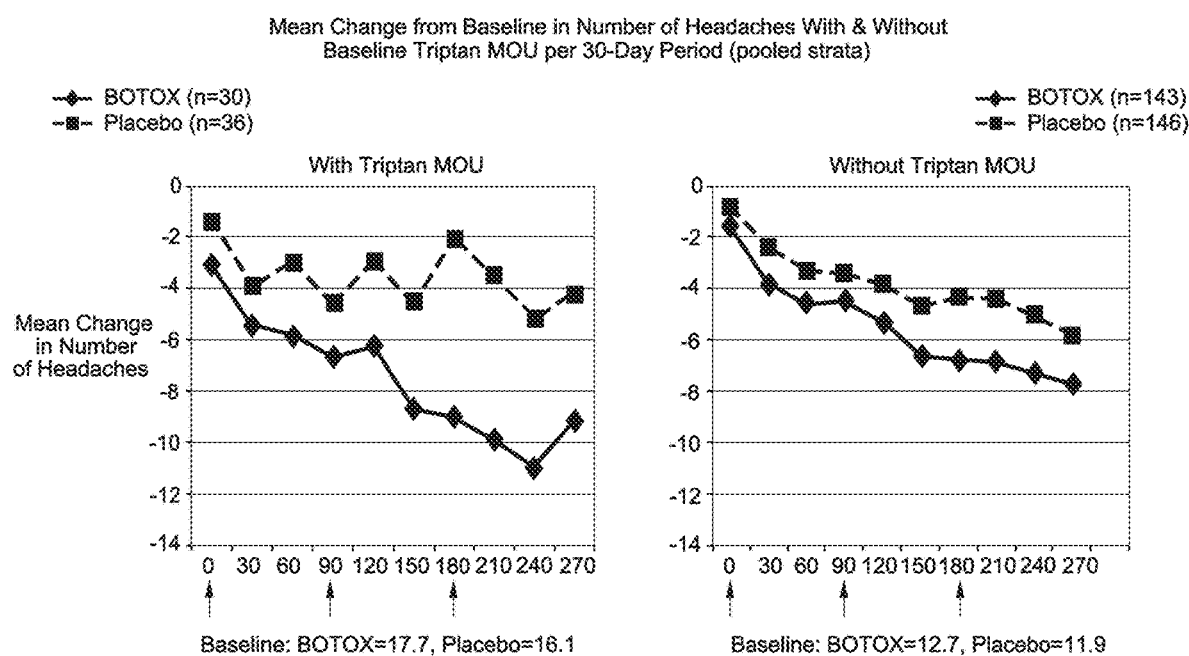
FIG. 11 comprises two graphs which show the mean change in the number of headaches experienced by patients over a thirty day period after administration of BOTOX®, where the patients either were triptan medication overuse patients (left side graph) or not triptan medication overuse patients (right side graph).
Figure 12:
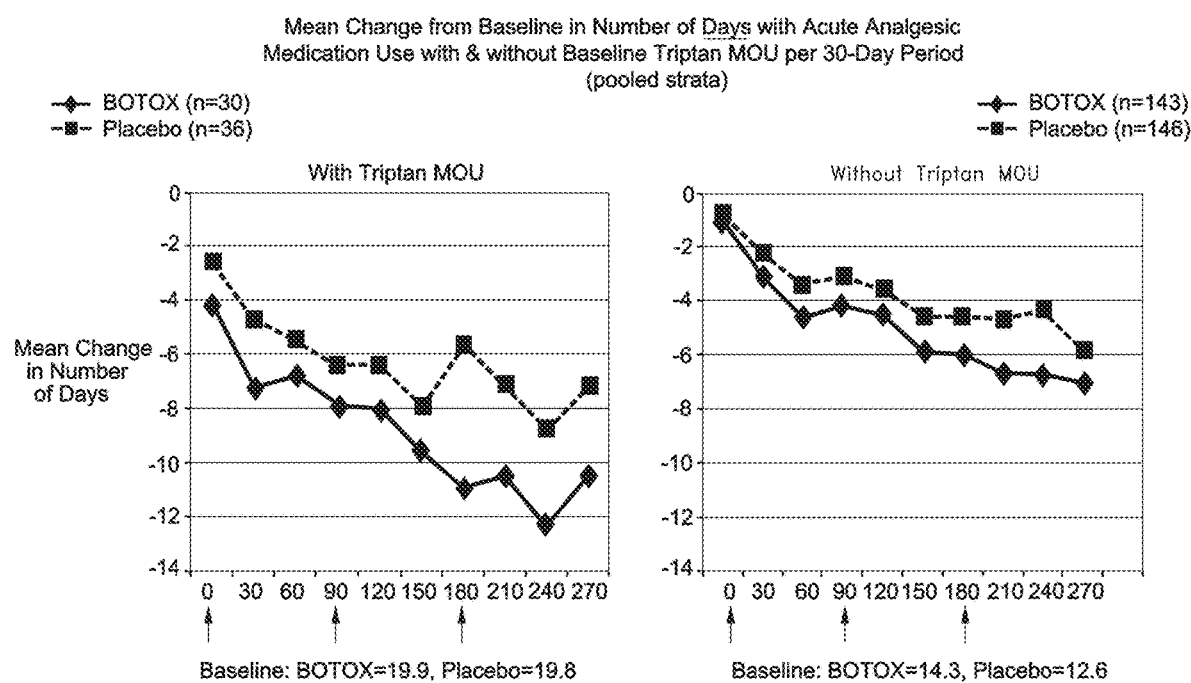
FIG. 12 comprises two graphs which shows the mean change from baseline (after administration of BOTOX®) in number of days with acute headache (analgesic) medication use by the patients, where the patients were either triptan medication overuse patients (left side graph) or not triptan medication overuse patients (right side graph).

Finally, and significantly the study also showed (see FIGS. 11 and 12) that after treatment with a botulinum toxin there was a greater decrease in the frequency of headache and in the number of days acute analgesic medications were required in the patients who were overusing triptans headache medication at baseline, as compared to the patents who were not overusing triptan medications. This indicates that triptans are more effective to treat headache when used in conjunction with a botulinum toxin. Thus, a method for increasing the effectiveness of a triptan to treat a headache can be carried out by using a triptan and a botulinum toxin concurrently to treat a headache.

Clinically, triptan medication overuse appears to actually cause or to exacerbate headache pain, as opposed to the alleviation of headache pain which can result from normal triptan use. Therefore, it was a surprising discovery, as set forth by FIGS. 11 and 12, to find that administration of a botulinum toxin helps to prevent headaches in a patient population who have headaches, more frequent headaches or exacerbated headaches due to triptan medication overuse. This discovery is demonstrated by study results and patient observations showing that triptan MOU patients needed less triptan medication after botulinum toxin administration.

Example 3—Botulinum Toxin Type A Therapy for Chronic Headache

This study assessed the potential benefit of BOTOX® in headache prophylaxis in the adult chronic daily headache population. The term chronic daily or chronic near-daily headache has been used to refer to very frequent headaches (16 or more headache days a month) not related to a structural or systemic illness (Silberstein and Lipton, 2001). The key requirement for entry into the current study was primary headache disorder with 16 headache days per month by history and confirmed by electronic diary during baseline. Headache disorder could include any combination of episodic/chronic tension-type headaches, migraines with or without aura, and/or migrainous headaches (as defined by IHS criteria [Headache Classification Subcommittee of the IHS, 1988, revised 2004], and/or chronic daily headache as defined by Silberstein and Lipton, 2001).

A study was conducted with a multicenter, double-blind, randomized, placebo-controlled, parallel group of multiple treatments with Botox® for the prophylactic treatment of headaches in a chronic migraine headache population. The overall duration of the study for each patient was 11 months. Patients were screened at Day −60 (baseline period). During this period data were collected daily from the patient regarding specified characteristics of their headache episodes and headache medication use for 30 days using electronic telephone diaries. Following the baseline period, patients returned at Day −30 (Treatment 1) for the placebo run-in period. At this visit, patients meeting the inclusion/exclusion criteria were injected with single-masked placebo, and again recorded specified characteristics of their headache episodes for 30 days using electronic diaries. Treatment 1 injections were in a minimum of 6 muscle areas and 23 to 58 injection sites within these areas, dependent upon the location and severity of pain. The investigator also had the option to inject the masseter if the patient was experiencing pain in that muscle.

After 30 days (at Day 0) patients returned to be randomized for Treatment 2. Prior to randomization, using diary information collected during the placebo run-in period, patients were classified as a placebo responder if they had <16 headache days or had a ≥30% decrease from baseline in the frequency of headache days. All other patients were considered placebo non-responders. Patients within each stratum (responders, non-responders) were randomized to receive either BOTOX® or placebo at Day 0 (Treatment 2).

Patients received additional treatments at Day 90 (Treatment 3) and Day 180 (Treatment 4). Patients returned for follow-up visits at 30-day intervals following each treatment through Day 270. If a patient exited the study at any visit prior to Day 270 (exit), all exit procedures and evaluations were to be completed at that visit. For Treatments 2, 3, and 4, patients were injected with BOTOX® or placebo using the same dose and volume and in the same muscle areas and sites as in Treatment 1. The schedule of study visits and measurements is shown in Table 2.

The study was randomized and double-blind to minimize investigator and patient bias. Blinding was ensured by the similarity in appearance of the vials of study medication and requiring that an individual at each study center who had no other study involvement reconstituted the study medication and filled the syringes for injection. A placebo-controlled, parallel-group design eliminated possible confounding effects that are inherent in other study designs.

In contrast to the fixed site/fixed dosage treatment approach used in previous clinical studies in the episodic migraine population, physicians participating in this study were allowed to use a more individualized or patient-tailored treatment approach depending on the location of the patient's head pain. Specifically, physicians were given the opportunity to determine the number of injection sites and the dosage within a protocol-specified range to be administered for the specified frontal and posterior muscle areas of the head and neck, depending on the location and severity of a patient's headache. Maximum dose levels allowed in this study also were higher than those used in previous studies due to the addition of injection of larger, posterior pericranial and neck muscles.

Due to the high placebo response rate seen in previous studies, a placebo run-in period was implemented in the present study to stratify patients into 2 groups (placebo responders and non-responders). During the placebo run-in period, patients were not informed as to whether they were injected with BOTOX® or placebo. Furthermore, the study protocol was amended to include 3 double-blinded treatment cycles.

Efficacy criteria were as follows. For the primary variable, a difference of 3 headache-free days between BOTOX® and placebo in the mean change from baseline in the frequency of headache-free days per month at Day 180 was considered clinically significant.

All patients enrolled in this study met at least the following inclusion criteria: male or female, 18 to 65 years old;

primary headache disorder with 16 headache days per month by history and confirmed by diary during baseline, which could include any combination of migraines with or without aura, episodic/chronic tension-type headaches, and/or migrainous headaches (as defined by 1988 IHS criteria) (Headache Classification Subcommittee of the IHS, 1988);

willing and able to give written informed consent;

stable medical condition;

stable chronic medications, if any, including non-acute, prophylactic migraine medications, for at least 3 months immediately prior to Day −60;

willing and able to stay on current medications during the course of the study;

willing and able to complete the entire course of the study and to comply with study instructions, including diary phone system.

Figure 13:
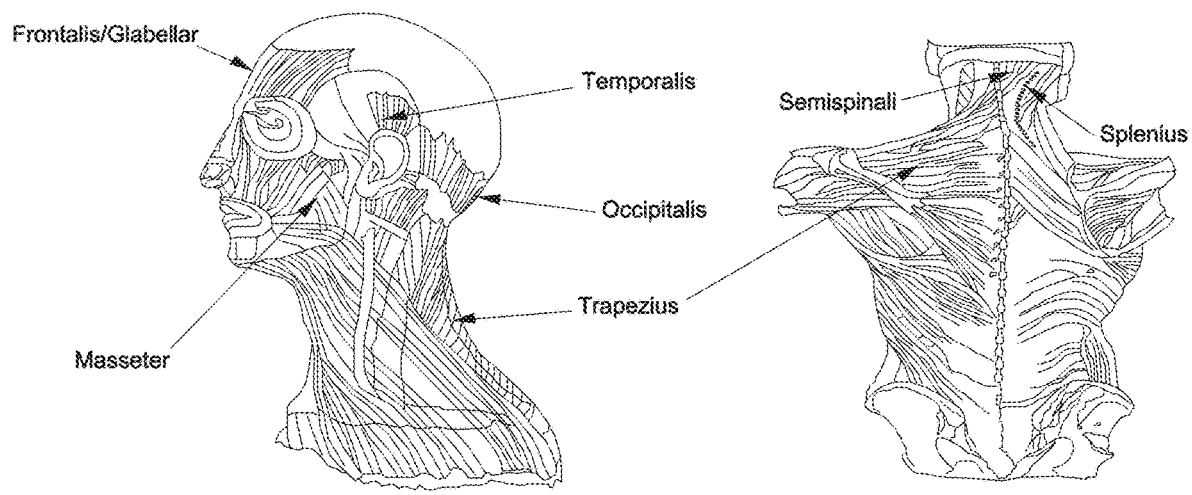
FIG. 13 comprises on the left side, a left side diagrammatic view of human muscle anatomy from the shoulders up, and on the right side a diagrammatic view of the back.

A dose range of units to be injected into each muscle area was defined, except for the occipitalis muscle where the dosage was fixed. The number of injection sites (total of 23 to 58 injection sites) within each specified muscle area (6 to 7 muscle areas) and dose injected (105 U to 260 U) was determined by the physician based on the pain distribution pattern and the severity of pain in the particular muscle area. Patients were to be injected in a minimum of 6 muscle areas, which included the frontal/glabellar, occipitalis, temporalis, semispinalis, splenius capitis, and trapezius muscles, as specified in Table 1 and FIG. 13. It was optional to inject the masseter muscle. Patients were to be injected with the same dose and in the same muscle areas and sites for treatments 1, 2, 3, and 4. Whenever possible, treatments for each patient were to be performed by the same physician throughout the study.

TABLE 1

Study Medication Dose and Injection Sites

| Muscle Area | Number of Units [a] | Bilateral Injection | Total Dose (U) |
|---|---|---|---|
| Frontal/Glabellar | 25-40 | No | 25-40 |
| Occipitalis | 10 | Yes | 20 |
| Temporalis | 10-25 | Yes | 20-50 |
| Masseter (optional) | 0-25 | Yes | 0-50 |
| Trapezius | 10-30 | Yes | 20-60 |
| Semispinalis | 5-10 | Yes | 10-20 |
| Splenius capitis | 5-10 | Yes | 10-20 |
| Total Dose Range | | | 105-260 |

Note:
Patients were injected with BOTOX® or placebo in the specified muscles with doses determined by the investigator.
[a] Patients randomized to the placebo group received 0 U of BOTOX®.

Each vial of BOTOX® contained 100 U of botulinum toxin type A, 0.5 mg albumin (human), and 0.9 mg sodium chloride in a sterile, vacuum-dried form without a preservative. Each vial of placebo contained 0.9 mg sodium chloride in a sterile, vacuum-dried form without a preservative. The vials were stored in a freezer between −20° C. and −5° C. before use. Directions for reconstitution with the diluent, 0.9% sterile saline (without preservatives), for injection were provided in the protocol.

In this study, in contrast to the fixed site/fixed dosage treatment approach used in previous studies, physicians were allowed to use a more individualized or patient-tailored treatment approach. Specifically, the number of injection sites (23 to 58 injection sites) within each specified muscle area (6 to 7 muscle areas) and dose injected (total dose of 105 to 260 U) was determined by the physician based on the patient's usual pain distribution pattern and the severity of pain in the particular muscle area.

During the course of the study, the protocols were amended to include a total of 3 treatment cycles (following the placebo run-in) and the primary endpoint was changed to Day 180 in the placebo non-responder stratum. By the time these amendments were put in place, a significant number of subjects had exited the original study at the planned Day 120 time point. Therefore, enrollment was extended to ensure that at least 90 placebo non-responder patients (45 per treatment group) were available for the Day 180 analysis.

The use of any concurrent medication (e.g., prescription or over-the-counter, including herbal remedies) was recorded on the patient's CRF along with the reason the medication was taken. In addition, medications that the patient had taken for treatment of his or her headaches since 7 days prior to Day −60 were recorded on the appropriate medication CRF. During the study, the patient was to report any use of concomitant medication for headache treatment using the electronic telephone daily diary.

Patients taking concurrent therapies were to maintain a stable dose and dose regimen during the study, particularly with regard to the use of non-acute, prophylactic migraine medications. Medications that were considered necessary for the patient's welfare could be given at the discretion of the investigator. The administration of all medications was to be reported on the CRFs.

Efficacy Measures

Patients recorded start/stop times of headaches, maximum and average severity of headaches, location and type of headache pain, effect on physical activity, presence of aura, presence of associated symptoms of headaches (nausea, vomiting, photo/phonophobia), and headache medications and doses used. The primary efficacy measure was the change from baseline in the frequency of headache-free days in a 30 day period. The primary visit for determination of efficacy was Day 180, with the evaluation reflecting the prior 30 day period. Baseline for the efficacy measures was defined as the frequency of headache-free days during the first 30 days of the screening period. A difference of 3 headache-free days between BOTOX® and placebo in the mean change from baseline in the frequency of headache-free days per 30-day period at Day 180 was considered clinically significant.

The secondary efficacy measure was the proportion of patients with a decrease from baseline of 50% or more in the frequency of headache days per 30-day period at Day 180. Other efficacy variables included the following:

proportion of patients with a decrease from baseline of 50% or more in the frequency of headaches per 30-day period;

frequency of headaches of any severity (per 30-day period);

frequency of migraine headaches of any severity (per 30-day period);
proportion of patients with a decrease from baseline of 50% or more in the frequency of migraine headaches per 30-day period;
proportion of patients with a decrease from baseline of 2 or more migraine headaches per 30-day period;
moderate to severe migraine headache frequency (per 30-day period);
patient's global assessment of response to treatment from baseline, as follows:
−4=very marked worsening (about 100% worse or greater)
−3=marked worsening (about 75% worse)
−2=moderate worsening (about 50% worse)
−1=slight worsening (about 25% worse)
0=unchanged
+1=slight improvement (about 25% improvement)
+2=moderate improvement (about 50% improvement)
+3=marked improvement (about 75% improvement)
+4=clearance of signs and symptoms (about 100% improvement) number of days per 30-day period with non-migraine headaches;
maximum and average headache severity (none, mild, moderate, severe);
number of days that acute headache medication was used during the study; and
number of uses (intakes) of acute headache mediation during the study.

Schedule of Assessments

The frequency and timing of study visits and measurements are outlined in Table 2 below.

TABLE 2

Schedule of Assessments

|  | Visit 1 (Baseline Day −60) | Visit 2 (Placebo Run-In/ Treatment 1) Day −30 | Visit 3 (Randomization/ Treatment 2) Day 0 | Visit 4 Day 30 | Visit 5 Day 60 | Visit 6 (Treatment 3) Day 90 | Visit 7 Day 120 | Visit 8 Day 150 | Visit 9 (Treatment 4) Day 180 | Visit 10 Day 210 | Visit 11 Day 240 | Visit 12 (Exit) Day 270 |
|---|---|---|---|---|---|---|---|---|---|---|---|---|
| View Video/Obtain Informed Consent | ✓ | | | | | | | | | | | |
| Inclusion/Exclusion Criteria | ✓ | ✓ | ✓ | | | | | | | | | |
| Review Medical and Medication History | ✓ | ✓ | ✓ | | | | | | | | | |
| Physical Examination | ✓ | | | | | | | | | | | ✓ |
| Vital Signs | ✓ | ✓ | ✓ | ✓ | ✓ | ✓ | ✓ | ✓ | ✓ | ✓ | ✓ | ✓ |
| Headache Diary Instructions and Review | ✓ | ✓ | ✓ | ✓ | ✓ | ✓ | ✓ | ✓ | ✓ | ✓ | ✓ | |
| Injection of Study Medication | | ✓ | ✓ | | | ✓ | | | ✓ | | | |
| Patient Global Assessment | | | ✓ | ✓ | ✓ | ✓ | ✓ | ✓ | ✓ | ✓ | ✓ | ✓ |
| Pain Diagram | ✓ | | | | | | | | | | | ✓ |
| Headache Count Recall | | | ✓ | ✓ | ✓ | ✓ | ✓ | ✓ | ✓ | ✓ | ✓ | ✓ |
| Beck Depression Inventory | ✓ | | | | | | | | | | | |
| Primary Chronic Headache Assessment | | | | | | | | | ✓ | | | |
| Treatment Assessment Questionnaire | | | | | | ✓ | | | ✓ | | | ✓ |
| MIDAS | ✓ | | | | | ✓ | | | ✓ | | | ✓ |
| Headache-Pain Specific Quality of Life Questionnaire | ✓ | | ✓ | | | ✓ | | | ✓ | | | ✓ |
| Headache Impact Questionnaire | ✓ | | ✓ | | | ✓ | | | ✓ | | | ✓ |
| SF-36 Health Survey | ✓ | | ✓ | | | ✓ | | | ✓ | | | ✓ |
| Medical Events | ✓ | ✓ | ✓ | | | | | | | | | |
| Adverse Events | | | ✓ | ✓ | ✓ | ✓ | ✓ | ✓ | ✓ | ✓ | ✓ | ✓ |
| Toxin Neutralizing Antibody Titer Blood Draw | ✓ | | | | | ✓ | | | ✓ | | | ✓ |

TABLE 2-continued

Schedule of Assessments

| | | | | | | | | | | | | |
|---|---|---|---|---|---|---|---|---|---|---|---|---|
| CBC/Blood Chemistry | ✓ | | | | | | | | | | | ✓ |
| Urine Pregnancy Test | | ✓ | ✓ | | ✓ | | | ✓ | | ✓ | | ✓ |
| Menstrual Cycle Data | ✓ | ✓ | ✓ | ✓ | ✓ | ✓ | ✓ | ✓ | ✓ | ✓ | ✓ | ✓ |

The primary efficacy variable was the change in the frequency of headache-free days from a 30 day baseline period (Day −60 to Day −31). Headache-free days in each 30 day period were determined from data recorded in the telephone electronic diary. Data recorded in the diaries included headache start date and time and headache stop date and time, and the following headache characteristics: usual headache pain (mild, moderate, severe); worst headache pain (mild, moderate, severe); side of the head (unilateral/bilateral); type of pain (pulsating/throbbing or pressing/squeezing); and effect of physical activity on pain (worse, not worse). It also included headache symptoms: aura (yes or no); interference of activities (yes or no); and other symptoms (nausea, vomiting, sensitivity to light [photophobia], sensitivity to noise [phonophobia]). The diary data also included acute medication taken for the headache (yes or no) and the name and dose of the medication.

Of the 571 patients screened and assessed over the Day −60 to Day −30 baseline period, 355 were enrolled/randomized at Day 0. At the end of the run-in period (Day 0), 279 patients were classified as placebo non-responders and 76 patients as placebo responders. Subsequently patients were randomized within each stratum (placebo no-responders and placebo responders) to receive either BOTOX® or placebo treatment. Within the placebo non-responder stratum, 134 patients received BOTOX® and 145 patients received placebo. Within the placebo responder stratum, 39 patients received BOTOX® and 37 patients received placebo. A total of 76.9% of patients (273/355) completed the study, including 132 patients who completed the original protocol requiring only 1 post-randomization treatment. Of the patients who discontinued early (22.8% [81/355]): 5.1% (18/355) for lack of efficacy, 1.4% (5/355) for adverse events, 0.3% (1/355) for inability to follow study instructions, 1.1% (4/355) for personal reasons, and 2.8% (10/355) were lost to follow up.

There were no significant differences between treatment groups in demographic characteristics. Overall, patients were 19 to 65 years of age (mean, 43.5 years), 84.5% (300/355) were female, and 87.9% (312/355) were Caucasian.

There were no significant differences between treatment groups in baseline characteristics (Table 3).

TABLE 3

Baseline Characteristics (As-Treated Population)

| Baseline Characteristic | BOTOX® 105 U to 260 U (N = 173) | Placebo (N = 182) | Total (N = 355) | P-value |
|---|---|---|---|---|
| Years since onset, mean (SD) | 14.8 (12.4) | 14.2 (12.5) | 14.5 (12.4) | 0.655 [a] |
| Age at onset, mean years (SD) | 27.5 (12.3) | 29.2 (13.6) | 28.4 (13.0) | 0.301 [a] |
| Frequency of migraines/probable migraines per 30 day period at baseline | 11.2 (6.6) | 10.8 (7.9) | 11.0 (7.3) | 0.274 |
| Use of prophylactic treatment, n (%) | 56 (32.4) | 71 (39.0) | 127 (35.8) | 0.192 [b] |
| Experience menstrual headaches, n (%) | 0 (0.0) | 0 (0.0) | 0 (0.0) | >0.999 [b] |
| Baseline MIDAS score, mean (SD) | 55.3 (49.6) | 59.8 (59.6) | 57.6 (55.0) | 0.997 [a] |
| Baseline Beck Depression Inventory score, mean (SD) | 7.8 (6.9) | 7.9 (6.8) | 7.8 (6.9) | 0.847 [a] |
| Mean total dose for the second treatment cycle | 190.8 U | NA | NA | NA |

SD = standard deviation,
NA = not applicable,
MIDAS = Migraine Disability Assessment,
[a] P-values for treatment comparisons from the Wilcoxon rank-sum test.
[b] P-values for treatment comparisons from Pearson's chi-square or Fisher's exact tests.

The most common locations where head pain historically started and ended, as reported by patients at baseline, are presented in Table 4.

TABLE 4

Location where Headache Pain Historically Starts and Ends Reported at Baseline (Number (%) of Patients)

| Location | BOTOX® 105 U to 260 U (N = 173) | Placebo (N = 182) | Total (N = 355) | P-value |
|---|---|---|---|---|
| Historical Location Where Pain Starts | | | | |
| Frontal/glabellar | 125 (72.7) | 140 (76.9) | 265 (74.9) | 0.357 |
| Temporalis | 100 (58.1) | 114 (62.6) | 214 (60.5) | 0.387 |
| Occipitalis | 80 (46.5) | 85 (46.7) | 165 (46.6) | 0.971 |
| Historical Location Where Pain Ends | | | | |
| Frontal/glabellar | 123 (71.9) | 145 (79.7) | 268 (75.9) | 0.089 |
| Temporalis | 98 (57.3) | 113 (62.1) | 211 (59.8) | 0.360 |
| Occipitalis | 97 (56.7) | 111 (61.0) | 208 (58.9) | 0.416 |

Figure 14:
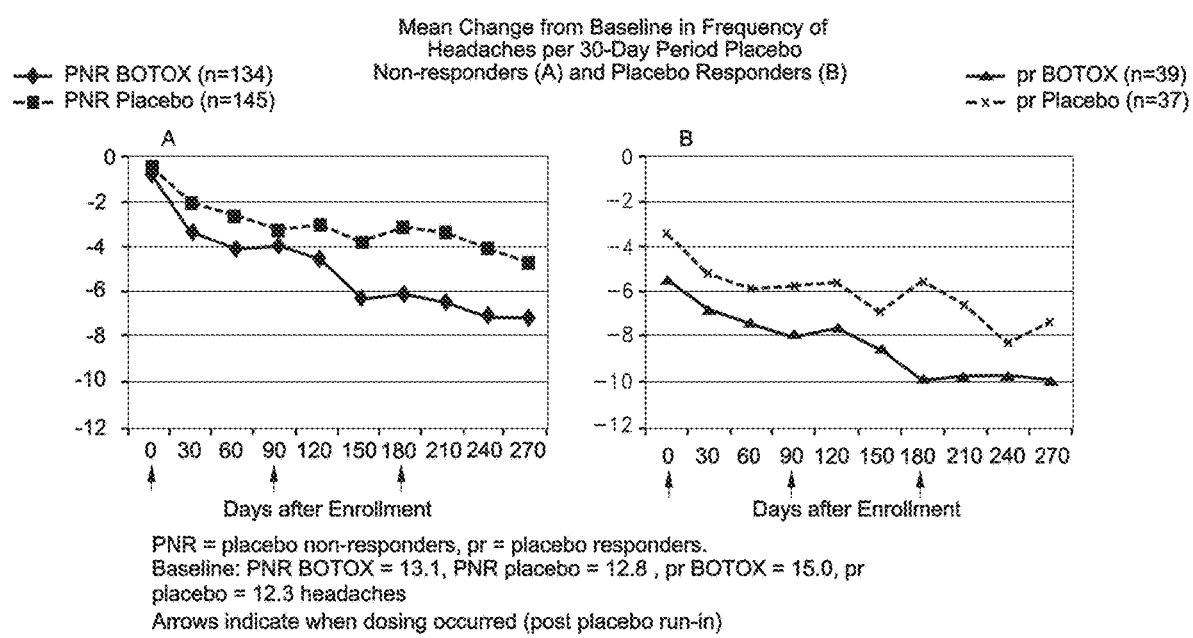
FIG. 14 comprises two graphs which show the mean change from baseline in the frequency of headaches per 30-day period for placebo non-responders (A) and responders (B).

In the analyses of the frequency of headaches per 30 day period, a statistically significant change in the frequency of headaches per 30 day period was observed at Days 30, 60, 150, 180, 210, and 240 for placebo non-responders and at Day 180 for placebo responders (Table 5). FIG. 14 presents the mean baseline and the mean changes from baseline in the frequency of headaches per 30-day period for placebo non-responders and placebo responders.

TABLE 5

Mean (Standard Deviation) at Baseline and Change from Baseline in the Frequency of Headaches per 30-Day Period for Placebo Non-responders and Placebo Responders

| Time Period | Placebo Non-Responders | | | Placebo Responders | | |
|---|---|---|---|---|---|---|
| | BOTOX® (N = 134) | Placebo (N = 145) | p-value [a] | BOTOX® (N = 39) | Placebo (N = 37) | p-value [a] |
| Baseline | 13.1 (8.4) | 12.8 (9.0) | 0.780 | 15.0 (5.0) | 12.3 (4.9) | 0.021 |
| Treatment 1: Placebo (followed by a 30-day run-in period) | | | | | | |
| Treatment 2 | | | | | | |
| Day 30 | −3.3 (5.0) | −2.0 (4.8) | 0.028 | −6.7 (6.5) | −5.2 (4.7) | 0.705 |
| Day 60 | −4.1 (5.5) | −2.6 (5.3) | 0.018 | −7.4 (5.7) | −5.8 (4.4) | 0.855 |
| Day 90 | −3.9 (5.6) | −3.2 (5.9) | 0.307 | −8.0 (6.3) | −5.7 (4.5) | 0.534 |
| Treatment 3 | | | | | | |
| Day 120 | −4.6 (5.2) | −3.0 (6.3) | 0.118 | −7.6 (5.2) | −5.6 (3.3) | 0.412 |
| Day 150 | −6.3 (6.0) | −3.8 (6.2) | 0.039 | −8.5 (5.3) | −6.9 (4.6) | 0.851 |
| Day 180 | −6.1 (5.5) | −3.1 (6.8) | 0.013 | −9.9 (4.9) | −5.6 (2.8) | 0.013 |
| Treatment 4 | | | | | | |
| Day 210 | −6.5 (6.9) | −3.4 (7.0) | 0.021 | −9.7 (5.8) | −6.6 (4.9) | 0.259 |
| Day 240 | −7.1 (7.3) | −4.1 (6.5) | 0.035 | −9.7 (6.1) | −8.2 (4.5) | 0.948 |
| Day 270 | −7.2 (7.4) | −4.7 (7.3) | 0.172 | −9.9 (4.7) | −7.4 (5.4) | 0.488 |

Source: Tables 14.2-12.3 and 14.2-12.4.

[a] Between treatment comparison from Wilcoxon rank-sum test.

In the analyses of other protocol-designated efficacy variables, there were statistically significant differences between BOTOX® and placebo in the placebo non-responder and placebo responder groups. Additionally, subgroups of patients were identified for which there was a consistently better response to BOTOX® than to placebo.

Frequency of Headaches, Pooled Population

Figure 15:
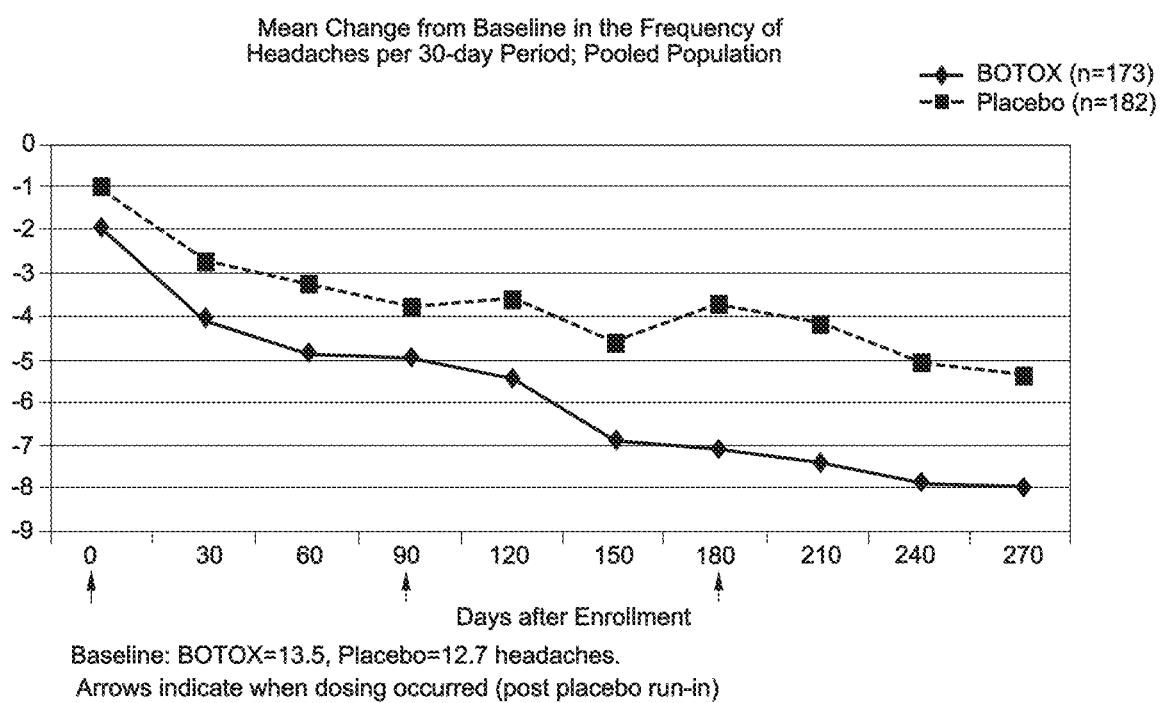
FIG. 15 shows the mean change from baseline in the frequency of headaches per 30-day period, for a pooled population of patients.

A statistically significant change in the frequency of headaches per 30-day period was observed at multiple time points (Days 30, 60, 150, 180, 210, and 240) (Table 6). FIG. 15 presents the mean baseline and the mean changes from baseline in the frequency of headaches per 30-day period. The analysis of frequency of headaches demonstrated statistically significant differences between BOTOX® and placebo that favored BOTOX®.

TABLE 6

Mean (Standard Deviation) at Baseline and Change from Baseline in the Frequency of Headaches per 30-Day Period; Pooled Population

| Time Period | BOTOX® N = 173 | Placebo N = 182 | p-value [a] |
|---|---|---|---|
| Baseline | 13.5 (7.7) | 12.7 (8.3) | 0.339 |
| Treatment 1: Placebo (followed by a 30-day run-in period) | | | |
| Post Placebo Run-in | −1.9 (4.7) | −1.0 (4.0) | 0.336 |
| Treatment 2 | | | |
| Day 30 | −4.1 (5.6) | −2.7 (4.9) | 0.021 |
| Day 60 | −4.8 (5.7) | −3.2 (5.3) | 0.010 |
| Day 90 | −4.9 (6.0) | −3.7 (5.7) | 0.135 |
| Treatment 3 | | | |
| Day 120 | −5.4 (5.3) | −3.6 (5.8) | 0.061 |
| Day 150 | −6.9 (5.8) | −4.6 (6.0) | 0.033 |
| Day 180 | −7.1 (5.6) | −3.7 (6.1) | 0.001 |
| Treatment 4 | | | |
| Day 210 | −7.4 (6.7) | −4.2 (6.7) | 0.005 |
| Day 240 | −7.9 (7.0) | −5.1 (6.3) | 0.035 |
| Day 270 | −8.0 (6.8) | −5.4 (7.0) | 0.080 |

[a] Between treatment comparison from Wilcoxon rank-sum test.

As seen in Table 6 and FIG. 15, the time of the first statistically significant difference between treatment groups in the frequency of headaches per 30-day period was at 30 days after the first treatment following placebo run-in. At this time point, there was a significant difference (p=0.021) between BOTOX® and placebo demonstrating a rapid onset of effect. The mean changes from baseline were −4.1 for BOTOX® and −2.7 for placebo.

TABLE 7

Number (Percentage) of Patients with a Decrease from Baseline of 50% or More Headaches per 30-Day Period; Pooled Population

| Time Period | BOTOX® | Placebo | p-value [a] |
|---|---|---|---|
| Treatment 1: Placebo (followed by a 30 day run-in period) | | | |
| Post Placebo Run-in | 23/173 (13.3) [b] | 20/182 (11.0) | 0.506 |
| Treatment 2 | | | |
| Day 30 | 45/172 (26.2) | 47/182 (25.8) | 0.942 |
| Day 60 | 60/164 (36.6) | 49/166 (29.5) | 0.172 |
| Day 90 | 54/149 (36.2) | 49/157 (31.2) | 0.352 |
| Treatment 3 | | | |
| Day 120 | 33/80 (41.3) | 28/82 (34.1) | 0.351 |
| Day 150 | 38/75 (50.7) | 33/80 (41.3) | 0.240 |
| Day 180 | 39/72 (54.2) | 30/79 (38.0) | 0.046 |
| Treatment 4 | | | |
| Day 210 | 40/70 (57.1) | 28/77 (36.4) | 0.012 |
| Day 240 | 39/70 (55.7) | 32/71 (45.1) | 0.206 |
| Day 270 | 40/69 (58.0) | 38/69 (55.1) | 0.731 |

[a] Between treatment comparison from Person's chi square test or Fisher's exact test.
[b] Number of patients with response/number of patients evaluated at time period (percentage).

Table 8 presents the mean baseline and the mean changes from baseline in the frequency of headaches per 30-day period for patients who completed 2 and 3 treatment cycles after the placebo run-in period. The 138 patients (69 BOTOX®, 69 placebo) who completed 3 treatment cycles had a sustained response to treatment. Over the 270 day treatment period the response to treatment with BOTOX® generally continued to improve while the response to treatment with placebo remained relatively stable.

TABLE 8

Mean (Standard Deviation) at Baseline and Change from Baseline in the Frequency of Headaches per 30-Day Period for Patients Who Completed 2 or 3 Injection Cycles After the Placebo Run-in; Pooled Population

| | Completed 2 Treatment Cycles After Placebo Run-in | | | Completed 3 Treatment Cycles After Placebo Run-in | | |
|---|---|---|---|---|---|---|
| Time Period | BOTOX® N = 72 | Placebo N = 79 | p-value [a] | BOTOX® N = 69 | Placebo N = 69 | p-value [a] |
| Baseline | 14.3 (7.5) | 12.8 (8.3) | 0.183 | 14.4 (7.5) | 12.6 (8.1) | 0.136 |
| Treatment 1: Placebo (followed by a 30-day run-in period) | | | | | | |
| Treatment 2 | | | | | | |
| Day 30 | −4.7 (5.3) | −3.4 (5.0) | 0.072 | −4.7 (5.4) | −3.4 (5.1) | 0.098 |
| Day 60 | −5.3 (5.3) | −3.5 (5.4) | 0.037 | −5.3 (5.4) | −3.7 (5.6) | 0.091 |
| Day 90 | −4.8 (5.6) | −3.5 (5.6) | 0.198 | −4.7 (5.7) | −3.4 (5.8) | 0.229 |
| Treatment 3 | | | | | | |
| Day 120 | −5.8 (5.2) | −3.6 (5.8) | 0.023 | −5.7 (5.2) | −3.6 (6.0) | 0.036 |
| Day 150 | −6.8 (5.8) | −4.5 (5.9) | 0.042 | −6.8 (5.9) | −4.5 (6.1) | 0.056 |
| Day 180 | −7.1 (5.6) | −3.7 (6.1) | 0.001 | −7.1 (5.6) | −3.7 (6.3) | 0.001 |
| Treatment 4 | | | | | | |
| Day 210 | −7.4 (6.8) | −4.2 (6.7) | 0.008 | −7.5 (6.7) | −3.9 (6.8) | 0.004 |
| Day 240 | −7.9 (7.1) | −5.1 (6.3) | 0.030 | −7.9 (7.0) | −5.0 (6.3) | 0.025 |
| Day 270 | −8.0 (6.8) | −5.4 (7.0) | 0.041 | −8.0 (6.8) | −5.4 (7.0) | 0.042 |

[a] Between treatment comparison from a Wilcoxon rank-sum test.

TABLE 9

Mean Baseline and Change from Baseline in the Frequency of Headaches for Headaches of a Durations ≥4 Hours and <4 Hours per 30-Day Period

| | Headaches of a Duration ≥4 Hours | | | Headaches of a Duration <4 Hours | | |
|---|---|---|---|---|---|---|
| Time Period | BOTOX® N = 173 | Placebo N = 182 | p-value [a] | BOTOX® N = 173 | Placebo N = 182 | p-value [a] |
| Baseline | 9.6 | 9.2 | 0.186 | 3.9 | 3.5 | 0.488 |
| Treatment 1: Placebo (followed by a 30-day run-in period) | | | | | | |
| Treatment 2 | | | | | | |
| Day 30 | −2.9 | −1.2 | 0.001 | −1.2 | −1.5 | 0.307 |
| Day 60 | −3.4 | −1.9 | 0.017 | −1.4 | −1.3 | 0.784 |
| Day 90 | −3.3 | −2.0 | 0.024 | −1.6 | −1.7 | 0.848 |
| Treatment 3 | | | | | | |
| Day 120 | −3.8 | −2.0 | 0.013 | −1.6 | −1.6 | 0.867 |
| Day 150 | −4.8 | −2.8 | 0.044 | −2.0 | −1.8 | 0.906 |
| Day 180 | −4.6 | −2.2 | 0.005 | −2.5 | −1.6 | 0.134 |
| Treatment 4 | | | | | | |
| Day 210 | −5.1 | −2.4 | 0.003 | −2.3 | −1.7 | 0.688 |
| Day 240 | −5.1 | −3.0 | 0.016 | −2.7 | −2.1 | 0.309 |
| Day 270 | −5.5 | −3.1 | 0.013 | −2.4 | −2.2 | 0.872 |

[a] Between treatment comparison from a Wilcoxon rank-sum test.

Table 9 presents the mean baseline and the mean changes from baseline in the number of headaches with a duration ≥4 hours and <4 hours per 30-day period. Over the 270-day treatment period, in headaches ≥4 hours in duration, the changes from baseline headache count were significantly greater for BOTOX® than for placebo at every return visit (p≤0.044; Table 14.5-325). A significant difference between the groups was not seen at any return visit for headaches <4 hours in duration.

Efficacy variables for which there were clinically meaningful differences between BOTOX® and placebo in this subpopulation subgroup included: a 50% reduction from baseline in the frequency of headaches per 30-day period; a 30% reduction from baseline in the frequency of headaches per 30-day period; frequency of migraines or probable migraines per 30-day period; and, number of days and number of uses of acute analgesic headache medication per 30-day period.

TABLE 10

Baseline Characteristics of Patients Using and Not Using Prophylactic Headache Medications at Baseline; Pooled Population

| | Prophylactic Headache Medications at Baseline | | | | | |
|---|---|---|---|---|---|---|
| | No | | | Yes | | |
| Baseline Characteristic | BOTOX® (N = 117) | Placebo (N = 111) | P-Value | BOTOX® (N = 56) | Placebo (N = 71) | P-Value |
| Age, mean years (SD) | 42.2 (10.4) | 42.5 (11.5) | 0.978 [a] | 44.4 (8.5) | 46.5 (10.3) | 0.232 [a] |
| Sex, n (%) | | | | | | |
| Male | 11 (9.4) | 22 (19.8) | 0.025 [b] | 11 (19.6) | 11 (15.5) | 0.540 [b] |
| Female | 106 (90.6) | 89 (80.2) | | 45 (80.4) | 60 (84.5) | |
| Race, n (%) | | | | | | |
| Caucasian | 102 (87.2) | 93 (83.8) | 0.466 [b] | 52 (92.9) | 65 (91.5) | >0.999 [b] |
| Non-Caucasian | 15 (12.8) | 18 (16.2) | | 4 (7.1) | 6 (8.5) | |
| Years since onset, mean (SD) | 15.3 (13.2) | 14.3 (12.8) | 0.656 [a] | 13.8 (10.7) | 14.2 (12.1) | 0.864 [a] |
| Age at onset, mean years (SD) | 26.2 (12.2) | 27.6 (13.1) | 0.562 [a] | 30.1 (12.1) | 31.8 (13.9) | 0.407 [a] |
| Prophylactic headache medications, n (%) | | | | | | |
| Beta blockers | NA | NA | NA | 16 (28.6) | 21 (29.6) | 0.901 |
| Calcium channel blockers | NA | NA | NA | 9 (16.1) | 18 (25.4) | 0.204 |

TABLE 10-continued

Baseline Characteristics of Patients Using and Not Using Prophylactic Headache Medications at Baseline; Pooled Population

| | Prophylactic Headache Medications at Baseline | | | | | |
|---|---|---|---|---|---|---|
| | No | | | Yes | | |
| Baseline Characteristic | BOTOX® (N = 117) | Placebo (N = 111) | P-Value | BOTOX® (N = 56) | Placebo (N = 71) | P-Value |
| Anticonvulsants | NA | NA | NA | 23 (41.1) | 27 (38.0) | 0.727 |
| Antidepressants | NA | NA | NA | 31 (55.4) | 43 (60.6) | 0.555 |
| Baseline MIDAS score, mean (SD) | 54.0 (44.4) | 55.7 (60.3) | 0.302 [a] | 58.0 (59.7) | 66.1 (58.8) | 0.264 [a] |
| Baseline Beck Depression Inventory score, mean (SD) | 6.9 (6.6) | 7.3 (7.0) | 0.945 [a] | 9.5 (7.4) | 8.6 (6.4) | 0.739 [a] |

SD = standard deviation,
NA = not applicable,
NC = not computed.
[a] P-values for treatment comparisons from the Wilcoxon rank-sum test.
[b] P-values for treatment comparisons from Pearson's chi-square or Fisher's exact tests.

Figure 16:
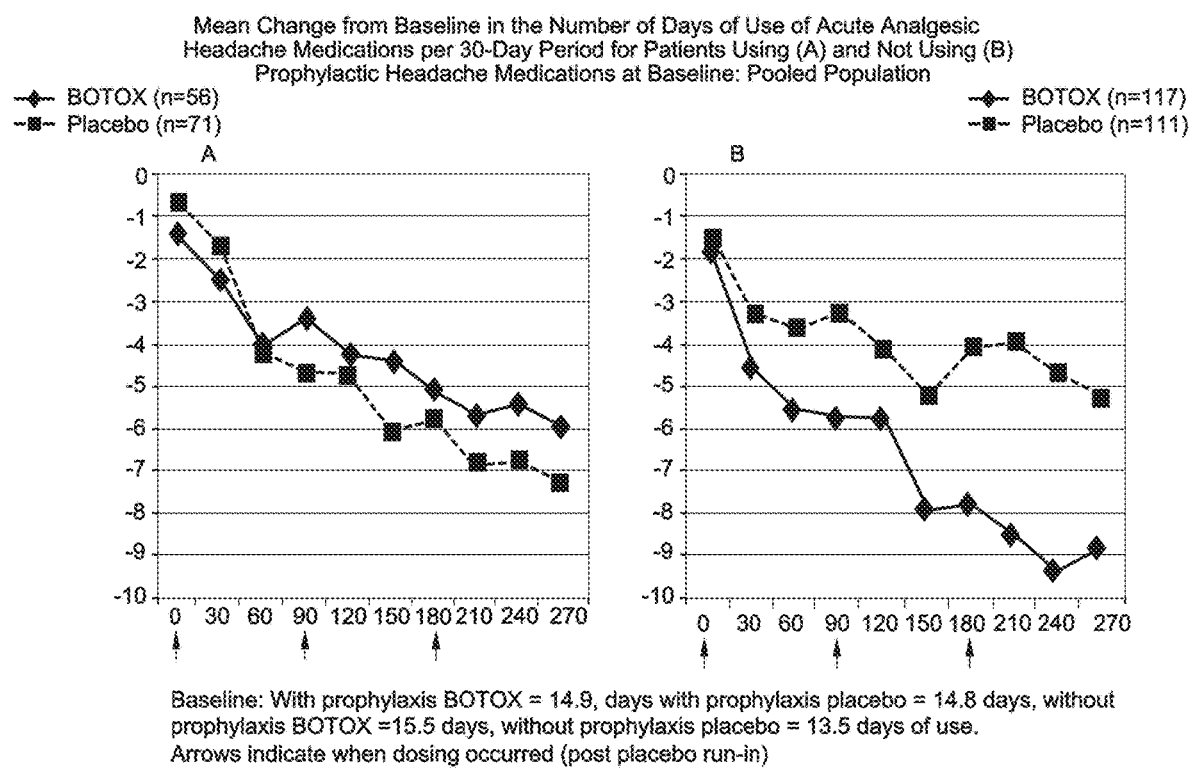
FIG. 16 comprises two graphs which show mean change from baseline in the number of days of use of acute analgesic headache medications per 30-day period for patients using (graph A) and not using (graph B) prophylactic headache medications at baseline, for a pooled population of patients.

The mean baseline and mean changes from baseline to each assessment time point in the frequency of headache days per 30-day period are presented in Table 11 and FIG. 16 for the populations of patients using and not using prophylactic headache medications at baseline. The types of prophylactic headache medications used at baseline included beta blockers, calcium channel blockers, anticonvulsants, and antidepressants (excluding serotonin uptake inhibitors [e.g., PROSAC®] since there is no evidence of any effect in headache for this class).

TABLE 11

Mean (Standard Deviation) at Baseline and Change from Baseline in the Frequency of Headaches per 30-Day Period by Use of Prophylactic Headache Medications at Baseline; Pooled Population

| | Use of Prophylactic Headache Medications at Baseline | | | | | |
|---|---|---|---|---|---|---|
| | Yes | | | No | | |
| Time Period | BOTOX® N = 56 | Placebo N = 71 | p-value [a] | BOTOX® N = 117 | Placebo N = 111 | p-value [a] |
| Baseline | 12.4 (7.5) | 12.5 (8.6) | 0.855 | 14.1 (7.9) | 12.9 (8.2) | 0.205 |
| Treatment 1: Placebo (followed by a 30-day run-in period) | | | | | | |
| Treatment 2 | | | | | | |
| Day 30 | −2.8 (4.1) | −2.8 (3.7) | 0.887 | −4.7 (6.1) | −2.5 (5.6) | 0.004 |
| Day 60 | −3.5 (4.4) | −3.5 (4.6) | 0.836 | −5.5 (6.1) | −3.0 (5.7) | 0.005 |
| Day 90 | −3.6 (5.0) | −4.8 (4.9) | 0.201 | −5.6 (6.3) | −3.0 (6.1) | 0.011 |
| Treatment 3 | | | | | | |
| Day 120 | −5.3 (4.3) | −4.0 (4.9) | 0.255 | −5.5 (6.0) | −3.3 (6.5) | 0.072 |
| Day 150 | −5.7 (5.1) | −4.7 (5.3) | 0.564 | −7.8 (6.2) | −4.5 (6.6) | 0.032 |
| Day 180 | −6.6 (5.0) | −3.9 (4.7) | 0.030 | −7.5 (6.0) | −3.6 (7.3) | 0.007 |
| Treatment 4 | | | | | | |
| Day 210 | −6.7 (5.5) | −4.7 (5.1) | 0.138 | −7.9 (7.4) | −3.7 (7.9) | 0.023 |
| Day 240 | −6.6 (6.0) | −5.0 (5.5) | 0.279 | −8.7 (7.6) | −5.1 (7.1) | 0.062 |
| Day 270 | −6.9 (6.3) | −5.2 (5.5) | 0.369 | −8.8 (7.1) | −5.6 (8.1) | 0.062 |

[a] Between treatment comparison from a Wilcoxon rank-sum test.

For patients using antidepressants at baseline (31 BOTOX®, 43 placebo) there were no statistically significant differences between treatment groups at any time point, except at Day 210 (p=0.048), in the change from baseline in the frequency of headaches per 30-day period. From Day 120 through Day 270, the mean decrease from baseline was greater for BOTOX® by 1.6 to 3.7 headaches per 30-day period. For patients not using antidepressants at baseline, from Day 60 through Day 270, the mean decrease from baseline was greater for BOTOX® by 1.7 to 3.6 headaches per 30-day period. The changes from baseline were significantly greater (p<0.020) for BOTOX® at Days 30, 60, and 180.

The percentages of patients at each assessment time point with at least a 50% decrease from baseline in the frequency of headaches per 30-day period (defined as a responder) are presented in Table 12 for patients using and not using prophylactic headache medications at baseline.

For patients using prophylactic headache medications at baseline, there were no statistically significant differences between BOTOX® and placebo. For patients not using prophylactic headache medications at baseline, from Day 150 through Day 270 at least 50% of BOTOX®-treated patients were responders. The differences between BOTOX® and placebo were statistically significant at Days 150 and 210. At these time points, the response rate for BOTOX® was greater than the response rate for placebo by at least 20%.

TABLE 12

Number (Percentage) of Patients with a Decrease
from Baseline of 50% or More
Headaches per 30-Day Period by Use of Prophylactic
Headache Medications at Baseline; Pooled Population

| | Using Prophylactic Headache Medications at Baseline | | | | | |
|---|---|---|---|---|---|---|
| | Yes | | | No | | |
| Time Period | BOTOX® N = 56 | Placebo N = 71 | p-value [a] | BOTOX® N = 117 | Placebo N = 111 | p-value [a] |
| Treatment 1: Placebo (followed by a 30-day run-in period) | | | | | | |
| Post Placebo Run-in | 4/56 (7.1%) [b] | 7/71 (9.9%) | 0.754 | 19/117 (16.2%) | 13/111 (11.7%) | 0.325 |
| Treatment 2 | | | | | | |
| Day 30 | 10.56 (17.9%) | 17/71 (23.9%) | 0.405 | 35/116 (30.2%) | 30/111 (27.0%) | 0.600 |
| Day 60 | 15/54 (27.8%) | 20/66 (30.3%) | 0.762 | 45/110 (40.9%) | 29/100 (29.0%) | 0.071 |
| Day 90 | 15/53 (28.3%) | 22/63 (34.9%) | 0.446 | 39/96 (40.6%) | 27/94 (28.7%) | 0.085 |
| Treatment 3 | | | | | | |
| Day 120 | 17/34 (50.0%) | 17/39 (43.6%) | 0.584 | 16/46 (34.8%) | 11/43 (25.6%) | 0.345 |
| Day 150 | 13/30 (43.3%) | 19/38 (50.0%) | 0.584 | 25/45 (55.6%) | 14/42 (33.3%) | 0.037 |
| Day 180 | 16/28 (57.1%) | 15/38 (39.5%) | 0.155 | 23/44 (52.3%) | 15/41 (36.6%) | 0.146 |
| Treatment 4 | | | | | | |
| Day 210 | 18/29 (62.1%) | 17/38 (44.7%) | 0.159 | 22/41 (53.7%) | 11/39 (28.2%) | 0.021 |
| Day 240 | 18/29 (62.1%) | 17/35 (48.6%) | 0.280 | 21/41 (51.2%) | 15/36 (41.7%) | 0.402 |
| Day 270 | 16/29 (55.2%) | 19/33 (57.6%) | 0.849 | 24/40 (60.0%) | 19/36 (52.8%) | 0.526 |

[a] Between treatment comparison from Person's chi-square test or Fisher's exact test.
[b] Number of patients with response/number of patients evaluated at time period (percentage).

The percentages of patients at each assessment time point with at least a 30% decrease from baseline in the frequency of headaches per 30-day period are presented in Table 13 for patients using and not using prophylactic headache medications at baseline.

For patients using prophylactic headache medications at baseline, there were no statistically significant differences between BOTOX® and placebo. For patients not using prophylactic headache medications at baseline, from Day 30 through Day 270 at least 50% of BOTOX®-treated patients had at least a 30% decrease in the frequency of headaches per 30-day period. The differences between BOTOX® and placebo were statistically significant at Days 30, 60, 150, 180, and 210. At these time points, the response rates for BOTOX® was greater than the response rates for placebo by 16.4 to 26.2%.

TABLE 13

Number (Percentage) of Patients with a Decrease from Baseline of 30%
or More Headaches per 30-Day Period by Use of Prophylactic
Headache Medications at Baseline; Pooled Population

| | Use of Prophylactic Headache Medications at Baseline | | | | | |
|---|---|---|---|---|---|---|
| | Yes | | | No | | |
| Time Period | BOTOX® | Placebo | p-value [a] | BOTOX® | Placebo | p-value [a] |
| Treatment 1: Placebo (followed by a 30-day run-in period) | | | | | | |
| Post Placebo Run-in | 15/56 (26.8%) | 18/71 (25.4%) | 0.855 | 24/117 (20.5%) | 29/111 (26.1%) | 0.316 |
| Treatment 2 | | | | | | |
| Day 30 | 21/56 (37.5%) | 28/71 (39.4%) | 0.824 | 61/116 (52.6%) | 40/111 (36.0%) | 0.012 |
| Day 60 | 25/54 (46.3%) | 28/66 (42.4%) | 0.671 | 62/110 (56.4%) | 40/100 (40.0%) | 0.018 |
| Day 90 | 21/53 (39.6%) | 36/63 (57.1%) | 0.060 | 59/96 (61.5%) | 47/94 (50.0%) | 0.112 |
| Treatment 3 | | | | | | |
| Day 120 | 20/34 (58.8%) | 23/39 (59.0%) | 0.990 | 26/46 (56.5%) | 20/43 (46.5%) | 0.345 |
| Day 150 | 18/30 (60.0%) | 26/38 (68.4%) | 0.471 | 35/45 (77.8%) | 24/42 (57.1%) | 0.040 |
| Day 180 | 20/28 (71.4%) | 24/38 (63.2%) | 0.481 | 33/44 (75.0%) | 20/41 (48.8%) | 0.013 |
| Treatment 4 | | | | | | |
| Day 210 | 23/29 (79.3%) | 22/38 (57.9%) | 0.064 | 28/41 (68.3%) | 18/39 (46.2%) | 0.045 |
| Day 240 | 22/29 (75.9%) | 23/35 (65.7%) | 0.376 | 31/41 (75.6%) | 22/36 (61.1%) | 0.171 |
| Day 270 | 20/29 (69.0%) | 23/33 (69.7%) | 0.950 | 30/40 (75.0%) | 23/36 (63.9%) | 0.292 |

[a] Between treatment comparison from Person's chi-square test.

Analyses of the frequency of headaches per 30-day period for patients who were 10 to 20 years and >20 years since disease onset are given in Table 14. The response to BOTOX® was consistently better than the response to placebo over the entire treatment period for patients with disease onset of 10 to 20 years with a statistically significant difference only at Day 180 and for patients with disease onset of >20 years with statistically significant differences at Days 30, 60, and 210. Of note is the observation that for the >20 years subgroup of patients the response to placebo treatment was consistently and considerably lower compared with the response to treatment for the 10 to 20 years subgroup of patients.

TABLE 14

Mean (Standard Deviation) Baseline and Change
from Baseline in the Frequency of Headaches
per 30-Day Period by Time From Disease Onset
(10 to 20 and >20 Years); Pooled Population

| | Disease Onset 10 to 20 Years | | | Disease Onset >20 Years | | |
|---|---|---|---|---|---|---|
| Time Period | BOTOX® N = 53 | Placebo N = 53 | p-value [a] | BOTOX® N = 46 | Placebo N = 48 | p-value [a] |
| Baseline | 13.2 (7.1) | 11.5 (8.1) | 0.170 | 14.1 (7.9) | 14.2 (9.5) | 0.931 |
| Treatment 1: Placebo (followed by a 30-day run-in period) | | | | | | |
| Treatment 2 | | | | | | |
| Day 30 | −3.6 (5.0) | −3.4 (5.1) | 0.472 | −4.7 (5.0) | −1.9 (4.2) | 0.014 |
| Day 60 | −4.9 (5.0) | −4.1 (4.9) | 0.269 | −5.8 (5.8) | −1.8 (5.2) | 0.003 |
| Day 90 | −4.9 (5.6) | −4.4 (4.9) | 0.693 | −5.4 (5.4) | −2.8 (6.2) | 0.078 |

TABLE 14-continued

Mean (Standard Deviation) Baseline and Change
from Baseline in the Frequency of Headaches
per 30-Day Period by Time From Disease Onset
(10 to 20 and >20 Years); Pooled Population

| | Disease Onset 10 to 20 Years | | | Disease Onset >20 Years | | |
|---|---|---|---|---|---|---|
| Time Period | BOTOX® N = 53 | Placebo N = 53 | p-value[a] | BOTOX® N = 46 | Placebo N = 48 | p-value[a] |
| Treatment 3 | | | | | | |
| Day 120 | −6.2 (5.8) | −4.5 (5.3) | 0.205 | −6.1 (4.7) | −2.5 (6.3) | 0.107 |
| Day 150 | −7.7 (6.2) | −5.7 (5.1) | 0.244 | −6.3 (5.1) | −3.5 (6.6) | 0.146 |
| Day 180 | −8.1 (6.4) | −4.8 (5.2) | 0.045 | −6.1 (4.6) | −2.3 (6.3) | 0.055 |
| Treatment 4 | | | | | | |
| Day 210 | −8.3 (6.8) | −6.4 (5.7) | 0.256 | −6.7 (6.9) | −1.4 (6.9) | 0.025 |
| Day 240 | −8.2 (6.7) | −6.1 (5.6) | 0.278 | −8.1 (7.8) | −3.4 (6.7) | 0.074 |
| Day 270 | −7.4 (6.2) | −6.3 (6.1) | 0.481 | −8.8 (8.5) | −4.8 (6.9) | 0.209 |

[a] Between treatment comparison from a Wilcoxon rank-sum test.

Analyses of the frequency of headaches per 30-day period by headache-day frequency at baseline (20 to 24 and 25 to 30 headache-days) are summarized in Table 15. The response to BOTOX® was consistently better than the response to placebo over the entire treatment period for patients with a baseline headache-day frequency of 20 to 24 with statistically significant differences at Days 60 and 180, and for patients with a baseline headache-day frequency of 25 to 30 with statistically significant differences at Days 30, 60, and 180. At each time point, the difference between the mean changes for BOTOX® and placebo were greater for patients with a baseline headache-day frequency of 25 to 30.

TABLE 15

Mean (Standard Deviation) at Baseline and Change from Baseline in
the Frequency of Headaches per 30-Day Period
for Patients with Headache-Day Frequency of 20 to
24 and 25 to 30 per 30-Day Period at Baseline; Pooled Population

| | Headache-Day Frequency of 20 to 24 Per 30-Day Period | | | Headache-Day Frequency of 25 to 30 Per 30-Day Period | | |
|---|---|---|---|---|---|---|
| Time Period | BOTOX® N = 53 | Placebo N = 54 | p-value[a] | BOTOX® N = 70 | Placebo N = 81 | p-value[a] |
| Baseline | 16.6 (5.9) | 14.8 (6.3) | 0.127 | 11.5 (10.0) | 11.5 (10.7) | 0.769 |
| Treatment 1: Placebo (followed by a 30-day run-in period) | | | | | | |
| Treatment 2 | | | | | | |
| Day 30 | −5.7 (5.1) | −4.2 (5.4) | 0.248 | −3.5 (6.4) | −1.2 (4.5) | 0.014 |
| Day 60 | −6.9 (5.7) | −4.7 (5.6) | 0.036 | −3.9 (6.2) | −1.4 (4.9) | 0.015 |
| Day 90 | −6.5 (6.1) | −4.6 (5.7) | 0.158 | −4.0 (6.4) | −2.9 (5.9) | 0.318 |
| Treatment 3 | | | | | | |
| Day 120 | −6.9 (5.9) | −4.6 (6.1) | 0.166 | −4.1 (5.7) | −2.5 (5.9) | 0.154 |
| Day 150 | −9.0 (6.0) | −6.4 (5.7) | 0.137 | −6.2 (6.5) | −2.7 (5.6) | 0.059 |
| Day 180 | −8.9 (6.0) | −5.0 (6.0) | 0.038 | −6.0 (6.0) | −2.5 (5.8) | 0.019 |
| Treatment 4 | | | | | | |
| Day 210 | −9.6 (7.4) | −6.3 (6.1) | 0.064 | −6.5 (7.6) | −2.4 (6.1) | 0.104 |
| Day 240 | −10.1 (7.2) | −6.8 (5.5) | 0.125 | −7.5 (8.6) | −3.1 (6.5) | 0.057 |
| Day 270 | −10.0 (6.1) | −7.3 (6.1) | 0.080 | −7.6 (9.1) | −3.3 (7.7) | 0.139 |

[a] Between treatment comparison from a Wilcoxon rank-sum test.

Frequency of Headaches by Baseline Analgesic Acute Headache Medication Overuse

Medication overuse was defined as use of any acute analgesic medication for 15 days and 2 days/week. Based on this definition, for patients who did not have overuse of acute analgesic medications at baseline there were no statistically significant differences between BOTOX® and placebo in the changes from baseline in the frequency of headaches per 30-day period at any time point (Table 16). For patients with overuse of acute analgesic medications at baseline, except for Day 90, the difference in the decrease from baseline were significantly greater for BOTOX® than placebo. The mean decreases from baseline were greater for BOTOX® by 2.0 to 5.6 headaches at all time points, except at Day 90 (Table 16).

TABLE 16

Mean (Standard Deviation) at Baseline and Change from Baseline in the
Frequency of Headaches per 30-Day Period for
Patients with Acute Analgesic Headache
Medication Overuse (No, Yes) at Baseline; Pooled Population

| | Any Analgesic Overuse for ≥15 Days and ≥2 Days/Week, No | | | Any Analgesic Overuse for ≥15 Days and ≥2 Days/Week, Yes | | |
|---|---|---|---|---|---|---|
| Time Period | BOTOX® N = 82 | Placebo N = 105 | p-value[a] | BOTOX® N = 91 | Placebo N = 77 | p-value[a] |
| Baseline | 11.7 (6.7) | 11.1 (7.5) | 0.477 | 15.2 (8.2) | 14.9 (8.9) | 0.592 |
| Treatment 1: Placebo (followed by a 30-day run-in period) | | | | | | |
| Treatment 2 | | | | | | |
| Day 30 | −3.5 (4.8) | −2.8 (5.0) | 0.320 | −4.5 (6.1) | −2.5 (4.9) | 0.020 |
| Day 60 | −4.0 (5.3) | −3.7 (5.4) | 0.756 | −5.6 (5.9) | −2.6 (5.2) | 0.001 |
| Day 90 | −4.5 (5.5) | −3.7 (5.8) | 0.726 | −5.2 (6.4) | −3.7 (5.6) | 0.168 |
| Treatment 3 | | | | | | |
| Day 120 | −4.6 (3.9) | −3.6 (6.3) | 0.342 | −6.2 (6.4) | −3.6 (5.2) | 0.044 |
| Day 150 | −5.6 (4.7) | −4.9 (5.7) | 0.585 | −8.2 (6.6) | −4.3 (6.3) | 0.018 |
| Day 180 | −6.1 (4.7) | −3.8 (6.0) | 0.088 | −8.1 (6.3) | −3.6 (6.4) | 0.003 |
| Treatment 4 | | | | | | |
| Day 210 | −5.5 (5.6) | −4.4 (7.1) | 0.495 | −9.3 (7.3) | −3.9 (6.2) | 0.003 |
| Day 240 | −5.7 (4.9) | −5.5 (6.6) | 0.885 | −10.1 (8.1) | −4.5 (6.1) | 0.007 |
| Day 270 | −6.3 (4.9) | −5.8 (7.5) | 0.800 | −9.5 (8.0) | −4.9 (6.4) | 0.017 |

[a] Between treatment comparison from a Wilcoxon rank-sum test.

Type of Headaches

Each headache was classified as migraine (ICHD 1) or non-migraine (ICHD 2; e.g., tension-type headache). All patients experienced at least 1 migraine during the baseline period, suggesting that all patients may actually have a diagnosis of migraine even though this diagnosis was not recognized by the investigator for all patients. During the study, patients experienced both migraine and non-migraine headaches. The majority of headaches in both treatment groups were classified as migraine (per the ICHD criteria).

Migraine

The mean baseline and mean changes from baseline in the frequency of migraine (ICHD 1.1 or 1.2) or probable migraine (ICHD 1.5.1) headaches per 30-day period are shown in Table 17. At all time points the decreases from baseline were greater for BOTOX® compared with placebo and were significantly greater (p<0.048) at Days 120, 180, and 210. At these time points the mean decreases from baseline were greater for BOTOX® by 1.6 to 2.8 headaches.

TABLE 17

Mean (Standard Deviation) at Baseline and Change from Baseline in the Frequency of Migraine and Probable Migraine Headaches per 30-Day Period; Pooled Population

| Time Period | BOTOX® N = 173 | Placebo N = 182 | p-value [a] |
|---|---|---|---|
| Baseline | 11.2 (6.6) | 10.8 (7.9) | 0.274 |
| Treatment 1: Placebo (followed by a 30-day run-in period) | | | |
| Treatment 2 | | | |
| Day 30 | −3.2 (4.9) | −2.7 (4.4) | 0.335 |
| Day 60 | −3.9 (5.2) | −3.1 (5.0) | 0.134 |
| Day 90 | −3.9 (5.6) | −3.5 (5.3) | 0.768 |
| Treatment 3 | | | |
| Day 120 | −4.7 (5.0) | −3.1 (5.5) | 0.048 |
| Day 150 | −5.7 (5.2) | −3.7 (6.0) | 0.057 |
| Day 180 | −5.8 (5.4) | −3.0 (5.7) | 0.002 |
| Treatment 4 | | | |
| Day 210 | −5.9 (5.9) | −3.3 (6.3) | 0.018 |
| Day 240 | −6.0 (5.6) | −4.2 (5.7) | 0.083 |
| Day 270 | −6.4 (5.8) | −4.3 (6.5) | 0.067 |

[a] Between treatment comparison from a Wilcoxon rank-sum test.

Non-Migraine Headaches

The mean frequency of non-migraine headaches per 30-day period at baseline was 2.3 and 1.8 in the BOTOX® and placebo groups, respectively. There were no statistically significantly differences (p 0.065) between BOTOX® and placebo in the changes from baseline in the frequency of non-migraine headaches per 30-day period at all time points except at Day 90 (p=0.034). At all time points after the run-in period, the mean decreases from baseline were greater for BOTOX® by 0.3 to 1.0 non-migraine headaches. At Day 90 the mean decrease was 1.0 for BOTOX® and 0.2 for placebo.

MOU

There were few statistically significant differences between treatment groups in the use of any acute headache medication (e.g. triptans, opioids, etc) during any 30-day treatment period. There were also no statistically significant between-group differences for the individual categories of medication, i.e., ergotamines, triptans, simple analgesics, or anti-emetics. There were significant differences between treatment groups for opioids at Day 210 (11.4% [8/70], BOTOX®, 24.7% [19/77] placebo; p=0.038 and for combination therapies at Day 210 (34.3% [24/70] BOTOX®, 18.2% [14/77] placebo; p=0.026) and Day 240 (32.9% [23/70] BOTOX®, 18.3% [13/71] placebo; p=0.048.

The baseline characteristics of patients overusing and not overusing acute analgesic headache medication at baseline at summarized in Table 18. Patients overusing acute analgesic headache medications were significantly older at baseline (mean age, 45.6 versus 41.6 years; p=0.001), otherwise there were no statistically significant differences between the demographic characteristics of overusers and non-overusers of acute analgesic headache medications at baseline.

TABLE 18

Baseline Characteristics of Patients With and Without Analgesic Headache Medication Overuse at Baseline; Pooled Population

| Baseline Characteristic | Analgesic Headache Medication Overuse [a] at Baseline | | P-Value |
|---|---|---|---|
| | Yes N = 168 | No 187 | |
| Age, mean years (SD) | 45.6 (9.6) | 41.6 (11.0) | 0.001 [b] |
| Sex, n (%) | 32 (19.0) | 23 (12.3) | 0.079 [c] |
| Male | 136 (81.0) | 164 (87.7) | |
| Female | | | |
| Race, n (%) | 151 (89.9) | 161 (86.1) | 0.275 [c] |
| Caucasian | 17 (10.1) | 26 (13.9) | |
| Non-Caucasian | | | |
| Years since onset, mean (SD) | 15.7 (12.6) | 13.5 (12.2) | 0.075 [b] |
| Age at onset, mean years (SD) | 29.3 (12.4) | 27.5 (13.4) | 0.153 [b] |
| Prophylactic headache medications, n (%) | 61 (36.3) | 66 (35.3) | 0.842 [c] |
| Beta blockers | 16 (9.5) | 21 (11.2) | 0.599 [c] |
| Calcium channel blockers | 14 (8.3) | 13 (7.0) | 0.624 [c] |
| Anticonvulsants | 23 (13.7) | 27 (14.4) | 0.840 [c] |
| Antidepressants | 38 (22.6) | 36 (19.3) | 0.435 [c] |
| Baseline MIDAS score, mean (SD) | 54.3 (54.7) | 60.6 (55.2) | 0.144 [b] |
| Baseline Beck Depression Inventory score, mean (SD) | 7.9 (6.6) | 7.8 (7.1) | 0.577 [b] |

SD = standard deviation.
[a] Overuse = use for ≥15 days and ≥2 days/week
[b] P-values for treatment comparisons from the Wilcoxon rank-sum test.
[c] P-values for treatment comparisons from Pearson's chi-square or Fisher's exact tests.

At all post-baseline time points, in the BOTOX® compared with the placebo group there was a greater decrease in the number of uses of acute analgesic headache medications, with a statistically significant difference at Days 90 and 210 (p≤0.047). This also was observed in the analysis of the mean number of days acute analgesic headache medications were used, with statistically significant differences at Days 90, 180, 210, and 240 (p≤0.033).

TABLE 19

Mean (Standard Deviation) at Baseline and Change from Baseline in the Number of Uses and Days of Use of Acute Analgesic Headache Medications per 30-Day Period for Patients Not Using Prophylactic Headache Medications at Baseline; Pooled Population

| Time Period | Number of Uses of Analgesic Acute Headache Medications | | | Days with Analgesic Acute Headache Medication Use | | |
|---|---|---|---|---|---|---|
| | BOTOX® N = 117 | Placebo N = 111 | p-value [a] | BOTOX® N = 117 | Placebo N = 111 | p-value [a] |
| Baseline | 25.1 (17.7) | 21.0 (15.9) | 0.058 | 15.5 (8.4) | 13.5 (8.3) | 0.069 |
| Treatment 1: Placebo (followed by a 30-day run-in period) | | | | | | |
| Treatment 2 | | | | | | |
| Day 30 | −8.7 (13.3) | −5.7 (10.2) | 0.096 | −4.5 (6.3) | −3.3 (5.9) | 0.206 |
| Day 60 | −10.3 (14.8) | −6.4 (10.1) | 0.076 | −5.5 (7.0) | −3.6 (6.6) | 0.052 |
| Day 90 | −10.3 (14.2) | −6.2 (9.9) | 0.047 | −5.7 (6.7) | −3.3 (6.8) | 0.025 |
| Treatment 3 | | | | | | |
| Day 120 | −10.0 (16.7) | −7.7 (9.0) | >0.999 | −5.7 (6.9) | −4.1 (5.9) | 0.427 |

TABLE 19-continued

Mean (Standard Deviation) at Baseline and Change from Baseline in the Number of Uses and Days of Use of Acute Analgesic Headache Medications per 30-Day Period for Patients Not Using Prophylactic Headache Medications at Baseline; Pooled Population

| Time Period | Number of Uses of Analgesic Acute Headache Medications | | | Days with Analgesic Acute Headache Medication Use | | |
|---|---|---|---|---|---|---|
| | BOTOX® N = 117 | Placebo N = 111 | p-value[a] | BOTOX® N = 117 | Placebo N = 111 | p-value[a] |
| Day 150 | −13.2 (16.5) | −8.7 (10.6) | 0.199 | −7.9 (6.8) | −5.2 (6.7) | 0.098 |
| Day 180 | −12.9 (15.5) | −7.9 (11.4) | 0.110 | −7.8 (6.3) | −4.1 (6.6) | 0.015 |
| Treatment 4 | | | | | | |
| Day 210 | −14.6 (17.3) | −7.4 (11.3) | 0.018 | −8.5 (7.6) | −4.0 (7.4) | 0.011 |
| Day 240 | −15.8 (18.1) | −8.5 (9.5) | 0.151 | −9.3 (8.1) | −4.7 (7.0) | 0.033 |
| Day 270 | −15.6) (15.9 | −9.2 (11.3) | 0.093 | −8.8 (7.6) | −5.2 (7.3) | 0.086 |

[a] Between treatment comparison from a Wilcoxon rank-sum test.

Overall, 97.7% (347/355) of patients received acute headache medications while in the study, with similar proportions in each treatment group: 98.3% (170/173) of patients in the BOTOX® group and 97.3% (177/182) in the placebo group.

Overall, 87.6% (311/355) of patients received concomitant medications (other than acute headache medications), with similar proportions in each treatment group: 90.2% (156/173) of patients in the BOTOX® group and 85.2% (155/182) in the placebo group.

A total of 35.8% (127/355) of patients were taking a headache prophylaxis medication during baseline. These included 10.4% (37/355) on beta blockers, 7.6% (27/355 on calcium channel blockers, 14.1% (50/355) on anti-convulsants, and 20.8% (74/355) on anti-depressants. There were no statistically significant differences between the BOTOX progestogens and placebo groups in the number of patients using any of the aforementioned headache prophylactic medications.

During the placebo run-in period (first treatment cycle 1, Day −30 to Day 0) all patients received placebo on Day −30. On Day 0, patients were randomized to receive 3 treatment cycles of intramuscular injections of BOTOX® or placebo. Of the 355 patients enrolled in the study, 173 received 105 U to 260 U BOTOX® and 182 received placebo. The maximum dose of BOTOX® that patients could have received according to the protocol was 260 U per treatment cycle for each of 3 treatment cycles for a total cumulative exposure of 780 U.

Dose

The mean (median) total dose of BOTOX® for the second, third, and fourth treatment cycles was 190.8 U (200 U), 190.9 U (200 U), and 190.5 U (200 U), respectively. The mean and median doses of BOTOX® injected into each muscle group for the second, third, and fourth treatment cycles are presented in Table 20. Of note is the observation that the optional injection of the masseter was administered to less than half of the patients in both the BOTOX® and placebo groups.

TABLE 20

Mean (Median) Dose of BOTOX® Injected into Each Muscle Group per Treatment

| Muscle Injected (Allowable Dose Range) | Treatment Cycle 2 (Day 0) | Treatment Cycle 3 (Day 90) | Treatment Cycle 4 (Day 180) |
|---|---|---|---|
| Frontal/glabellar (25 to 40 U) | 38.0 U (40 U) | 37.3 U (40 U) | 37.1 U (40 U) |
| Occipitalis (20 U) | 19.8 U (20 U) | 19.8 U (20 U) | 19.7 U (20 U) |
| Temporalis (20 to 50 U) | 42.0 U (40 U) | 42.7 U (45 U) | 43.7 U (45 U) |
| Masseter (optional; 0 to 50 U) | 8.0 U (0 U) | 7.6 U (0 U) | 6.5 U (0 U) |
| Trapezius (20 to 60 U) | 47.4 U (60 U) | 48.3 U (60 U) | 48.4 U (60 U) |
| Semispinalis (10 to 20 U) | 18.2 U (20 U) | 18.0 U (20 U) | 17.9 U (20 U) |
| Splenius capitis (10 to 20 U) | 18.6 U (20 U) | 18.1 U (20 U) | 18.1 U (20 U) |

Note:
During treatment cycle 1 all patients were treated with placebo.

The mean (median) number of sites injected with BOTOX® per muscle group for the first, second, and third injections are presented in Table 21.

TABLE 21

Mean (Median) Number of Sites BOTOX® Injected per Muscle Group per Treatment Cycle

| Muscle Injected (Allowable Dose Range) | Treatment Cycle 2 (Day 0) | Treatment Cycle 3 (Day 90) | Treatment Cycle 4 (Day 180) |
|---|---|---|---|
| Frontal/glabellar (25 to 40 U) | 9.5 (9.0) | 9.8 (10.0) | 9.7 (10.0) |
| Occipitalis (20 U) | 3.0 (2.0) | 2.8 (2.0) | 2.9 (2.0) |
| Temporalis (20 to 50 U) | 6.5 (6.0) | 6.3 (6.0) | 6.4 (6.0) |
| Masseter (optional; 0 to 50 U) | 1.3 (0.0) | 1.2 (0.0) | 1.2 (0.0) |
| Trapezius (20 to 60 U) | 5.9 (6.0) | 6.0 (6.0) | 6.0 (6.0) |
| Semispinalis (10 to 20 U) | 3.0 (2.0) | 2.9 (2.0) | 2.9 (2.0) |
| Splenius capitis (10 to 20 U) | 3.1 (2.0) | 2.9 (2.0) | 3.0 (2.0) |

Note:
During treatment cycle 1 all patients were treated with placebo.

Significant and consistent efficacy favoring BOTOX® over placebo was observed for the change from baseline in the frequency of headaches per 30-day period. These changes were observed in the placebo non-responder and the placebo responder strata, the pooled data, and in the subgroup of patients with no baseline headache prophylactic treatment. Change in the frequency of headache is a preferred primary endpoint in migraine trials (European Agency for the Evaluation of Medicinal Products, 2003). Recent US FDA approved prophylactic treatment for migraine headache also established efficacy by measuring a change in frequency of headaches (Depakote package insert, 2003).

Significant differences were found between the groups favoring BOTOX® in the percentage of patients with a decrease from baseline of at least 50% or more per 30-day period in the number of headaches at Day 180 (54.2% vs. 38.0%, p=0.046) and Day 210 (57.1% vs. 36.4%, p=0.012). In addition, the percentage of patients with a 50% decrease in headaches per 30-day period occurred in more than 50% of patients at Days 150, 180, 210, 240, and 270 in the BOTOX® group, while this level was reached only at Day 270 in the placebo group.

Example 4—Botulinum Toxin Type A Injection Paradigm for Treating Chronic Migraine A clinical study was carried out to develop and optimize a dosing and injection paradigm for administration of botulinum toxin, useful in treating migraine, particularly chronic migraine. This study developed a new method and selection of muscles to be injected; minimal, as well as optional maximal, dose and numbers of injection sites per muscle were specified in this study. In this study we used a preferred botulinum toxin formulation (BOTOX®). The injection paradigm herein is particularly useful for treating migraine patients with 15 or more headache days during a 28 day period. In one aspect (double blind phase) the study compared botulinum toxin administration, according to this injection and dosing paradigm, with placebo, as a headache prophylaxis treatment for migraine patients with 15 or more headache days per 4-week period.

We discovered that injection, in a preferred embodiment, of a minimum 31 to maximum 39 injection sites, minimum dose of 155 up to 195 unit maximum administration of botulinum toxin type A (here BOTOX®) injection paradigm detailed below, provided very positive and effective clinical outcomes for patients treated.

In one embodiment of a dosage paradigm utilized in Example 3, administration of 155 units to 195 units (at 31 to 39 injection sites) per treatment cycle was repeated every 12 weeks, up to a maximum of 5 injection cycles. This injection paradigm, in one embodiment, required a minimum dose of 155 U using a fixed-site, fixed-dose injection regimen into 31 sites across 7 head/neck muscles. An optional additional dose of botulinum toxin of up to 40 U (to up to 8 sites), using a follow-the-pain regimen, provided flexibility in the dosage per muscle for 3 muscles (temporalis, occipitalis and trapezius) to address individual patient needs. In utilizing the optional, additional follow-the-pain regimen portion of this new injection paradigm for these 3 muscles (temporalis, occipitalis and trapezius), the optional and additional botulinum toxin was administered either unilaterally or bilaterally to one or up to three of the specific head/neck muscle areas (temporalis and/or occipitalis and/or trapezius).

Turning to FIG. 17, an example of fixed locations to which doses of botulinum toxin was administered to patients (here administered in supine and sitting positions, for example) in accordance with one aspect of an injection paradigm, are depicted. In FIG. 17, at each site indicated, 0.1 mL=5U of Botulinum Toxin Type A was administered. Abbreviations utilized in FIG. 17 (under each of the muscles named), mean FSFD=Fixed site, fixed dose; FTP=optional follow-the-pain (locations and amounts of botulinum toxin administered, if utilizing the optional follow-the-pain portion of the injection paradigm, are detailed below).

We have determined that the frontal/glabellar region was the most frequent location where head pain started and ended. We determined that to ensure efficacy, consistency and standardization of treatment, three muscles (frontalis, corrugators and procerus) were selected to be included as part of the 31 fixed site and fixed dosage muscles of the injection paradigm of Example 2. In order to reduce the potential for focal adverse events such as eyelid ptosis, a total dose of 35 U was determined to be most advantageous. Furthermore, the exact number and locations for injection to these muscles were specified to ensure optimal tolerability and to specifically minimize eyelid ptosis. Indeed, the specified injection method in these muscles achieved these goals since statistically significant separation from placebo across multiple headache symptom measures with an overall eyelid ptosis rate for BOTOX® treated patients in the double-blind, placebo controlled phase was found.

In injecting these shallow muscles, the needle was preferably kept superficial to avoid hitting the periosteum. In one aspect, a total of 2 injections was given to the corrugator muscle, one on each side of the forehead (FIG. 17, A). The injection site is located approximately 1.5 cm (1 finger breadth) above the medial superior edge of the orbital ridge (bony landmark). The thumb was placed under the corrugator muscle and the injection is done with the needle angled up and away from the eye (towards the forehead), to prevent ptosis of the eyelid. In another aspect, the procerus muscle can have 1 injection site, which is midline on the forehead approximately 1.5 cm above and midline to the medial superior aspect of the orbital ridge (bony landmark) of each eye (FIG. 17, B). This injection site is substantially midway between the 2 corrugator injections. In injecting the frontalis, the needle did not need to be directed upward for these injections. A total of 4 injections (2 on the left side and 2 on the right) were given to the frontalis. For the 2 medial injection sites, an imaginary line up from the medial edge of the eyebrow at about 1.5 cm (a finger breadth) from the corrugator injection site is a helpful method for determining needle placement (FIG. 17, C). The lateral injection sites were parallel and approximately 1.5 cm lateral of the medial injections sites.

Turning to the temporalis, we determined that the temporalis area was the second most frequent location where head pain started and ended. A fixed-site, fixed-dose regimen for this muscle was utilized in the present injection paradigm. Because this muscle is a very common location of predominant pain for many patients, a minimum dose of 20 units per side (minimum 40 units total) was determined, and up to an additional 10 units total (administered to 1 or both sides in 5 unit increments) to this muscle group was allowed using a follow-the-pain strategy.

The temporal area received a minimum total of 8 injections, 4 to each side (FIG. 17, D). In addition, up to 2 additional injections using the optional follow-the-pain paradigm was used. Prior to any injection, the muscles on both sides of the head were palpated for tenderness or pain. Patient clenching of teeth assisted the physician in locating the anterior aspect of the temporalis muscle, which was then palpated. The first injection was made just behind this point, trying to stay behind the hairline. The second injection was approximately 0.5 cm superior and 1.5 cm posterior to the first injection in the medial aspect of the muscle. The third injection site was parallel and approximately 1.5 cm posterior to the second injection. The fourth fixed-site injection was 1.5 cm below and perpendicular to the second injection, into the medial aspect of the muscle. If additional injections (utilizing the follow-the-pain aspect of this Example 2 injection paradigm) of botulinum toxin were used, additional sites of injection (rather than increasing the injection volume to the fixed 4 sites) were performed.

Turning to the cervical paraspinal muscle group (neck muscles), we determined that headache pain frequently started and/or stopped in the back of the head (either in the occipitalis and/or the neck). Thus it was determined that for the injection paradigm utilized in this Example, injections were given to the upper neck (cervical paraspinal muscles above the occipital ridge) at the base of the skull, rather than to the mid-neck region (to avoid neck pain and neck rigidity), and thus a follow-the-pain injection regimen was not allowed in the neck region, and injections were more superficial rather than inserted deeply into the neck muscles (in one preferred embodiment, the injection needle length and gauge were standardized to 0.5 inch and 30 gauge, respectively) and the total dose injected to the neck region was reduced. Thus the overall dose to the cervical paraspinal muscle group was a fixed-site, fixed-dose of 20 U total for this muscle group (10U to each side of the head divided among 4 sites (5 U per site, FIG. 17, F)). We determined that this dose is sufficient from an efficacy perspective and this particular neck dose results in less or no neck pain, less or no neck rigidity and decreased the risk of excessive neck muscle weakness, which improved the overall tolerability profile while maintaining efficacy. Beginning on the left side, the cervical paraspinal muscle group injection sites were located by palpating the cervical spine and it was preferable to not to go too deep into the cervical paraspinal and trapezius muscles with the injections (hub of the 0.5 inch needle serves as a relatively accurate "depth" guide). The first injection was administered lateral to the midline, approximately 3-5 centimeters inferior to the occipital protuberance. A second injection was administered on the same side, 1 cm lateral and superior to the first injection (diagonally toward the ear from the first injection). This procedure was repeated symmetrically on the contralateral side, for a total of 4 injections (fixed sites).

Relating to the trapezius, we determined that headache pain frequently started and/or ended in the trapezius muscles. Thus, the dosage regimen for the trapezius muscle was standardized to a minimum dose of 30 U (15U on each side) (to avoid/minimize arm (shoulder) pain), with the option for additional follow-the-pain treatment to a maximum dose of 50 U (i.e. an additional 20 units and up to 10 sites overall), if clinically needed.

Accordingly, the superior portions of the trapezius muscles were palpated to identify areas of tenderness and/or pain. Beginning on the left side, the muscle was visually divided into 3 sections. In one embodiment, the first injection to the trapezius was administered in the lateral aspect of the muscle. Moving medially, the mid-portion of the trapezius was administered the second injection, while the third injection was administered medially and superiorly within the third section of the muscle. This procedure was repeated symmetrically on the contralateral side for a total of 6 injections (FIG. 17, G). According to one aspect of the follow-the-pain optional dosing paradigm, an additional 4 injections were, if needed, distributed between the right and left trapezius muscles in the areas identified as having maximal tenderness. The infero-medial portions of the trapezius muscle were avoided to limit the possibility of neck weakness.

Relating to the occipitalis, we determined that the occipitalis was a third most frequent location where headache pain started and ended. In accordance with one aspect of our new injection and dosage paradigm, the minimum dose administered to the occipitalis was 30U at 6 sites for injection into the occipitalis, located primarily above the occipital ridge, which reduced the risk of neck weakness. We also determined that in order to address possible complaints of a predominant pain in the back of the head, additional follow-the-pain dosing was allowed in the occipitalis.

Prior to injecting the occipital area, both the left and right sides were palpated to identify the areas of tenderness and/or pain. To locate the occipitalis injection sites, the external occipital protuberance was palpated. The sites are superior to the supranuchal ridge on either side of this protuberance. In one embedment, three injections were administered to the right and left occipitalis muscles, for a total of 6 injections (FIG. 17, E). As an example, the first injection was given just above the occipital protuberance along the supranuchal ridge and approximately 1 cm left/right (depending on the side) of the external occipital protuberance. The second injection was given approximately 1 cm to the left/right and approximately 1 cm above the first injection. The third injection was given 1 cm medial and 1 cm above the first injection site. According to and in one aspect of an embodiment, the follow-the-pain optional dosing paradigm, an additional 2 injections were, if needed, distributed between the right and left occipitalis muscles (1 injection on each side or 2 injections on 1 side) in the areas that were identified as having maximal tenderness.

In an embodiment of our invention, the masseter muscle was not included as a target muscle group for injection in the instant injection/dosage paradigm utilized. We surprisingly determined that even though some patients had pain in the masseter region as part of their chronic migraine symptoms, injection of botulinum toxin to the masseter muscles was not necessary in order to obtain positive clinical outcomes for the headache patients.

Thus, this paradigm, which utilizes a combination of fixed and follow-the-pain sites for administration of botulinum toxin, provides optimal distribution of botulinum toxin, such as a botulinum toxin type A, based on individual patient symptoms.

Thus, in one embodiment a fixed minimum dose of 155 U and fixed number of injection sites (31 sites) divided across 7 specific head and neck muscles (referred to as a fixed-site, fixed-dose regimen) (Table 23) were tested. Interestingly, this protocol also allowed for a modified and outlined follow-the-pain regimen of up to an additional 40U divided across 3 specific muscles: temporalis (up to an additional 10U total in up to an additional 2 sites), occipitalis (up to an additional 10U total in up to an additional 2 sites) and trapezius (up to an additional 20U total in up to an additional 4 sites) (Table 24). As indicated below, the follow-the-pain portion regimen was not required, nor was there a requirement to standardize the use of follow-the-pain from one injection cycle to another injection cycle (toxin administered every 12 weeks).

The overall study was a multicenter, double-blind, randomized, placebo-controlled, parallel-group clinical study with an open-label extension phase, and was conducted for 60 weeks (including a 4-week baseline phase, followed by a 24-week, double-blind treatment phase prior to patients entering a 32-week, open-label extension phase. Patients were randomized/stratified following a 4 week baseline phase, whereby patients meeting the inclusion/exclusion criteria were assigned a randomization number provided via a central telephone randomization system. Patients were classified as medication overusers ("yes") if they meet 1 or more of these categories.

TABLE 22

Overuse Criteria

| Drug | Criteria for Overuse |
| --- | --- |
| Overall: combined across at least two categories among ergotamines, triptans, analgesics (including simple | >10 days per month and at least 2 days per week |

TABLE 22-continued

Overuse Criteria

| Drug | Criteria for Overuse |
| --- | --- |
| analgesics and combination analgesics as one category) and opioids. | |
| Ergotamine | ≥10 days per month and at least 2 days per week |
| Triptan | ≥10 days per month and at least 2 days per week |
| Simple Analgesic | ≥15 days per month and at least 2 days per week |
| Opioid | ≥10 days per month and at least 2 days per week |
| Combination analgesic medication | ≥10 days per month and at least 2 days per week |

Within each stratum, the patient was randomly allocated to receive either botulinum toxin or placebo in a 1:1 ratio. As to the dosage and dose regimen, two (2) treatment sessions in the double-blind phase and three (3) treatment sessions in the open-label extension were conducted. In the double-blind phase, all patients received a minimum dose of 155 U botulinum toxin or placebo administered as 31 fixed-site, fixed-dose injections across seven (7) specific head/neck muscle areas listed in Table 23. In addition, at the medical practitioner's discretion, additional injections of botulinum toxin or placebo were administered unilaterally or bilaterally, using a follow-the-pain paradigm in up to three (3) specific head/neck muscle areas (temporalis, occipitalis, and/or trapezius). According to one embodiment, dosing and number of possible injection sites are described below in table form:

TABLE 23

Required Dose Using a Fixed-Site, Fixed-Dose Injection

| Head/Neck Area | LEFT Number of units per muscle (number of injection sites[a]) | RIGHT Number of units per muscle (number of injection sites) | TOTAL Number of units per muscle (number of injection sites) |
| --- | --- | --- | --- |
| Frontalis | 10 (2 sites) | 10 (2 sites) | 20 (4 sites) |
| Corrugator | 5 (1 site) | 5 (1 site) | 10 (2 sites) |
| Procerus | — | — | 5 (1 site) |
| Occipitalis | 15 (3 sites) | 15 (3 sites) | 30 (6 sites) |
| Temporalis | 20 (4 sites) | 20 (4 sites) | 40 (8 sites) |
| Trapezius | 15 (3 sites) | 15 (3 sites) | 30 (6 sites) |
| Cervical Paraspinal Muscle Group | 10 (2 sites) | 10 (2 sites) | 20 (4 sites) |
| Minimum Total | — | — | 155 U (31 sites) |

[a]1 injection site = 0.1 mL = 5 U of Botulinum Toxin Type A or 0 U of placebo group Optional additional injections (i.e. in addition to those detailed in Table 23) were not needed to be consistent across treatment visits, with respect to dose or number of injection sites (as they were administered on a case-by-case basis and at the medical practitioner's discretion, but did not exceed the maximum dose allowed (i.e. 195 units)). We determined that the medical practitioner takes into account patient-reported usual location of predominant pain, severity of the muscle tenderness while palpating the muscle prior to injection, and the medical practitioner's best judgment on the potential benefit of additional doses in the specified muscles (e.g. large muscle size) in determining how many additional units to inject above the fixed minimum amount for a particular muscle region (e.g. temporalis and/or occipitalis and/or trapezius). Thus, in one example, the total minimum dose was 155 U with 31 head/neck injections, and the total maximum dose was 195 U with 39 head/neck injections.

TABLE 24

Optional additional dosing using a follow-the-pain injection paradigm:

| Head/Neck Area | LEFT Number of units per muscle (number of injection sites) | RIGHT Number of units per muscle (number of injection sites[a]) | Location of usual pain or tenderness on palpation | TOTAL Number of units per muscle (number of injection sites) |
| --- | --- | --- | --- | --- |
| Occipitalis[b] | 5 U/site (up to 2 sites) | 0 | left side | 0, 5 or 10 U (0, 1 or 2 sites) |
| | 0 | 5 U/site (up to 2 sites) | right side | |
| | 5 U (1 site) | 5 U (1 site) | both sides | |
| Temporalis[b] | 5 U/site (up to 2 sites) | 0 | left side | 0, 5 or 10 U (0, 1 or 2 sites) |
| | 0 | 5 U/site (up to 2 sites) | right side | |
| | 5 U (1 site) | 5 U (1 site) | both sides | |
| Trapezius[b] | 5 U/site (up to 4 sites) | 0 | left side | 0, 5, 10, 15 or 20 U (0, 1, 2, 3 or 4 sites) |
| | 5 U/site (up to 3 sites) | 5 U (1 site) | | |
| | 0 | 5 U/site (up to 4 sites) | right side | |
| | 5 U (1 site) | 5 U/site (up to 3 sites) | | |
| | 5 U/site (up to 2 sites) | 5 U/site (up to 2 sites) | both sides | |
| Max. additional | | | | 40 U (8 sites) |
| Max. Total | | | | 195 U (39 sites) |

[a]1 injection site = 0.1 mL = 5 U of Botulinum Toxin Type A or 0 U of placebo group
[b]Maximum additional dose distributed unilaterally or bilaterally is as follows: Occipitalis = U, Temporalis = 10 U, Trapezius = 20 U During the baseline phase of this example (Week −4 to Day 0) the patient had at least 15 headache days and at least 4 headache episodes of any type each with a minimum duration of 4 hours. At least 50% of these headache episodes were classified as migraine (ICHD-II 1.1 or 1.2), or probable migraine (ICHD-II 1.6). After the 4-week baseline phase, prospective patients returned to the investigators office to qualify for entry into the 24-week double-blind treatment phase. Women of childbearing potential had a negative urine pregnancy test prior to entry into the 4-week baseline phase and also prior to the first injection of study medication at Day 0.

Accordingly and as one example, a combined fixed site and follow-the pain paradigm of botulinum toxin dosing and administration sites, having a minimum number of head, neck, shoulder areas to be administered a minimum amount of botulinum toxin, along with a subset of those head, neck, shoulder areas to which additional botulinum toxin can be administered (up to a stated maximum dosage, such as a maximum dosage enumerated in a package insert or pre-scribing information is disclosed.

The invention claimed is:

1. A method for the prophylaxis of headache in a patient with migraine, the method comprising:
   administering to the patient by intramuscular injection a composition comprising about 155 units of a botulinum neurotoxin type A (BoNT/A) complex to a total of 31 injection sites across seven head and neck muscles, thereby reducing the frequency of occurrence of headache in the patient;
   wherein the composition comprising about 155 units of BoNT/A complex is divided across the 31 injection sites as follows:
   a) about 20 total units of the BoNT/A complex is injected at 4 total injection sites in the patient's frontalis muscle, the 4 total injection sites comprising 2 injection sites in the left side of the patient's frontalis muscle and 2 injection sites in the right side of the patient's frontalis muscle;
   b) about 10 total units of the BoNT/A complex is injected at 2 total injection sites in the patient's corrugator muscles, the 2 total injection sites comprising 1 injection site in the patient's left corrugator muscle and 1 injection site in the patient's right corrugator muscle;
   c) about 5 total units of the BoNT/A complex is injected at 1 injection site in the patient's procerus muscle at the midline;
   d) about 30 total units of the BoNT/A complex is injected at 6 total injection sites in the patient's occipitalis muscles, the 6 total injection sites comprising 3 injection sites in the patient's left occipitalis muscle and 3 injection sites in the patient's right occipitalis muscle;
   e) about 40 total units of the BoNT/A complex is injected at 8 total injection sites in the patient's temporalis muscles, the 8 total injection sites comprising 4 injection sites in the patient's left temporalis muscle and 4 injection sites in the patient's right temporalis muscle;
   f) about 30 total units of the BoNT/A complex is injected at 6 total injection sites in the patient's trapezius muscles, the 6 total injection sites comprising 3 injection sites in the patient's left trapezius muscle and 3 injection sites in the patient's right trapezius muscle; and
   g) about 20 total units of the BoNT/A complex is injected at 4 total injection sites in the patient's cervical paraspinal muscles, the 4 total injection sites comprising 2 injection sites in the patient's left cervical paraspinal muscle and 2 injection sites in the patient's right cervical paraspinal cervical muscle; and
   wherein about 5 units of the BoNT/A complex is injected at each of the 31 injection sites.

2. The method of claim 1, wherein the BoNT/A complex is a 900 kD complex.

3. The method of claim 1, wherein the patient suffers from chronic migraine.

4. The method of claim 1, wherein the patient suffers from episodic migraine.

5. The method of claim 1, wherein the BoNT/A complex is onabotulinumtoxinA.

6. The method of claim 1, wherein the concentration of the BoNT/A complex in the composition is about 5 units per 0.1 mL.

7. The method of claim 1, wherein the composition comprises a powdered BoNT/A pharmaceutical composition that has been reconstituted with normal saline, wherein prior to the reconstitution, the powdered BoNT/A pharmaceutical composition consists of the BoNT/A complex, human albumin, and sodium chloride.

8. The method of claim 1, wherein the injections are not made deeper than about 0.5 inches into a muscle.

9. The method of claim 1, wherein the composition is administered to the patient using a sterile 30-gauge syringe with a 0.5 inch needle.

10. The method of claim 1, wherein the composition is administered to the patient using a sterile 30-gauge syringe with a 1 inch needle.

11. The method of claim 1, wherein the method is repeated every 12 weeks.

12. A method for the prophylaxis of headache in a patient with chronic migraine, the method comprising:
    administering to the patient by intramuscular injection a composition comprising about 155 units of a BoNT/A complex to a total of 31 injection sites across seven head and neck muscles, thereby reducing the frequency of occurrence of headache in the patient; wherein the concentration of the BoNT/A complex in the composition is about 5 units per 0.1 mL; and wherein the composition comprising about 155 units of BoNT/A complex is divided across the 31 injection sites as follows:
    a) about 20 total units of the BoNT/A complex is injected at 4 total injection sites in the patient's frontalis muscle, the 4 total injection sites comprising 2 injection sites in the left side of the patient's frontalis muscle and 2 injection sites in the right side of the patient's frontalis muscle;
    b) about 10 total units of the BoNT/A complex is injected at 2 total injection sites in the patient's corrugator muscles, the 2 total injection sites comprising 1 injection site in the patient's left corrugator muscle and 1 injection site in the patient's right corrugator muscle;
    c) about 5 total units of the BoNT/A complex is injected at 1 injection site in the patient's procerus muscle at the midline;
    d) about 30 total units of the BoNT/A complex is injected at 6 total injection sites in the patient's occipitalis muscles, the 6 total injection sites comprising 3 injection sites in the patient's left occipitalis muscle and 3 injection sites in the patient's right occipitalis muscle;
    e) about 40 total units of the BoNT/A complex is injected at 8 total injection sites in the patient's temporalis muscles, the 8 total injection sites comprising 4 injection sites in the patient's left temporalis muscle and 4 injection sites in the patient's right temporalis muscle;
    f) about 30 total units of the BoNT/A complex is injected at 6 total injection sites in the patient's trapezius muscles, the 6 total injection sites comprising 3 injection sites in the patient's left trapezius muscle and 3 injection sites in the patient's right trapezius muscle; and
    g) about 20 total units of the BoNT/A complex is injected at 4 total injection sites in the patient's cervical paraspinal muscles, the 4 total injection sites comprising 2 injection sites in the patient's left cervical paraspinal muscle and 2 injection sites in the patient's right cervical paraspinal muscle; and
    wherein about 5 units of the BoNT/A complex is injected at each of the 31 injection sites.

13. The method of claim 12, wherein the BoNT/A complex is a 900 kD complex.

14. The method of claim 12, wherein the BoNT/A complex is onabotulinumtoxinA.

15. The method of claim 12, wherein the composition comprises a powdered BoNT/A pharmaceutical composition that has been reconstituted with normal saline, wherein prior to the reconstitution, the powdered BoNT/A pharmaceutical composition consists of the BoNT/A complex, human albumin, and sodium chloride.

16. The method of claim 12, wherein the injections are not made deeper than about 0.5 inches into a muscle.

17. The method of claim 12, wherein the composition is administered to the patient using a sterile 30-gauge syringe with a 0.5 inch needle.

18. The method of claim 12, wherein the composition is administered to the patient using a sterile 30-gauge syringe with a 1 inch needle.

19. The method of claim 12, wherein the method is repeated every 12 weeks.

\* \* \* \* \*